US009884109B2

(12) United States Patent
Drummer et al.

(10) Patent No.: US 9,884,109 B2
(45) Date of Patent: Feb. 6, 2018

(54) COMPOSITIONS AND METHODS

(75) Inventors: Heidi Drummer, Ascot Vale (AU);
Kathleen McCaffrey, Singapore (SG);
Pantelis Poumbourios, Ascot Vale
(AU)

(73) Assignee: The Macfarlane Burnet Institute for Medical Research and Public Health Ltd, Melbourne (AU)

( * ) Notice: Subject to any disclaimer, the term of this patent is extended or adjusted under 35 U.S.C. 154(b) by 672 days.

(21) Appl. No.: 13/989,598

(22) PCT Filed: Nov. 25, 2011

(86) PCT No.: PCT/AU2011/001534
§ 371 (c)(1),
(2), (4) Date: Aug. 12, 2013

(87) PCT Pub. No.: WO2012/068637
PCT Pub. Date: May 31, 2012

(65) Prior Publication Data
US 2013/0323282 A1    Dec. 5, 2013

Related U.S. Application Data

(60) Provisional application No. 61/417,317, filed on Nov. 26, 2010.

(51) Int. Cl.
| A61K 39/00 | (2006.01) |
| C07K 14/005 | (2006.01) |
| A61K 38/00 | (2006.01) |
| C07K 16/10 | (2006.01) |
| A61K 39/12 | (2006.01) |
| A61K 39/29 | (2006.01) |
| G01N 33/576 | (2006.01) |

(52) U.S. Cl.
CPC ............. *A61K 39/29* (2013.01); *A61K 39/12* (2013.01); *C07K 14/005* (2013.01); *G01N 33/5767* (2013.01); *A61K 2039/55577* (2013.01); *A61K 2039/70* (2013.01); *C12N 2770/24222* (2013.01); *C12N 2770/24234* (2013.01); *C12N 2770/24271* (2013.01); *G01N 2333/186* (2013.01); *G01N 2400/02* (2013.01); *G01N 2469/20* (2013.01); *G01N 2800/52* (2013.01)

(58) Field of Classification Search
CPC .. A61K 38/00; A61K 39/00; A61K 2039/525; C07K 14/005; C07K 14/21
See application file for complete search history.

(56) References Cited

U.S. PATENT DOCUMENTS

| 7,413,741 B2 | 8/2008 | Depraetere et al. ........ 424/184.1 |
| 8,535,686 B2 | 9/2013 | McCaffrey et al. ........ 424/228.1 |
| 9,079,950 B2 | 7/2015 | Drummer et al. .......... 424/228.1 |
| 2004/0191270 A1* | 9/2004 | Drane et al. ............ A61K 39/29 424/189.1 |
| 2011/0014209 A1 | 1/2011 | McCaffrey ................. 424/161.1 |
| 2013/0224246 A1 | 8/2013 | Drummer et al. ......... 424/228.1 |
| 2014/0120127 A1 | 5/2014 | Mccaffrey et al. ........ 424/228.1 |

FOREIGN PATENT DOCUMENTS

| WO | WO 96/11698 | 4/1996 |
| WO | WO9966033 | * 12/1999 |
| WO | WO 02/094874 | 11/2002 |
| WO | WO02094874 | * 11/2002 |
| WO | WO 03/047617 | 6/2003 |
| WO | WO 2008/022401 | 2/2008 |
| WO | WO2008022401 | * 2/2008 |
| WO | WO 2009/131681 | 10/2009 |

OTHER PUBLICATIONS

Rodriguez et al. "Structural properties of the ectodomain of hepatitis C virus E2 envelope protein", Virus Research, 2009, 139(1):91-99.*
Whidby et al. "Blocking Hepatitis C virus infection with recombinant form of envelope protein 2 ectodomain", Journal of Virologoy, 2009, 83(21):11078-11089.*
Krey et al. "The disulfide bonds in glycoprotein E2 of hepatitis C virus reveal the tertiary organization of the molecule", PLoS Pathogens, 2010, 6(2):1-11).*
Letter/Written Disclosure of the Information Disclosure Statement for the above-referenced application, dated Jun. 29, 2015, 2 pages.
Ausubel et al., *Current Protocols in Molecular Biology*, John Wiley & Sons Inc., Unit 2.10.1 to 2.10.16, 16 pages (1994-1998).
Boo et al., "Distinct roles in folding, CD81 receptor binding and viral entry for conserved histidine residues of hepatitis C virus glycoprotein E1 and E2," Biochem J. 443(1):85-94 (2012).
Ciczora et al., "Contribution of the charged residues of hepatitis C virus glycoprotein E2 transmembrane domain to the functions of the E1E2 heterodimer," J. Gen Virol 86:2793-2798 (2005).
Ciczora et al., "Transmembrane domains of hepatitis C virus envelope glycoproteins: residues invovled in E1 E2 heterodimerization and invovlement of these domains in virus enry," J. Virol 81(5): 2372-2381 (2007).
Drummer, H., "Challenges to the development of vaccines to hepatitis C virus that elicit neutralizing antibodies," Front Microbial. 5:329, 10 pages (2014).
Fenouillet et al., "Contribution of redox status to hepatitis C virus E2 envelope protein function and antigenicity," J. Biol. Chem. 283(39): 26340-26348 (2008).

(Continued)

Primary Examiner — Barry A Chestnut
(74) Attorney, Agent, or Firm — Dentons US LLP; Stephanie Seidman

(57) ABSTRACT

The present invention provides a composition comprising hepatitis C virus (HCV) Envelope 2 (E2) glycoprotein, wherein the HCV E2 is substantially monomer depleted HCV E2. Also provide are methods of inducing an HCV immune response.

12 Claims, 60 Drawing Sheets

(56) References Cited

OTHER PUBLICATIONS

Figure 1:
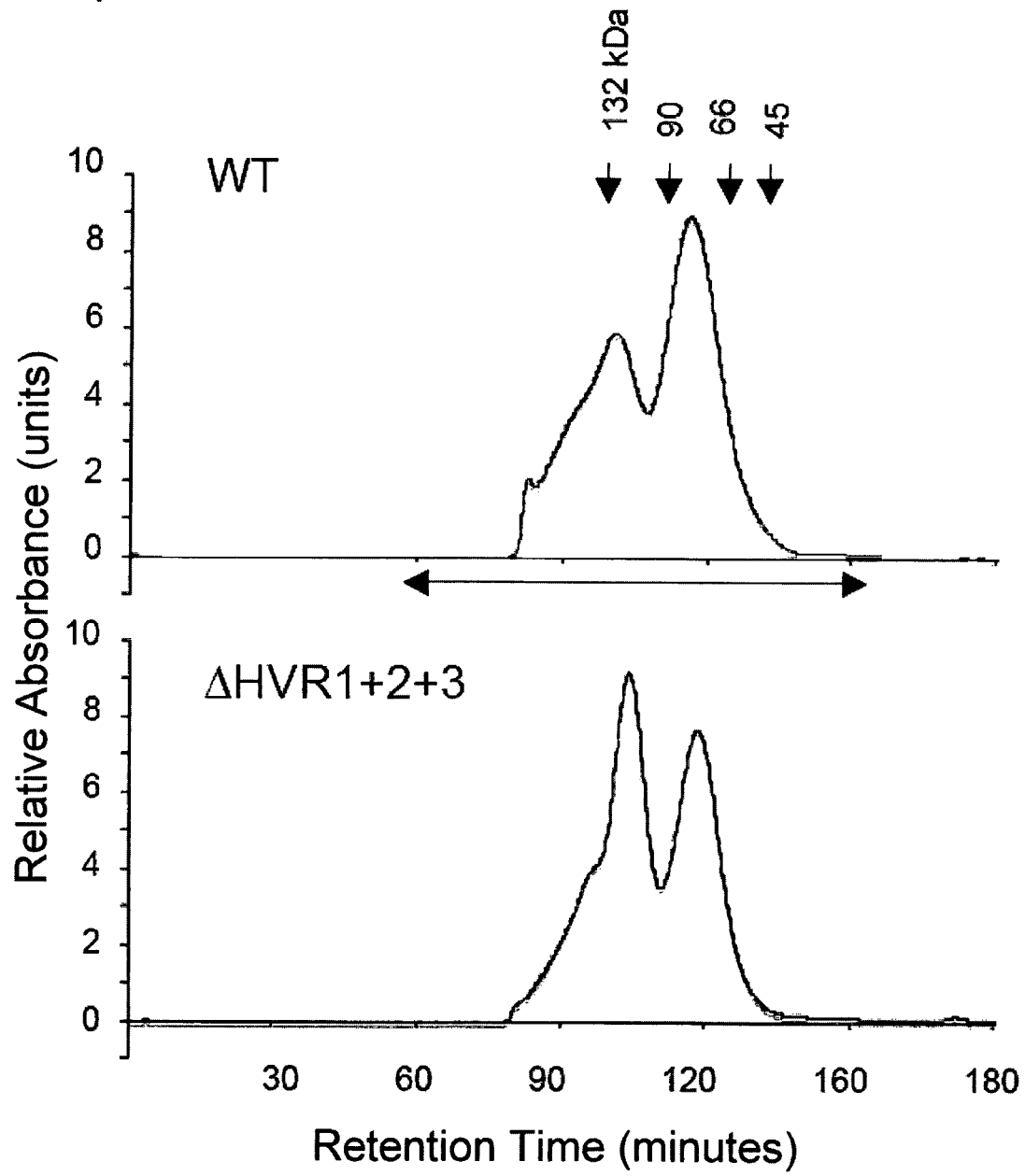

Grove et al., "Identification of a residue in hepatitis C virus E2 glycoprotein that determines scavenger receptor BI and CD81 receptor dependency and sensitivity to neutralizing antibodies." J Virol. 82(24):12020-12029 (2008).
Hepatitis C virus (isolate JFH-1) genomic RNA, complete genome (GenBank Accession No. AB047639), Published on Nov. 12, 2005 [online][retrieved on Apr. 7, 2015] Retrieved from:<URL:ncbi.nlm.nih.gov/nuccore/AB047639 [4 pages].
Hepatitis C virus type 1b complete genome, isolate Con1 (GenBank Accession No. AJ238799), Published on Apr. 15, 2005 [online][retrieved on Sep. 22, 2011] Retrieved from:<URL:ncbi.nlm.nih.gov/nuccore/AJ238799 [6 pages].
Keck et al., "Analysis of a highly flexible conformational immunogenic domain A in hepatitis C virus E2," J. Virol. 79(21):13199-13208 (2005).
Keck et al., "Hepatitis C virus E2 has three immunogenic domains containing conformational epitopes with distinct properties and biological functions," J. Virol., 78(17):9224-9232 (2004).
Maraskovsky et al., "Development of prophylactic and therapeutic vaccines using the ISCOMATRIX adjuvant," Immunol Cell Biol. 87(5):371-376 (2009).
Owisanka et al., "Identification of conserved residues in the E2 envelope glycoprotein of the hepatitis C virus that are critical for CD81 binding," J. Virol. 80(17):8695-8704 (2006).
Poumbourios, P. and H. Drummer, "Recent advances in our understanding of receptor binding, viral fusion and cell entry of hepatitis C virus: new targets for the design of antiviral agents," Antivir Chem Chemother., 18(4):169-189 (2007).
Roccasecca et al., "Binding of the hepatitis C virus E2 glycoprotein to CD81 is strain specific and is modulated by a complex interplay between hypervariable regions 1 and 2," J Virol 77(3):1856-1867 (2003).
Vieyres et al., "Characterization of antibody-mediated neutralization directed against the hypervariable region 1 of hepatitis C virus E2 glycoprotein," J. Gen. Virol. 92:494-506 (2011).
Wahid et al., "Disulfide bonds in hepatitis C virus glycoprotein E1 control the assembly and entry functions of E2 glycoprotein," J. Virol. 87(3):1605-1617 (2013).
Wang et al., "Alanine scanning mutagenesis of hepatitis C virus E2 cysteine residues: Insights into E2 biogenesis and antigenicity." Virology 448:229-237 (2014).
Yagnik et al. "A model for the Hepatitis C Virus envelope glycoprotein E2." Proteins: Structure, Function and Genetics (40):355-366 (2000).
International Search Report, issued Jan. 18, 2012, in connection with International Patent Application, PCT/AU2011/000991, 4 pages.
Written Opinion, dated Jan. 16, 2012, in connection with International Patent Application, PCT/AU2011/000991, 6 pages.
International Preliminary Report on Patentability, dated Feb. 5, 2013, in connection with International Patent Application, PCT/AU2011/000991, 7 pages.
Response to Rule 161(2) and 162 communication, submitted Sep. 30, 2013, in connection with European Patent Application No. 11 813 954.2, 7 pages.
Extended European Search Report and Written Opinion, dated Nov. 27, 2013, in connection with European Patent Application No. 11 813 954.2, 6 pages.
Response to Rule 161(2) and 162 communication, dated Feb. 10, 2014, in connection with European Patent Application No. 11 843 279.8, 6 pages.
Examination Report, dated May 21, 2014, in connection with Australian Patent Application No. 2011286168, 3 pages.
Examination Report, dated Jun. 2, 2014, in connection with Australian Patent Application No. 2011334543, 4 pages.
Response to Search Report and Written Opinion, dated Jun. 23, 2014, in connection with European Patent Application No. 11 813 954.2, 7 pages.

Restriction Requirement, dated Jun. 24, 2014, in connection with U.S. Appl. No. 13/813,929, 9 pages.
Response to Restriction Requirement, dated Aug. 25, 2014, in connection with U.S. Appl. No. 13/813,929, 11 pages.
Notice of Allowance, dated Sep. 25, 2014, in connection with U.S. Appl. No. 13/813,929, 11 pages.
Preliminary Amendment and Request for Continued Examination, dated Dec. 29, 2014, in connection with U.S. Appl. No. 13/813,929, 5 pages.
Notice of Allowance, dated Mar. 13, 2015, in connection with U.S. Appl. No. 13/813,929, 8 pages.
Response to Examination Report, dated Apr. 14, 2015, in connection with Australian Patent Application No. 2011334543, 8 pages.
Response to Examination Report, dated Apr. 15, 2015, in connection with Australian Patent Application No. 201128168, 9 pages.
Notice of Acceptance, dated May 6, 2015, in connection with Australian Patent Application No. 2011334543, 5 pages.
Notice of Acceptance, dated May 14, 2015, in connection with Australian Patent Application No. 2011286168, 5 pages.
Extended European Search Report, dated Jun. 3, 2015, in connection with European Patent Application No. 11 843 279.8, 7 pages.
Letter/Written Disclosure of the Supplemental Information Disclosure Statement for the above-referenced application, mailed the same day herewith, 2 pages.
Angus, A. and A. Patel, "Immunotherapeutic potential of neutralizing antibodies targeting conserved regions of the HCV envelope glycoprotein E2," Future Microbiol 6(3):279-294 (2011).
Atherton, E. and R. Sheppard, "Analytical and monitoring techniques," found in: *Solid Phase Peptide Synthesis: a practical approach*, (*the Practical Approach Series*), Chapter 9, 107-123 (1989).
Bartosch et al., "Cell entry of hepatitis C virus requires a set of co-receptors that include the CD81 tetraspanin and the SR-B1 scavenger receptor," J. Biol. Chem. 278(43):41624-41630 (2008).
Blish et al., "Enhancing exposure of HIV-1 neutralization epitopes through mutations in gp41," PLoS Med. 5(1):90-103 (2008).
Cox, J. and A. Coulter, "Advances in Adjuvant Technology and Application", found in: *Animal Parasite Control Utilizing Biotechnology*, Chapter 4, Ed. Young, W., CRC Press, Boca Raton, FL., pp. 51-112 (1992).
Cox, J. and A. Coulter," Adjuvants—a classification and review of their modes of action," Immunology Research 15(3): 248-256 (1997).
Dorner et al., "A genetically humanized mouse model for hepatitis C virus infection," Nature 474(7350): 208-211 (2009).
Drummer et al., "Identification of the hepatitis C virus E2 glycoprotein binding site on the large extracellular loop of CD81," J. Virol. 76(21):11143-11147 (2002).
Drummer et al., "Cell surface expression of functional hepatitis C virus E1 and E2 glycoproteins," FEBS Lett 546(2-3):385-390 (2003).
Drummer et al., "Determinants of CD81 dimerization and interaction with hepatitis C virus glycoprotein E2," Biochem Biophys Res Commun 328(1):251-257 (2005).
Drummer et al., "A Conserved Gly436-Trp-Leu-Ala-Gly-Leu-Phe-Tyr motif in hepatitis C virus glycoprotein E2 is a determinant of CD81 binding and viral entry," J. Virol. 80(16):7844-7853 (2006).
Drummer et al., "Mutagenesis of a conserved fusion peptide-like motif and membrane-proximal heptad-repeat region of hepatitis C virus glycoprotein E1," J. Gen. Virol. 88:1144-1148 (2007).
Drummer, H. and P. Poumbourios, "Hepatitis C virus glycoprotein E2 contains a membrane-proximal heptad repeat sequence that is essential for E1E2 glycoprotein heterodimerization and viral entry," J. Biol. Chem. 279(29):30066-30072 (2004).
Fraser et al., "Hepatitis C virus (HCV) envelope glycoproteins E1 and E2 contain reduced cysteine residues essential for virus entry," J. Biol. Chem. 286(37):31984-31992 (2011).
Harris et al., "Claudin association with CD81 defines hepatitis C virus entry," J. Biol. Chem. 285(27):21092-21102 (2010).
Kaufmann et al., "Neutralization of West Nile virus by cross-linking of its surface proteins with Fab fragments of the human monoclonal antibody CR4354," Proc. Natl. Acad. Sci. USA 107:18950-18955 (2010).

(56) References Cited

OTHER PUBLICATIONS

Koutsoudakis et al., "The Level of CD81 cell surface expression is a key determinant for productive entry of hepatitis C virus into host cells," J. Virol. 81(2):588-598 (2007).
Kozak, M. and A. Shatkin, "Characterization of translational initiation regions from eukaryotic messenger RNAs," Methods Enzymol 60:360-375 (1979).
Kozak, M., "The Scanning model for translation: an update," J Cell Biol 108(2):229-241 (1989).
Kozak, M., "Determinants of translational fidelity and efficiency in vertebrate mRNAs," Biochimie 76(9):815-821 (1994).
Kozak, M., "Interpreting cDNA sequences: some insights from studies on translation," Mamm Genome 7(8):563-574 (1996).
Krey et al., "The Disulfide bonds in glycoprotein E2 of hepatitis C virus reveal the tertiary organization of the molecule," PLoS Pathogens 6(2):e1000762, 11 pages. (2010).
Law et al., "Broadly neutralizing antibodies protect against hepatitis C virus quasispecies challenge," Nature Medicine 14(1):25-27 (2008).
Lindenbach et al., "Complete replication of hepatitis C virus in cell culture," Science 309(5734):623-626 (2005).
Lusso et al., "Cryptic nature of a conserved, CD4-inducible V3 loop neutralization epitope in the native envelope glycoprotein oligomer of CCR5-restricted, but not CXCR4-using, primary human immunodeficiency virus type 1 strains," J Virol 79(11):6957-6968 (2005).
Mancini et al., "Hepatitis C virus (HCV) infection may elicit neutralizing antibodies targeting epitopes conserved in all viral genotypes," PLoS One 4:e8254, 7 pages (2009).
McCaffrey et al., "Expression and characterization of a minimal hepatitis C virus glycoprotein E2 core domain that retains CD81 binding," J Virol. 81:9584-9590 (2007).
McCaffrey et al., "Role of conserved cysteine residues in hepatitis C virus glycoprotein E2 folding and function," J. Virol. 86(7):3961-3974 (2012).
McCaffrey et al., "The variable regions of hepatitis C virus glycoprotein E2 have an essential structural role in glycoprotein assembly and virion infectivity," J. Gen. Virol. 92(1):112-121 (2011).
McKeating et al., "Diverse hepatitis C virus glycoproteins mediate viral infection in a CD81-dependent," J. Virol. 78(16):8496-8505 (2004).
Patel et al., "Covalent interactions are not required to permit or stabilize the non-covalent association of hepatitis C virus glycoproteins E1 and E2," J. Gen. Virol. 80:1681-1690 (1990).
Pestka et al., "Rapid induction of virus-neutralizing antibodies and viral clearance in a single-source outbreak of hepatitis C," Proc. Natl. Acad. Sci. USA 104(14):6025-6030 (2007).
Pileri et al., "Binding of hepatitis C virus to CD81," Science 282:938-941 (1998).
Reed, L. and H. Meunch, "A simple method of estimating fifty percent endpoints," The American Journal of Hygiene 27:493-497 (1938).
Roberge et al., "A Strategy for a convergent synthesis of N-linked glycopeptides on a solid support," Science 269(5221):202-204 (1995).
Rodriguez-Rodriguez et al., "Structural properties of the ectodomain of hepatitis C virus E2 envelope protein," Virus Research 139(1):91-99 (2009).
Sambrook et al., found in: *Molecular Cloning: A Laboratory Manual*, Cold Spring Harbor Laboratory, Cold Spring Harbor, N.Y. Sections 1.101 to 1.104, 16 and 17 (1989).
Sharp, P. and E. Cowe, "Synonymous codon usage in *Saccharomyces cerevisiae*," Yeast 7(7):657-678 (1991).
Stamataki et al., "Hepatitis C virus entry and neutralization," Clinics in Liver Disease 12(3):693-712 (2008).
Stiasny et al., "Cryptic properties of a cluster of dominant flavivirus cross-reactive antigenic sites," J. Virol. 80(19):9557-9568 (2006).
Sultana et al., "Fusion loop peptide of the west nile virus envelope protein is essential for pathogenesis and is recognized by a therapeutic cross-reactive human monoclonal antibody," J. Immunol. 183:650-660 (2009).
Whidby et al., "Blocking hepatitis C virus infection with recombinant form of envelope protein 2 ectodomain," J. Virol. 83(21): 11078-11089 (2009).
Vanwolleghem et al., "Polyclonal immunoglobulins from a chronic hepatitis C virus patient protect human liver-chimeric mice from infection with a homologous hepatitis C virus strain," Hepatology 47(6):1846-1855 (2008).
Youn et al., "Sustained E2 antibody response correlates with reduced peak viremia after hepatitis C virus infection in the chimpanzee," Hepatology 42(6):1429-1436 (2005).
Zhang et al., "CD81 is required for hepatitis C virus glycoprotein-mediated viral infection," J. Virol. 78(3):1448-1455 (2004).
International Preliminary Report on Patentability, dated May 28, 2013, in connection with corresponding International Patent Application, PCT/AU2011/001534, 5 pages.
Written Opinion of the International Searching Authority, dated Jan. 10, 2012, in connection with corresponding International Patent Application, PCT/AU2011/001534, 4 pages.
International Search Report, dated Jan. 10, 2012, in connection with corresponding International Patent Application, PCT/AU2011/001534, 4 pages.
Letter/Written Disclosure of the Supplemental Information Disclosure Statement for the above-referenced application, filed herewith on Nov. 30, 2015, 2 pages.
Letter/Written Disclosure of the Supplemental Information Disclosure Statement for the above-referenced application, filed herewith on Feb. 24, 2017, 2 pages.
Examination Report, dated Nov. 25, 2016, in connection with corresponding Canadian Patent Application No. 2,856,565, 4 pages.
Letter/Written Disclosure of the Supplemental Information Disclosure Statement for the above-referenced application, filed herewith on May 12, 2017, 2 pages.
Office Action, dated Feb. 14, 2017, in connection with corresponding Chinese Patent Application No. 201410558503.0 [Original document in Chinese and English translation], 12 pages.
Letter/Written Disclosure of the Supplemental Information Disclosure Statement for the above-referenced application, filed herewith on Oct. 16, 2017, 3 pages.
Communication Pursuant to Article 94(3) EPC (Examination Report), dated Sep. 15, 2017, in connection with corresponding European Patent Application No. 11843279.8 [D1=Rodriguez-Rodriguez et al., "Structural properties of the ectodomain of hepatitis C virus E2 envelope protein," Virus Research 139(1): 91-99 (2009); D2=WO 2002/094874; D3=Whidby et al., "Blocking hepatitis C virus infection with recombinant form of envelope protein 2 ectodomain," J. Virol. 83(21): 11078-11089 (2009); D4=WO 2009/131681], 5 pages.

\* cited by examiner

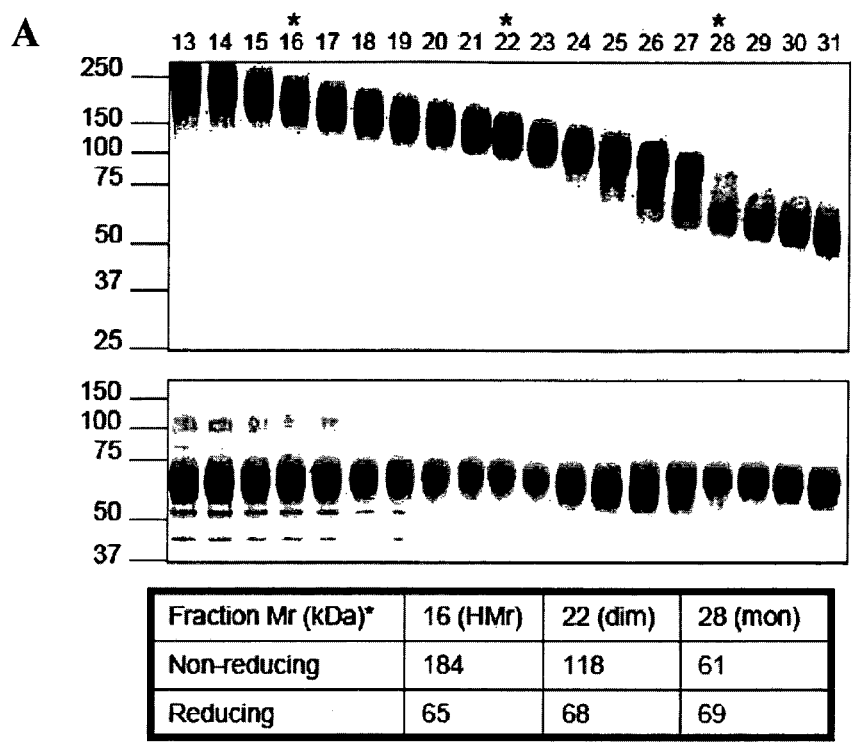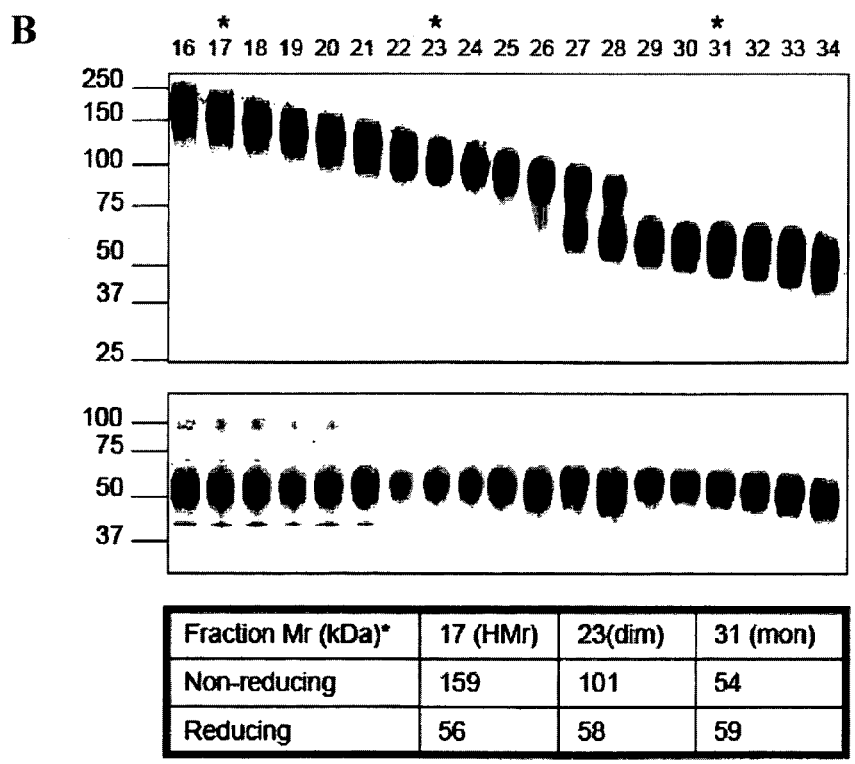
FIGURE 7

Ability of sera to mediate 80% inhibition of homologous H77c WT E2$_{661}$ mixture binding to CD81

Ability of sera to mediate 80% inhibition of heterologous JFH1 WT E2$_{661}$ mixture binding to CD81

FIGURE 14

Western Blot Analysis <u>REDUCING</u>
<u>Probe = anti HCV E2</u>
Anti HCV E2 supplied by Stirling Edwards
| Lane | Sample | Loading Amount (µg) |
|---|---|---|
| 1 | Molecular weight marker* | 12.5 |
| 2 | HCV-His Δ123 Peak 1 | 0.5 |
| 3 | HCV-His Δ123 Peak 2 | 0.5 |
| 4 | HCV-His Δ123 Peak 3 | 0.5 |
| 5 | HCV-His Δ123 Peak 4 | 0.5 |
| 6 | Blank | |
| 7 | HCV-His WT Peak 1 | 0.5 |
| 8 | HCV-His WT Peak 2 | 0.5 |
| 9 | HCV-His WT Peak 3 | 0.5 |
| 10 | HCV-His WT Peak 4 | 0.5 |
*Bio-Rad Prestained SDS-PAGE Standards Broad Range (Catalog# 161-0318)

A

B

A

B

Ability of WT vaccinated guinea pig serum to cross-inhibit binding between WT JFH1 E2 and CD81

Figure 30:
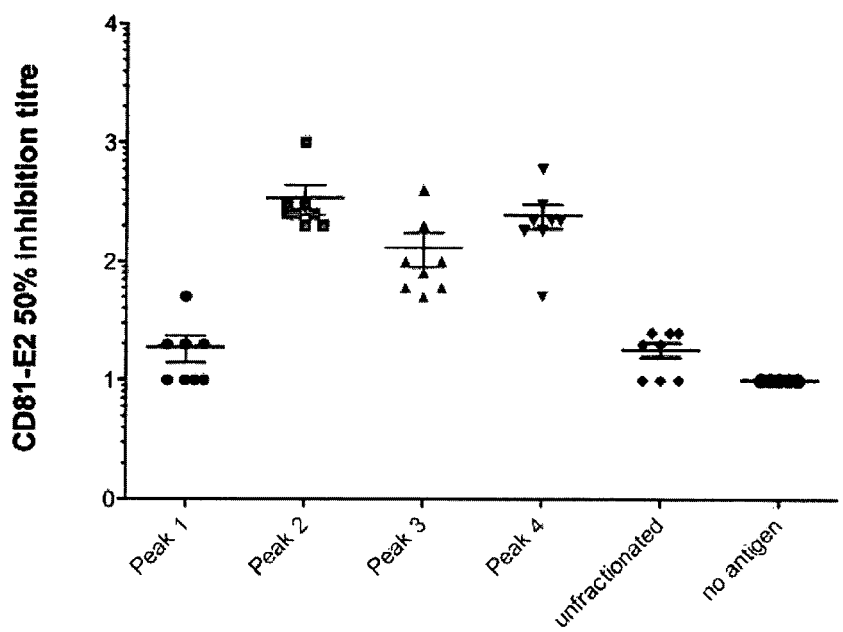

FIGURE 30 (continued)

A

B

Ability of Δ123 vaccinated guinea pig serum to inhibit binding between WT JFH1 E2 and CD81

Figure 31:
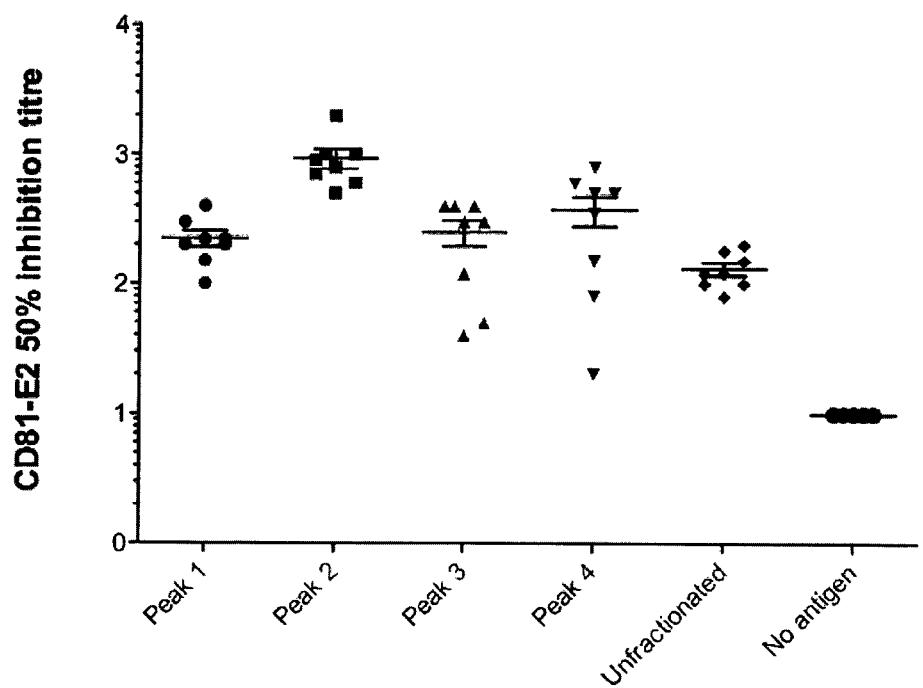

FIGURE 31 (continued)

B

A

B

A

B

A

Reactivity of WT $E2_{661}$ sera to JFH1 WT $E2_{661}$ E2

FIGURE 35

B

A

B

Ability of wild-type immune guinea pig serum to neutralize homologous virus

Figure 36:
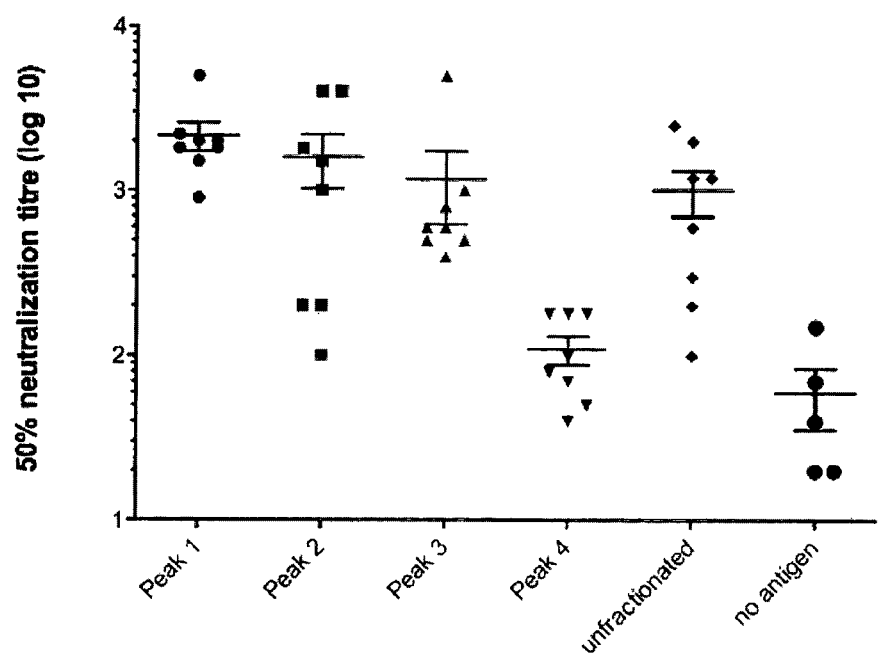

FIGURE 36 (continued)

A

Ability of Guinea Pig immune serum vaccinated
with wild-type $E2_{661}$ antigens to mediate
heterologous HCV neutralization

FIGURE 37

B

Ability of Guinea Pig immune serum vaccinated with wild-type $E2_{661}$ antigens to mediate heterologous HCV neutralization

FIGURE 37 (continued)

A

Reactivity of Wild-type $E2_{661}$ vaccinated guinea pigs to WT Con1 $E2_{661}$ antigen

FIGURE 38

B

Reactivity of Wild-type $E2_{661}$ vaccinated guinea pigs to $\Delta 123$ Con1 $E2_{661}$ antigen

FIGURE 38 (continued)

A

Reactivity of Δ123 E2$_{661}$ vaccinated guinea pigs to Con1 Wild-type E2$_{661}$

FIGURE 39

B

Reactivity of Δ123 E2$_{661}$ vaccinated guinea pigs to Con1 Δ123 E2$_{661}$

FIGURE 39 (continued)

A

Reactivity of Δ123 E2$_{661}$ vaccinated guinea pigs to JFH1 wild-type E2$_{661}$

FIGURE 40

B

Reactivity of Δ123 E2$_{661}$ vaccinated guinea pigs to JFH1 Δ123 E2$_{661}$

FIGURE 40 (continued)

COMPOSITIONS AND METHODS

RELATED APPLICATIONS

This application is the National Stage of International Application. No. PCT/AU2011/001534, filed 25 Nov. 2011, which claims benefit of priority to U.S. Provisional Patent Application Ser. No. 61/417,317, filed 26 Nov. 2010, the specification of which is incorporated by reference herein.

FIELD

The present invention relates generally to vaccine and diagnostic compositions for hepatitis C virus (HCV). More particularly, the subject invention provides compositions comprising HCV Envelope 2 (E2) glycoproteins. The compositions are useful inter alia in the treatment, prophylaxis, diagnosis and prognosis of HCV infections.

BACKGROUND

Bibliographic details of references in the subject specification are also listed at the end of the specification.

Reference to any prior art in this specification is not, and should not be taken as, acknowledgement or any form of suggestion that this prior art forms part of the common general knowledge in any country.

According to the World Health Organisation, hepatitis C virus (HCV) infects approximately 170 to 200 million people worldwide. Whilst governments have sought to raise awareness on how HCV is transmitted through infected needles and body fluids and have implemented prevention programs, the incidence of HCV infection continues to increase. Approximately 80% of those who are infected with HCV remain carriers of the virus. In Australia about 16,000 new cases of HCV infection are reported each year, the new infections being most prevalent amongst injection drug users. HCV is the most common blood-borne viral infection, causing the death or morbidity of a substantial proportion of the population.

HCV is known to infect the liver and certain immune cells. As a result, HCV leads to serious liver diseases such as fibrosis, cirrhosis, steatosis and hepatocellular carcinoma (liver cancer) more frequently than other forms of hepatitis. HCV is a leading cause of cancer in liver transplant recipients. It is generally considered that the acute phase of the infection is often unrecognized due to the sub-clinical nature of the infection, and 80% of individuals progress to a chronic condition. Chronic infection is a result of the immune system's failure to generate a sterilizing immune response against the virus. There are six main HCV genotypes (1 to 6) and various subtypes (a, b, c, etc.). Currently, there is no vaccine for HCV and the only available treatment for HCV infection is anti-viral drugs. The general idea behind anti-viral drug design is to identify critical viral proteins, or parts of proteins, that can be disabled or inhibited. A standard treatment of choice for patients suffering moderate or severe fibrosis includes a combination of alpha-interferon and ribavirin. The antiviral effects of combination alpha-interferon and ribavirin therapy cause a rapid decrease in HCV levels in the blood, even after a single dose. Conventional alpha-interferon treatment for HCV however suffers several drawbacks. For example, (i) when alpha-interferon treatment is stopped after a few weeks or months of treatment, the viral load is rapidly re-established; (ii) treatment with alpha-interferon/ribavirin is associated with severe side effects, including flu-like symptoms, reduced red or white cell counts, suppression of bone marrow cells, neuropsychiatric effects, particularly depression and anemia; (iii) effective treatment requires patient adherence to a frequent dosing regimen since alpha-interferon is absorbed and eliminated from the body rapidly; and (iv) high cost of such treatments. Efficacy of the treatment varies with genotype and viral clearance is only obtained for approximately half of patients with genotype 1 or 4.

Some of the above drawbacks, referring particularly to item (iii) above, have been addressed by subjecting alpha-interferon to 'pegylation' in which polyethylene glycol molecules are attached to the interferon. The administration of pegylated interferon in combination with ribavirin increases the half-life of interferon and has the advantage of decreasing the frequency of dosing, hence improving patient compliance. Such treatment, however, has proven to be efficacious in less than 50% of treated patients. Given the increasing number of chronic sufferers of HCV, there is a need to develop a vaccine for both prophylactic and therapeutic purposes.

An essential component of all vaccines is the induction of virus neutralizing antibodies. In the case of HCV, the HCV glycoprotein E2 is the major target of the virus neutralizing antibody response. Neutralizing antibodies have been shown to be important for the clearance of HCV in animal models of HCV infection and in humans (Angus and Patel, 2011, Vanwolleghem et al., 2008, Law et al., 2008, Pestka et al., 2007). As HCV is a highly mutable virus, it is desirable that vaccines to prevent infection with HCV elicit neutralizing antibodies that are able to recognise the broad diversity of genotypes and subtypes of HCV.

The major cellular receptor for HCV is CD81 (Pileri et al., 1998). CD81 is required for entry into liver cells by all strains of HCV (Koutsoudakis et al., 2007, Zhang et al., 2004. McKeating et al., 2004, Bartosch et al., 2003. Pileri et al., 1998). Antibodies with the ability to prevent the interaction of viral particles with CD81 can be neutralizing. (Mancini et al., 2009, Law et al., 2008). High titres of E2-CD81 inhibition antibodies have been correlated with protection from HCV in vaccine studies (Youn et al., 2005) (Stamataki et al., 2008).

However, whilst E2-CD81 inhibition antibodies have been correlated with better protection against HCV in chimpanzees, they are not the only potential mechanism of neutralization. In other viral systems neutralization can be afforded through antibodies directed to the fusion loop (Sultana et al., 2009, Stiasny et al., 2006), and coreceptor interactions (Blish et al., 2008, Lusso et al. 2005). Furthermore, cross-linking of epitopes on the surface of flaviviral particles has been described as a major form of neutralization (Kaufmann et al., 2010).

The HCV glycoprotein E2 contains a discrete receptor binding domain (RBD) spanned by amino acid residues 384-661. The RBD may extend beyond residue 661 to the C-terminal boundary of the ectodomain of E2. Heterologous expression of the E2 RBD results in the secretion of a soluble protein that retains the ability to bind CD81. Within the RBD are three variable regions termed hypervariable region1, hypervariable region 2 (HVR2) and the intergenotypic variable region (igVR). These three variable regions reside outside the core domain of the glycoprotein and do not directly participate in the formation of the CD81 binding site of E2 (McCaffrey et al., 2007). Deletion of the three variable regions from the RBD results in the expression of a soluble form of the glycoprotein that is recognised by conformation dependent antibodies and retains wild-type (WT) levels of CD81 binding. This minimised form of the core domain of E2 is termed Δ123 E2$_{661}$.

Given the drawbacks of current and experimental therapies for the treatment or prevention of HCV infection, there is an urgent unmet need to provide compositions capable of engendering an effective immune response in the treatment and prevention of HCV infection and able to generate diagnostic agents to detect HCV infection and for use in monitoring anti-HCV therapy.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used herein the singular forms "a", "an" and "the" include plural aspects unless the context clearly dictates otherwise. Thus, for example, reference to "a composition" includes a single composition, as well as two or more compositions; reference to "an agent" includes one agent, as well as two or more agents; reference to "the invention" includes single and multiple aspects of the invention; and so forth.

The present invention provides a composition comprising hepatitis C virus (HCV) Envelope 2 (E2) glycoprotein, wherein the HCV E2 glycoprotein (HCV E2) is substantially depleted of HCV E2 monomers. As used herein the phrases "substantially depleted of E2 monomers" or "substantially monomer depleted HCV E2" refers to a composition comprising less than 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% or less than 1% E2 monomers (by weight).

In some embodiments, the proportion of HCV E2 that is in monomeric form is less than 15%, 14%, 13%, 12%, 11%, 10%, 9%, 8%, 7%, 6%, 5%, 4%, 3%, 2%, 1%, 0.5% or 0.1% by weight.

The substantially monomer depleted HCV E2 glycoprotein may be derived from a glycoprotein produced by recombinant or synthetic means.

In a particular embodiment, the compositions are substantially free of monomeric HCV E2 having less than 1% or less than 0.1% monomeric HCV E2.

In a related aspect, the substantially monomer depleted HCV E2 composition is enriched for trimeric HCV E2 and includes preparations of the composition having more than 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% (by weight) trimeric HCV E2 glycoprotein.

In another aspect, the substantially monomer depleted HCV E2 composition is enriched for dimeric HCV E2 and includes preparations of the composition having more than 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% (by weight) dimeric HCV E2 glycoprotein.

In a further aspect, the monomer depleted composition is enriched for trimeric or higher order complexes of HCV E2 and include preparations of the composition having more than 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% (by weight) trimeric or higher order forms of HCV E2 glycoprotein.

In some embodiments, the E2 glycoprotein is substantially HCV E2 trimers. In a related embodiment, the E2 glycoprotein is substantially HCV E2 trimers and higher order forms. In a further embodiment the E2 glycoprotein is substantially higher order forms of HCV E2.

A composition that comprises substantially trimeric HCV E2 includes preparations of the composition having more than 80%, 81%, 82%, 83%, 84%, 85%, 86%, 87%, 88%, 89%, 90%, 91%, 92%, 93%, 94%, 95%, 96%, 97%, 98%, or 99% (by weight) E2 trimers.

A composition that comprises substantially trimeric and higher order forms of HCV E2 includes preparations of the composition having more than 80%, 81%, 82%, 83%, 84%, 85%, 86%, 87%, 88%, 89%, 90%, 91%, 92%, 93%, 94%, 95%, 96%, 97%, 98%, or 99% (by weight) E2 trimers and higher order forms.

A composition that comprises substantially higher order forms of HCV E2 includes preparations of the composition having more than 80%, 81%, 82%, 83%, 84%, 85%, 86%, 87%, 88%, 89%, 90%, 91%, 92%, 93%, 94%, 95%, 96%, 97%, 98%, or 99% (by weight) higher order forms of E2.

In some embodiments, the E2 glycoprotein is substantially HCV E2 dimers.

A composition that comprises substantially dimeric HCV E2 includes preparations of the composition having more than about 80%, 81%, 82%, 83%, 84%, 85%, 86%, 87%, 88%, 89%, 90%, 91%, 92%, 93%, 94%, 95%, 96%, 97%, 98%, or 99% (by weight) E2 dimers.

In some embodiments, the E2 glycoprotein is substantially HCV E2 dimers and E2 trimers.

In some embodiments, the compositions described herein comprising substantially monomer depleted HCV E2 are for use in the treatment and/or prevention of HCV infection.

The present invention further provides a method for eliciting an immune response in a subject or patient, the method comprising administering to the subject or patient an effective amount of a composition comprising substantially monomer depleted HCV E2.

The present invention also provides a method for immunizing a subject against infection from hepatitis C virus comprising administering to the subject a composition comprising substantially monomer depleted HCV E2.

A composition, particularly a vaccine composition for immunizing a subject against infection from hepatitis C virus comprising substantially monomer depleted. HCV E2 is also contemplated by the present invention.

In a related embodiment, the invention also provides a method for treating hepatitis C infection in a subject, comprising administering to the subject a composition comprising substantially monomer depleted HCV E2.

In accordance with these embodiments, the composition is generally administered for a time and under conditions sufficient to elicit an immune response comprising the generation of E2-specific antibodies. The compositions of the present invention may be administered as a single dose or application. Alternatively, the compositions may involve repeat doses or applications, for example the compositions may be administered 2, 3, 4, 5, 6, 7, 8, 9, 10 or more times.

In a further embodiment, the present invention provides a method for producing a purified antibody against substantially monomer depleted HCV E2, comprising injecting into a subject an immunologically effective amount of the substantially monomer depleted HCV E2, and isolating and purifying the antibody produced.

In another embodiment, the substantially monomer depleted HCV E2 composition further comprises a pharmaceutically or physiologically acceptable carrier or diluent.

In a further embodiment, the substantially monomer depleted composition further comprises an adjuvant. In one illustrative embodiment, the adjuvant is a saponin based adjuvant. In a related aspect, the adjuvant is a saponin based adjuvant further comprises cholesterol and sterol, an illustrative example of which is ISCOMATRIX™ adjuvant.

In another embodiment, the present invention provides purified antibodies raised against or reactive with a substantially monomer depleted HCV E2.

In some embodiments, antibodies generated include those that at least partially neutralize an important part of the HCV life cycle such as host cell invasion or viral budding.

The present invention is further directed to the use of substantially monomer depleted HCV E2 in, or in the manufacture of a medicament for, the treatment or prevention of HCV infection.

The present invention also provides for use of substantially monomer depleted HCV E2 in, or in the manufacture of a diagnostic agent (such as an antibody) for, the diagnosis or monitoring of HCV infection or monitoring of an anti-HCV treatment protocol.

In other aspects, screening methods are provided employing substantially monomer depleted HCV E2 to identify binding molecules such as antibodies, antigen-binding fragments, ligands, peptides, organic or inorganic molecules.

In another aspect, the present invention provides a kit or a solid or semi-solid substrate comprising a substantially monomer depleted HCV E2 glycoprotein. The kits or substrates of the present invention are contemplated for use in diagnostic, prognostic, therapeutic or prophylactic applications as well as for use in designing and/or screening HCV E2 binding molecules or HCV receptor binding molecules. The kits and substrates are also useful in monitoring the efficacy of a treatment protocol against HCV infection.

The above summary is not and should not be seen in any way as an exhaustive recitation of all embodiments of the present invention.

BRIEF DESCRIPTION OF THE FIGURES AND TABLE

FIG. 1 provides graphical representations showing preparative size-exclusion chromatography of H77c WT and ΔHVR1+2+3 E2$_{661}$-his. Preparative grade TSKG3000SW size-exclusion profiles of concentrated WT and ΔHVR1+2+3 E2$_{661}$-his proteins in the top and bottom panels, respectively. Samples were run in 1×PBS at a flow-rate of 2 mL/min for 100 mins. 2 mL fractions were collected between 60-160 mins over a number of runs and corresponding fractions pooled for further analysis. Resolved monomer and dimer peaks from both WT and ΔHVR1+2+3 E2$_{661}$-his are shown. Purified bovine serum albumin and ovalbumin protein at 0.5 μg/mL provided size-standards as marked.

Figure 2:
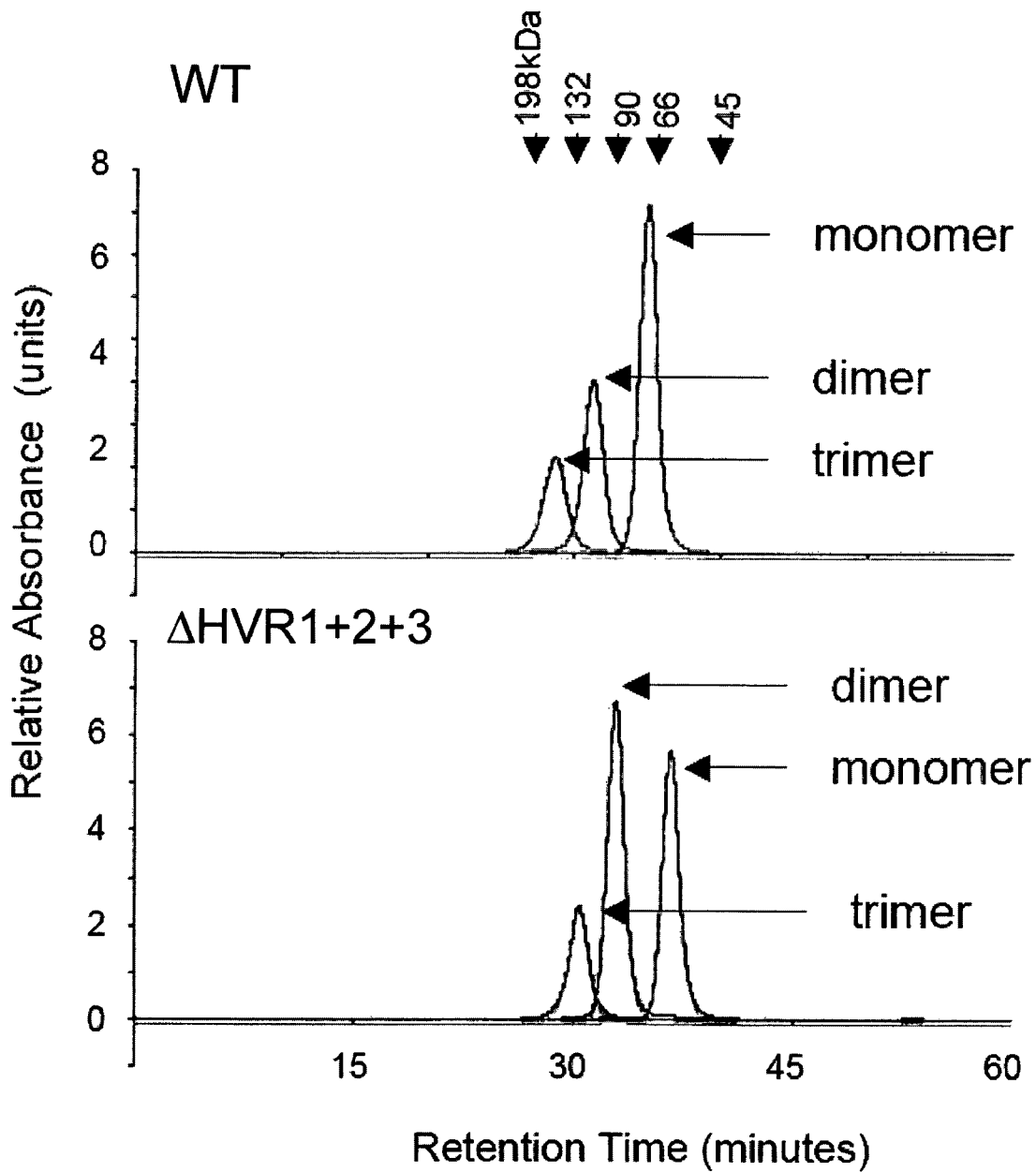

FIG. 2 provides graphical illustrations of data showing the isolation of different forms of H77c WT and ΔHVR1+2+3 E2$_{661}$-his. Analytical TSKG3000SW size-exclusion profiles of pooled fractions representing monomer and dimer peaks as well as an independent high-order molecular mass form (putative trimer) from the preparative size-exclusion chromatography profiles. All samples were run neat in 1×PBS at 0.25 mL/min for 60 mins and resolved monomer, dimer and trimer peaks. Bovine serum albumin and ovalbumin protein at 0.5 mg/mL provided size-standards as marked.

Figure 3:
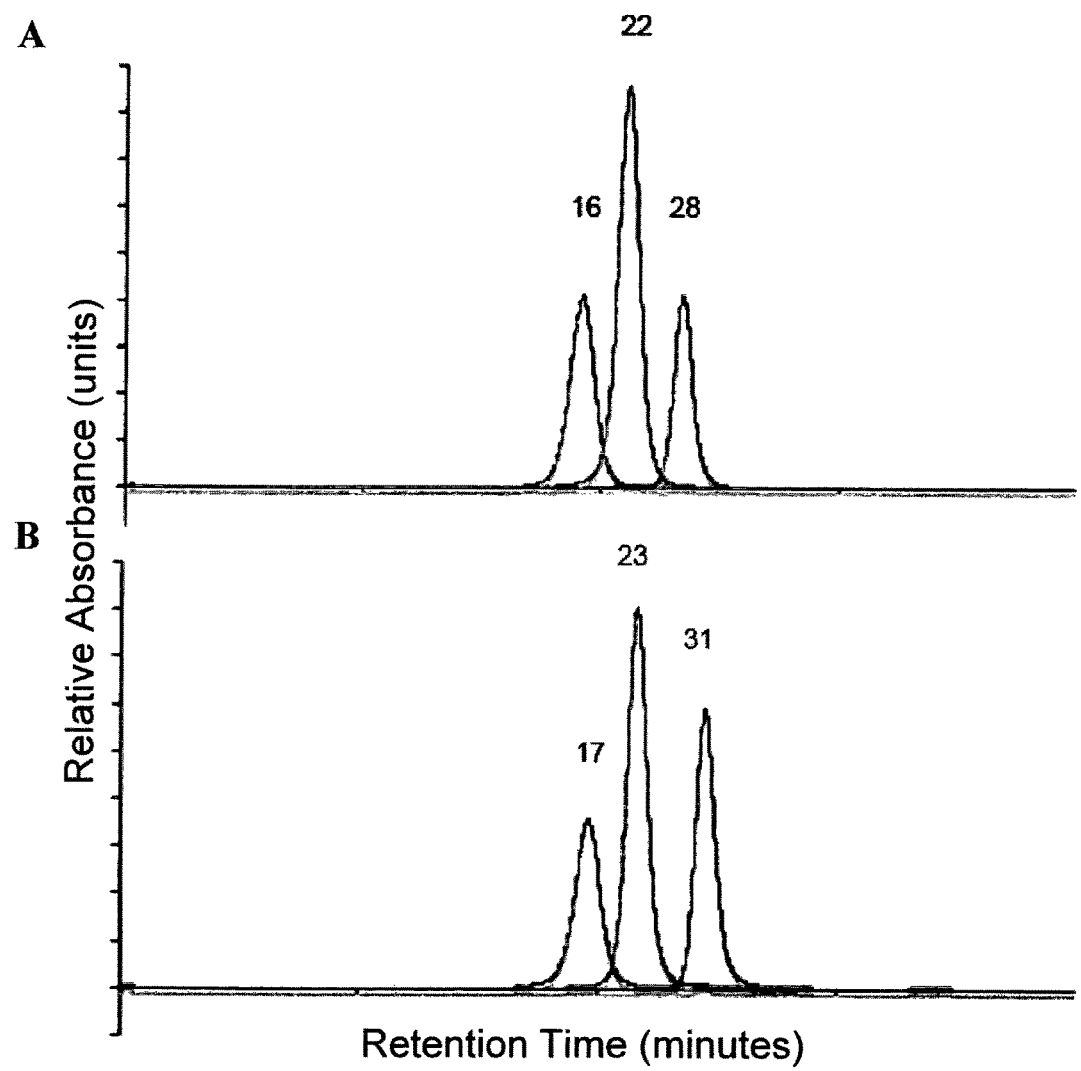

FIG. 3 provides graphical illustrations of data showing the isolation of different forms of Con1 WT and ΔHVR1+2+3 E2$_{661}$-his. Analytical TSKG3000SW size-exclusion profiles of pooled fractions representing monomer and dimer peaks as well as an independent high-order molecular mass form (putative trimer) from the preparative size-exclusion chromatography profiles. A. WT E2$_{661}$-his oligomers and B. ΔHVR1+2+3 E2$_{661}$-his oligomers. All samples were run neat in 1×PBS at 0.25 mL/min for 60 mins and resolved monomer, dimer and trimer peaks.

Figure 4:
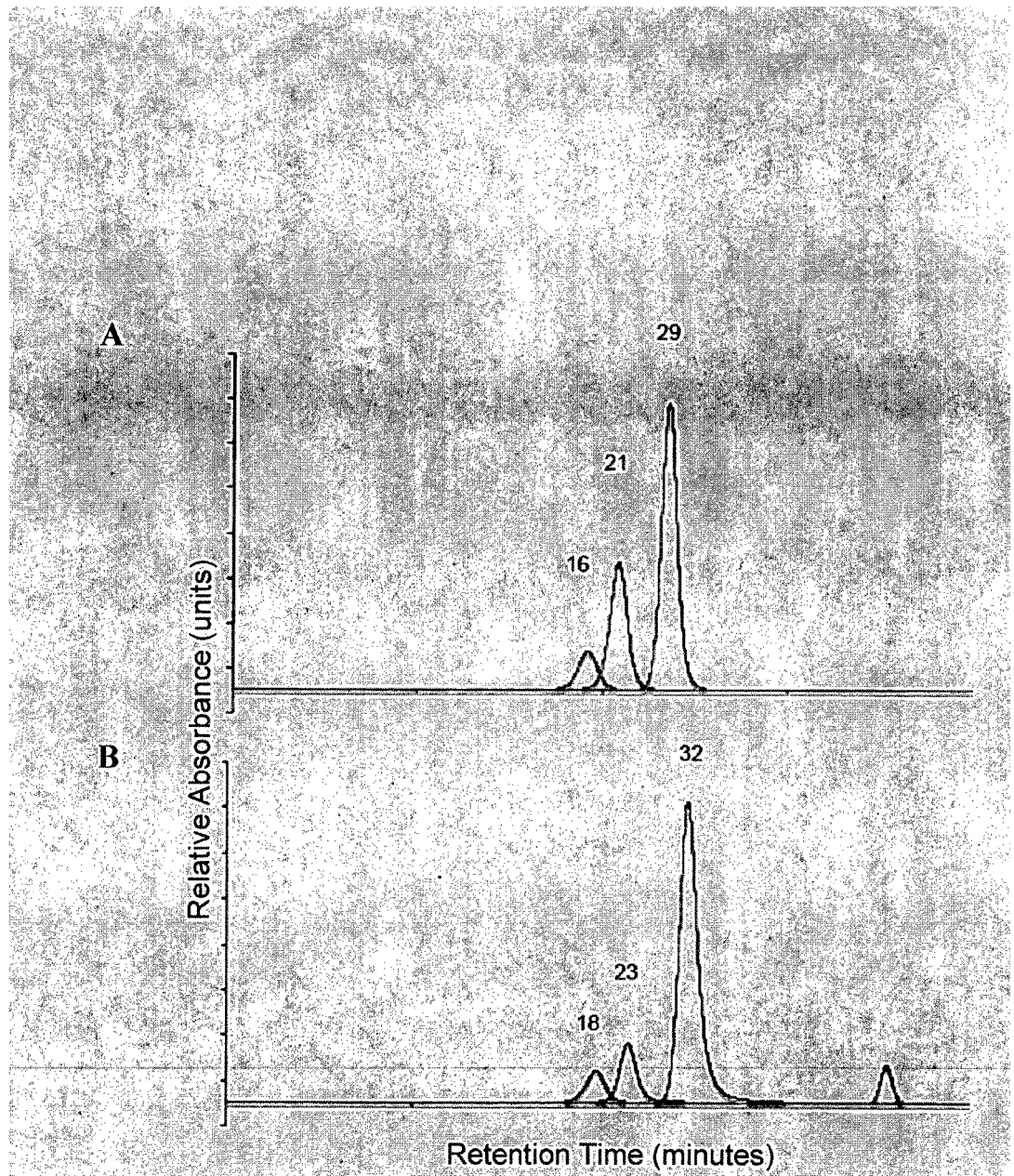

FIG. 4 provides graphical illustrations of data showing the isolation of different forms of JFH1 WT and ΔHVR1+2+3 E2$_{661}$-his. Analytical TSKG3000SW size-exclusion profiles of pooled fractions representing monomer and dimer peaks as well as an independent high-order molecular mass form (putative trimer) from the preparative size-exclusion chromatography profiles. A. WT E2$_{661}$-his oligomers and B. ΔHVR1+2+3 E2$_{661}$-his oligomers. All samples were run neat in 1×PBS at 0.25 mL/min for 60 mins and resolved monomer, dimer and trimer peaks.

Figure 5:
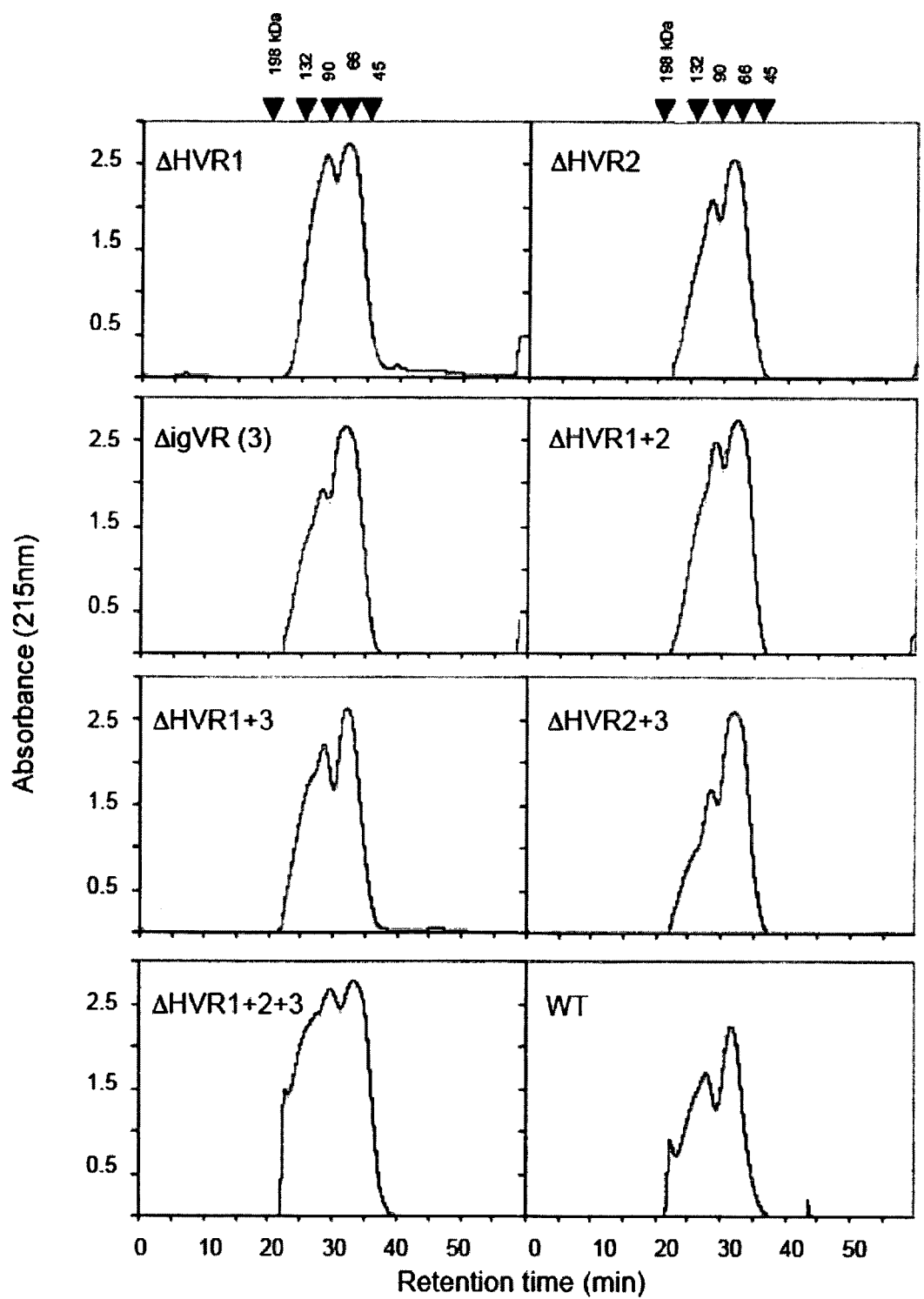

FIG. 5 describes expression profiles of purified E2$_{661}$ proteins lacking individual and multiple variable region sequences. Analytical size-exclusion chromatography profiles of each of the E2$_{661}$-his variable region deletion mutants derived from the H77c genotype 1a is shown as performed using a TSKG3000SW$_{XL}$ column and HPLC system. The different forms of purified bovine serum albumin (BSA) and ovalbumin provided standard size markers as shown.

Figure 6A:
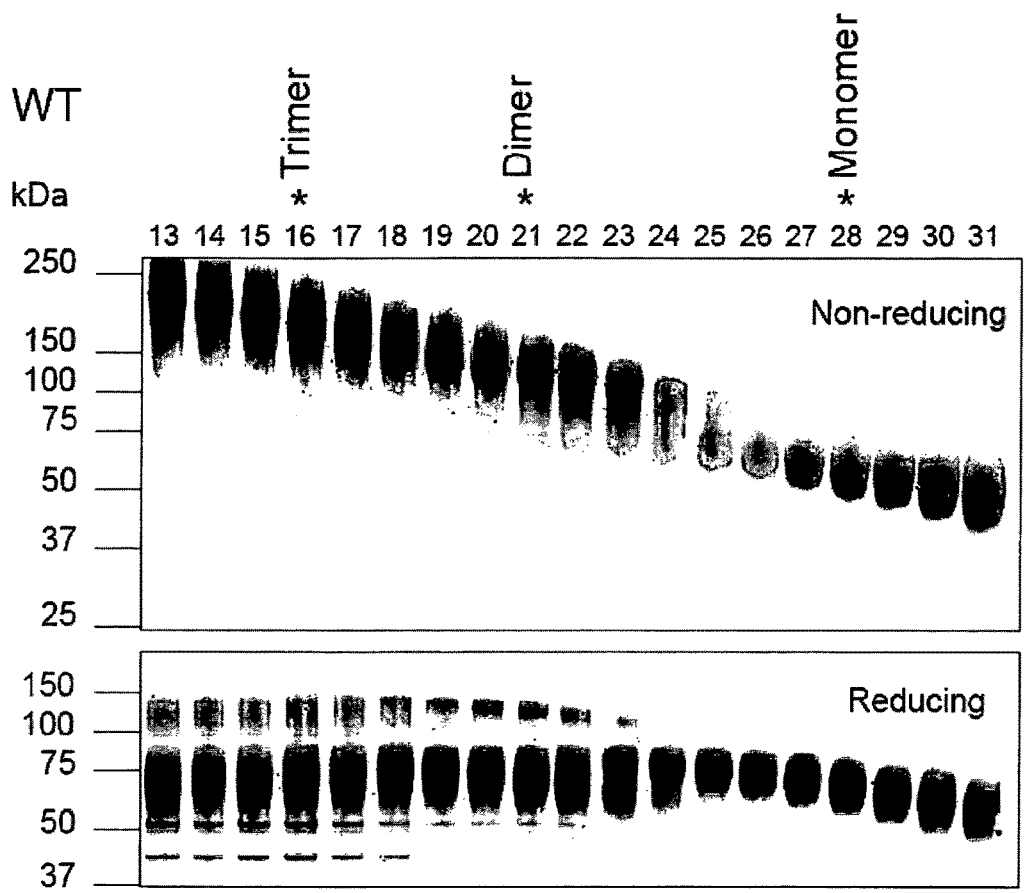
Figure 6B:
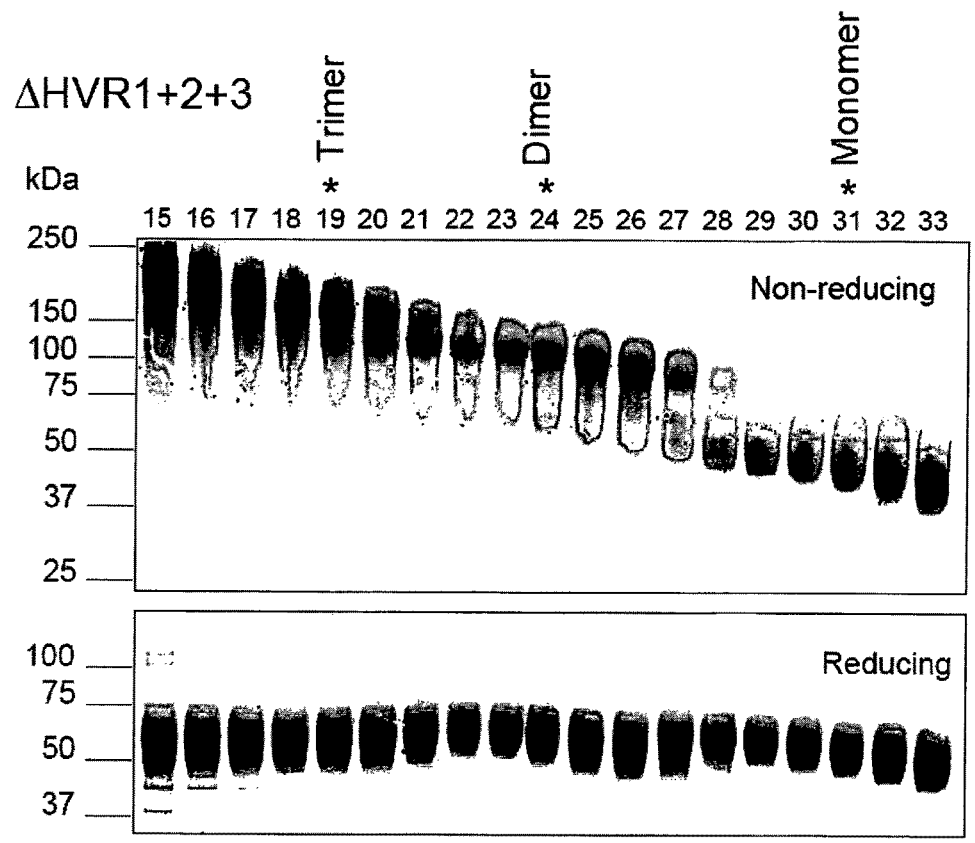

FIGS. 6A and 6B show characterization of different forms of H77c WT and ΔHVR1+2+3 E2$_{661}$-his. Quantitative SDS-PAGE analysis of pooled fractions from preparative size-exclusion chromatography under non-reducing and reducing (+β-mercaptoethanol) conditions using size-standards between 25-200 kDa for A. WT E2$_{661}$-his fractions 13-31 and B. ΔHVR1+2+3 E2$_{661}$-his fractions 15-33. The asterisk (*) indicate fractions representing monomer and dimer peaks as well as an independent high-order molecular mass form (putative trimer) from the analytical size-exclusion chromatography profiles. The table below the figure shows the calculated molecular mass of monomer, dimer, and trimer species estimated from SDS-PAGE analysis.

FIG. 7 describes the characterization of different forms of Con1 WT and ΔHVR1+2+3 E2$_{661}$-his. Quantitative SDS-PAGE analysis of pooled fractions from preparative size-exclusion chromatography under non-reducing and reducing (+β-mercaptoethanol) conditions using size-standards between 25-200 kDa for A. WT E2$_{661}$-his fractions 13-31 and B. ΔHVR1+2+3 E2$_{661}$-his fractions 16-34. The asterisk (*) indicate fractions representing monomer and dimer peaks as well as an independent high-order molecular mass form (putative trimer) from the analytical size-exclusion chromatography profiles. Tabulated beneath each SDS-PAGE result are the calculated molecular masses of fractions corresponding to monomer, dimer and higher molecular mass (HMr) species (putative trimer) in both reducing and non reducing SDS-PAGE.

Figure 8:
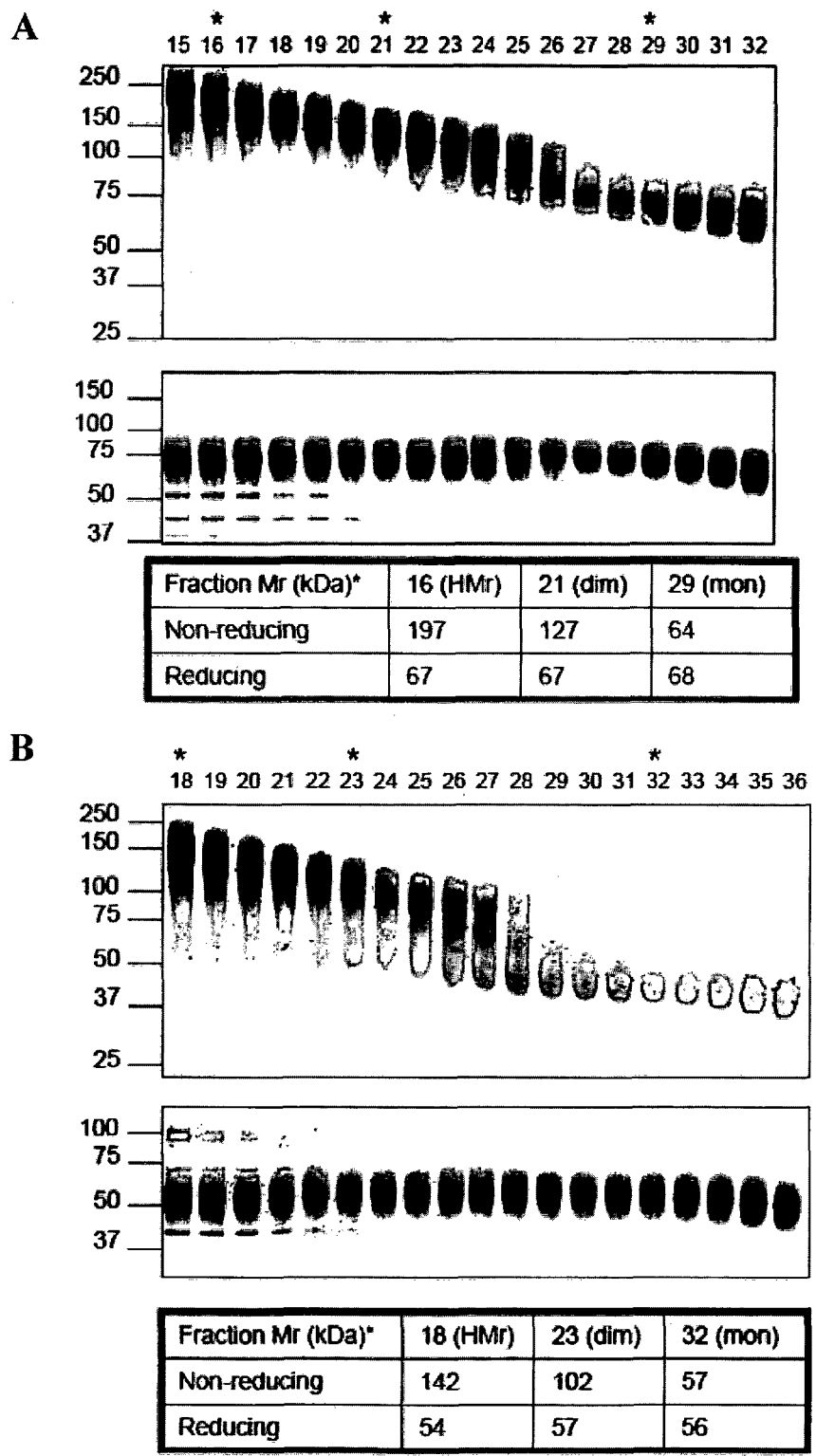

FIG. 8 describes the characterization of different oligomeric forms of JFH1 WT and ΔHVR1+2+3 E2$_{661}$-his. Quantitative SDS-PAGE analysis of pooled fractions from preparative size-exclusion chromatography under non-reducing and reducing (+β-mercaptoethanol) conditions using size-standards between 25-200 kDa for A. WT E2$_{661}$-his fractions 15-32 and B. ΔHVR1+2+3 E2$_{661}$-his fractions 18-36. The asterisk (*) indicate fractions representing monomer and dimer peaks as well as an independent high-order molecular mass form (putative trimer) from the analytical size-exclusion chromatography profiles. Tabulated beneath each SDS-PAGE result are the calculated molecular masses of fractions corresponding to monomer, dimer and higher molecular mass (HMr) species (putative trimer) in both reducing and non reducing SDS-PAGE.

Figure 9:
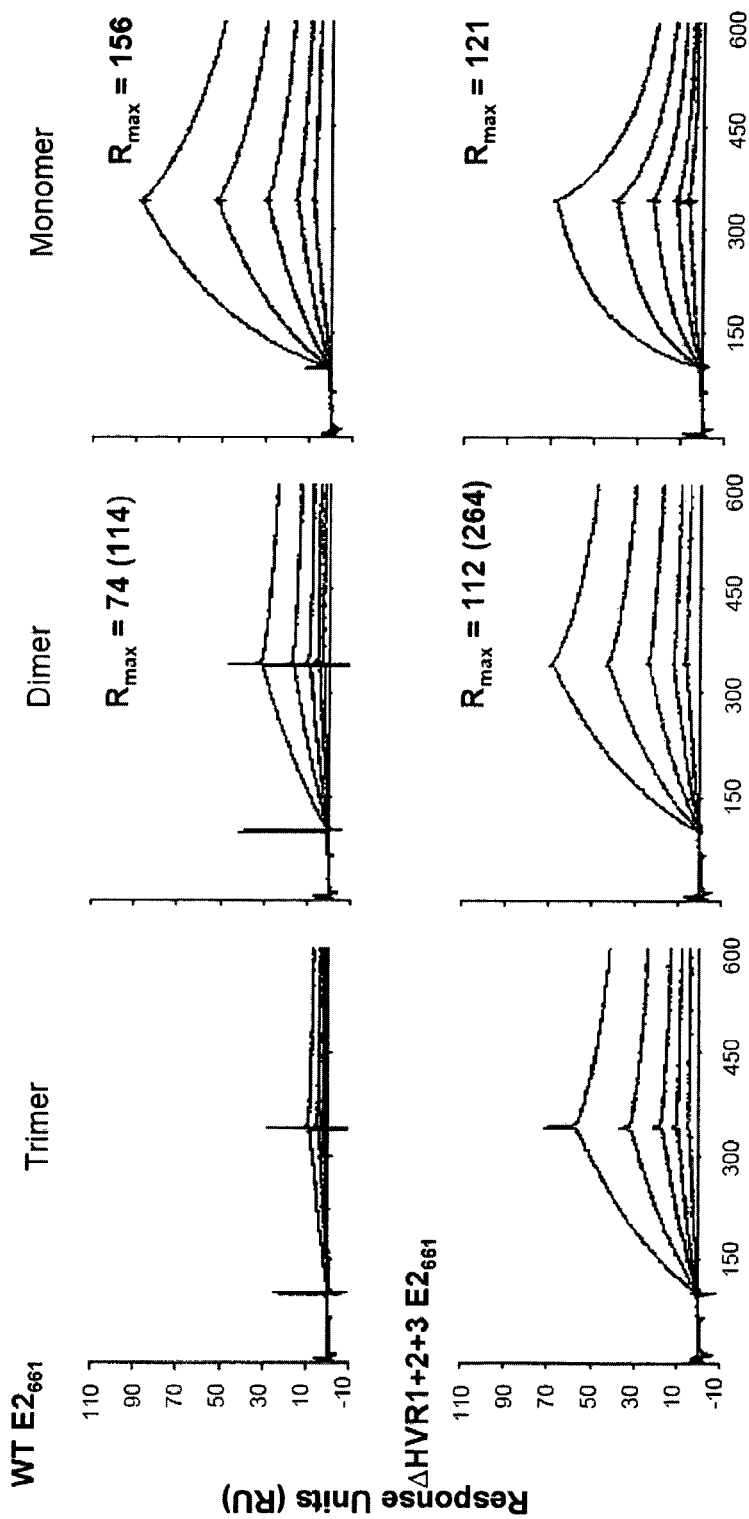

FIG. 9 provides graphical representations showing biosensor curves of different forms of WT and ΔHVR1+2+3 E2$_{661}$-his derived from the H77c isolate. Biosensor curves of different proteins at serial two-fold dilutions starting at 0.1 µg/mL. Top Panel. WT E2$_{661}$-his fractions and Bottom Panel. ΔHVR1+2+3 $E2_{661}$-his fractions each representing trimer, dimer and monomer peaks as determined by analytical size-exclusion chromatography. The vertical bands indicate the position of injection 'start' and 'stop.' The $R_{max}$ values for 1:1 stoichiometry are indicated while the $R_{max}$ values for 2:1 binding stoichiometry are shown in brackets.

FIG. 10 provides graphical representations showing comparative affinity of H77c (genotype 1a), Con1 (genotype 1b) and JFH1 (genotype 2a) WT and ΔHVR1+2+3 $E2_{661}$-his trimer, dimer and monomer proteins binding to the large extracellular loop of CD81 MBP-$LEL^{113-201}$. Average KD values in molar (M) units obtained using the '1:1 Langmuir' binding model for dimer and trimer proteins and 'two-state' (conformational change) model for the monomeric proteins. The average and standard error of three independent experiments are shown, except for Con1 and JFH1 where n=1. Significant differences in KD values ($p<0.05$) obtained for respective WT and ΔHVR1+2+3 $E2_{661}$-his proteins are indicated by an asterisk (*).

FIG. 11 provides graphical representations of data showing the titration curves of guinea pig immune sera generated against dosages of 30 μg or 100 μg monomeric [A (gp1-1 to gp1-4) and B (gp 2-1 to 2-4)], dimeric [C(gp 3-1 to 3-4) and D(gp4-1 to 4-4)] or mixed [E (gp5-1 to 5-4) and F(gp6-1 to 6-4)] E2-his compositions against homologous H77c Δ123 $E2_{661}$-his antigen. The reactivity of guinea pig sera elicited to ISCOMATRIX™ adjuvant alone (no antigen) is shown in lines gp 7-1 to 7-4 in each graph.

FIG. 12 provides graphical representations of antibody mean titres of guinea pig sera against homologous immunizing H77c Δ123 $E2_{661}$-his antigen. Antibody mean titres in the 100 μg mixed group were approximately 0.5 log higher than in the 30 μg mixed group, 1 log higher than the dimer group and 2 logs higher than the monomer group.

FIG. 13 provides graphical representations of data from a direct binding enzyme immunoassay showing the reactivity of immune sera towards mixtures of WT and Δ123 forms of $E2_{661}$-his. Antibody titre was dose dependent with 100 μg appearing to be better than 30 μg. Animals receiving the mixed and dimeric form of $E2_{661}$ elicited higher mean titres of antibody compared to animals vaccinated with monomeric protein.

FIG. 14 provides graphical representations of data illustrating the ability of immune sera to inhibit the binding of H77c (genotype 1a) and JFH1 (genotype 2a) WT $E2_{661}$-his protein to a recombinant form of the large extracellular loop of CD81 (MBP-$LEL^{113-201}$) in a solid phase enzyme assay. Monomeric $E2_{661}$-his vaccinated animals elicited the lowest mean titres of E2-CD81 inhibition antibodies. Animals vaccinated with the dimeric form elicited higher mean titres of H77c E2-CD81 inhibition antibody compared to the monomeric form. Immune sera obtained from animals vaccinated with the mixture containing trimeric species elicited the highest mean titres of H77c E2-CD81 inhibition antibody. In addition, responses were observed in all animals even at the lower vaccine dose of 30 μg indicating that preparations containing trimeric species of $E2_{661}$-his are superior to dimeric $E2_{661}$-his alone. Only sera obtained from animals receiving 30 μg or 100 μg of dimeric or mixtures of $E2_{661}$-his achieved 80% inhibition of the JFH1 E2-CD81 interaction with all animals in the 100 μg mixture group achieving 80% inhibition.

FIG. 15 provides graphical representations of data showing the ability of guinea pig sera to mediate homologous neutralization of H77c HCVpp. The ability to mediate neutralization of HCVpp was also dose and antigen dependent; see monomer (A and B), dimer (C and D), and mixed (E and F). Subjects receiving 30 μg monomer showed poor ability to neutralize HCVpp and the curves are similar to the control no antigen group (G). A positive control using a neutralizing monoclonal antibody directed towards E2 is also shown in G (mab 24).

FIG. 16 provides a graphical representation of 50% neutralization mean titres of guinea pig sera to H77c HCVpp. Subjects receiving 100 μg of mixed antigen elicited neutralization mean titres approximately 10 times higher than to those observed for 100 μg monomer, 30 μg dimer or 100 μg dimer. The 25 and 75 percentiles (boxes), mean (line) and standard error of the mean are shown.

FIG. 17 provides graphical representations illustrating the ability of immune serum to mediate cross neutralization of J6-JFH1 HCVcc for monomer (A and B), dimer (C and D), mixed preparations (E and F). Control no antigen and a neutralizing monoclonal antibody directed towards E2 were also run (G and H). Subjects receiving 100 μg mixed antigen showed a strong ability to mediate cross neutralization achieving 90% inhibition of entry at a 1/40 serum dilution.

FIG. 18 provides a graphical representation of 50% neutralization mean titres of vaccine groups against J6-JFH1 HCVcc. The mean 50% neutralization titre observed for the 100 μg mixed group was almost 2 logs higher than the 30 μg and 100 μg monomer groups and 1 log higher than the dimer groups and 30 μg mixed group.

FIG. 19 provides a representative gel filtration chromatogram of WT $E2_{661}$-his protein. Protein was run on a Superdex 200 pg 26/60 preparative gel filtration column and peaks 1-4 collected as indicated. Elution times for molecular weight standards are indicated above the chromatograms.

FIG. 20 provides a representative gel filtration chromatogram of Δ123 $E2_{661}$-his protein. Proteins were run on a Superdex 200 pg 26/60 preparative gel filtration column and peaks 1-4 collected as indicated. Elution times for molecular weight standards are indicated above the chromatograms.

FIG. 21 provides an analytical gel filtration profile of pooled fractions representing WT $E2_{661}$-his peaks 1-4. Individual gel filtration runs on a Superdex 200 PC 3.2/30 column have been overlaid to show their relative elution. Size markers are indicated.

FIG. 22 provides an analytical gel filtration profile of pooled fractions representing of Δ123 $E2_{661}$-his peaks 1-4. Individual gel filtration runs on a Superdex 200 PC 3.2/30 column have been overlaid to show their relative elution. Size markers are indicated.

FIG. 23 provides a reducing SDS-PAGE of peaks 1-4. Three μg of each $E2_{661}$-his protein was added to 10 μl of 4× reducing sample buffer. Samples were heated for 3 min at 70° C. and loaded onto 4-12% Bis-Tris Nu PAGE SDS-PAGE gel. 500 μl of NuPAGE antioxidant was added to the centre component of the gel tank before running at 200V. Migration of BioRad Precision Plus standards is shown on the left.

FIG. 24 provides a non reducing SDS-PAGE of peaks 1-4. Three μg of each $E2_{661}$-his protein was added to 10 μl of 4× non reducing sample buffer. Samples were heated for 3 min at 70° C. and loaded onto 4-12% Bis-Tris NuPAGE SDS-PAGE gel. Migration of BioRad Precision Plus standards is shown on the left.

Figure 25:
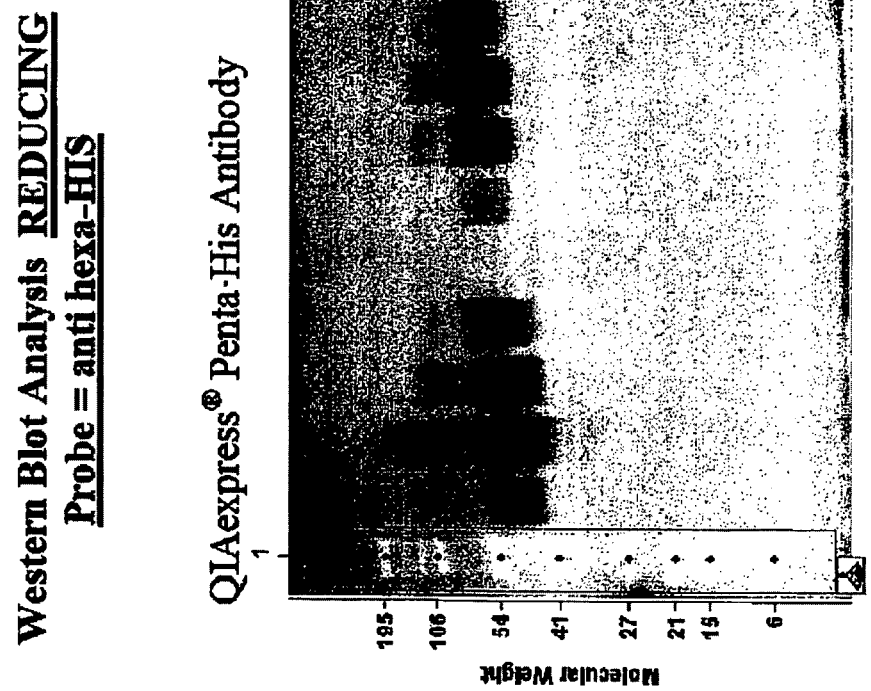

FIG. 25 provides a Western blot analysis of peaks 1-4. 0.5 µg of peaks 1-4 of $E2_{661}$-his was added to 4× reducing sample buffer. Reducing SDS-PAGE analysis was performed as described in FIG. 23. $E2_{661}$-his variants were then transferred to PVDF membrane via wet transfer (1 h). Membranes were blocked overnight with 2% skim milk in PBS. Primary anti Penta-His antibody was added at a dilution of 1:1000 in 0.05% TBS containing 1% skim milk. After 3 washes, sheep anti-mouse IgG HRP (Millipore) was added at a dilution of 1:2000 in 0.05% TBS containing 1% skim milk. After 3 washes, blots were developed with ECL Plus Western Blotting Detection Reagent according to the manufacturer's instructions and scanned at 520 nm. Migration of BioRad Precision Plus standards is shown on the left.

Figure 26:
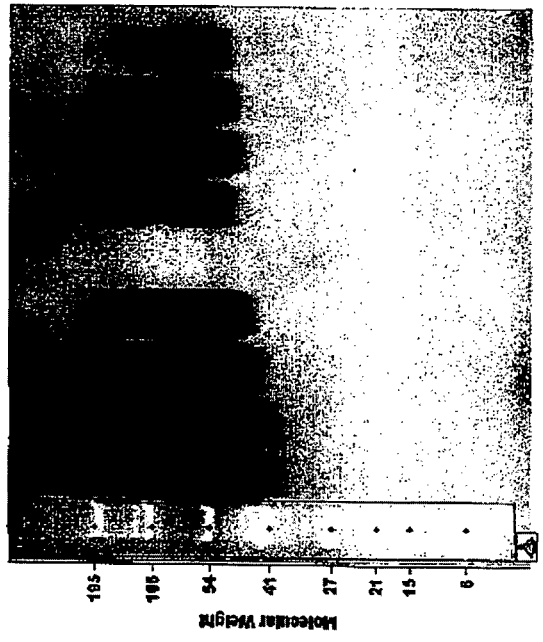

FIG. 26 provides a Western blot analysis of peaks 1-4. 0.5 µg of peaks 1-4 of $E2_{661}$-his was added to 4× reducing sample buffer. Reducing SDS-PAGE analysis was performed as described in FIG. 23. $E2_{661}$-his variants were then transferred to PVDF membrane via wet transfer (1 h). Membranes were blocked overnight with 2% skim milk in PBS. Primary anti-HCV E2 antibody was added at a dilution of 1:1000 in 0.05% TBS containing 1% skim milk. After 3 washes, sheep anti-mouse IgG HRP (Millipore) was added at a dilution of 1:2000 in 0.05% TBS containing 1% skim milk. After 3 washes, blots were developed with ECL Plus Western Blotting Detection Reagent according to the manufacturer's instructions and scanned at 520 nm. Migration of BioRad Precision Plus standards is shown on the left.

Figure 27:
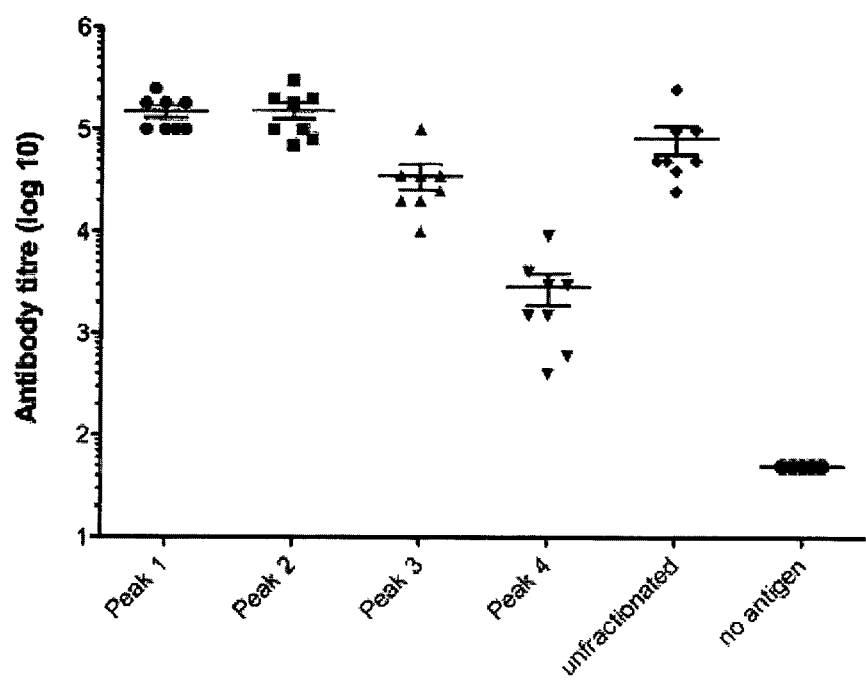

FIG. 27 provides a graphical representation of the reactivity of immune serum obtained from guinea pigs vaccinated with one of WT $E2_{661}$-his peaks 1-4 or the unfractionated mixture to homologous immunizing antigen. Microtitre plates were coated with GNA lectin (0.5 µg/ml) followed by 2 μg/ml of one of peak 1-4 or the unfractionated mixture. Unoccupied sites were blocked with BSA before addition of serial dilutions of immune serum. Bound immunoglobulins were detected with anti-guinea pig immunogloubulins coupled to horse-radish peroxidase and visualised with TMB substrate.

FIG. 28 provides a graphical representation of the reactivity of immune serum obtained from guinea pigs vaccinated with one of Δ123 $E2_{661}$-his protein peaks 1-4 or the unfractionated mixture to homologous immunizing antigen. Microtitre plates were coated with GNA lectin (0.5 μg/ml) followed by 2 μg/ml of one of peak 1-4 or the unfractionated mixture. Unoccupied sites were blocked with BSA before addition of serial dilutions of immune serum. Bound immunoglobulins were detected with anti-guinea pig immunogloubulins coupled to horse-radish peroxidase and visualised with TMB substrate.

FIG. 29 provides a graphical representation of the reactivity of immune serum obtained from guinea pigs vaccinated with one of Δ123 $E2_{661}$-his protein peaks 1-4 or the unfractionated mixture to unfractionated genotype 1a H77c WT and Δ123 $E2_{661}$-his antigens. Microtitre plates were coated with GNA lectin (0.5 μg/ml) followed by 2 μg/ml of the unfractionated H77c WT (A) or Δ123 (B) $E2_{661}$-his antigen. Unoccupied sites were blocked with BSA before addition of serial dilutions of immune serum. Bound immunoglobulins were detected with anti-guinea pig immunogloubulins coupled to horse-radish peroxidase and visualised with TMB substrate.

FIG. 30 provides a graphical representation of the ability of immune serum obtained from guinea pigs vaccinated with one of WT $E2_{661}$-his protein peaks 1-4 or unfractionated mixture to inhibit the binding between homologous (H77c, A) and heterologous (JFH1, B) $E2_{661}$ from binding CD81. Serial dilutions of immune serum were added to 100 ng of unfractionated H77c or JFH1 $E2_{661}$-his protein before addition to MBP-$LEL^{113-201}$ coated enzyme immunoassay plates. Bound $E2_{661}$-his was detected with anti-his antibody, followed by anti-rabbit horse-radish peroxidase conjugated immunoglobulins and TMB substrate. The dilution of antibody required to inhibit 50% of the binding between $E2_{661}$-his and MBP-$LEL^{113-201}$ was calculated for each animal.

FIG. 31 provides a graphical representation of the ability of immune serum obtained from guinea pigs vaccinated with one of Δ123. $E2_{661}$-his protein peaks 1-4 or unfractionated mixture to inhibit the binding between homologous (H77c, A) and heterologous (JFH1, B) $E2_{661}$ from binding CD81. Serial dilutions of immune serum were added to 100 ng of unfractionated H77c or JFH1 $E2_{661}$-his protein before addition to MBP-$LEL^{113-201}$ coated enzyme immunoassay plates. Bound $E2_{661}$-his was detected with anti-his antibody, followed by anti-rabbit horse-radish peroxidase conjugated immunoglobulins and TMB substrate. The dilution of antibody required to inhibit 50% of the binding between $E2_{661}$ and MBP-$LEL^{113-201}$ was calculated for each animal.

FIG. 32 provides a graphical representation of the ability of Δ123 $E2_{661}$-his guinea pig serum to prevent infection of liver cell cultures with homologous HCV. Immune sera elicited by guinea pigs vaccinated with one of Δ123 $E2_{661}$-his protein peaks 1-4 or unfractionated mixture were examined for their ability to neutralize pseudotyped retroviral particles containing the homologous H77c E1E2 glycoproteins (H77c HCVpp). Heat inactivated immune serum was serially diluted in DMF10 and incubated with an equal volume of H77c HCVpp for 1 h at 37° C. before addition to Huh 7.5 cells seeded the day prior at $3\times10^4$ cells/well. After 4 h virus-serum mixtures were removed and replaced with medium. After 3 days, luciferase activity in cell lysates was measured in a luminometer. The IC50 titre was calculated as the dilution of immune serum required to inhibit 50% of viral infection (A) while the IC80 titre is the dilution of serum required to inhibit 80% of viral infection (B).

FIG. 33 provides a graphical representation of the ability of Δ123 $E2_{661}$-his guinea pig serum to prevent infection of liver cell cultures with a heterologous strain of HCV. Immune sera elicited by guinea pigs vaccinated with one of Δ123 $E2_{661}$-his protein peaks 1-4 or unfractionated mixture were examined for their ability to neutralize J6/JFH1 chimeric cell culture (HCVcc) genotype 2a virus. Heat inactivated immune serum was serially diluted in DMF10+NEAA and mixed with an equal volume of 3.16 $TCID_{50}$/ml HCVcc for 20 min at 37° C. Serum/virus mixtures were applied to Huh 7.5 cells seeded the day prior at $8\times10^3$ cells/well and incubated for 5 h at 37° C. Serum/virus mixtures were removed and washed 4 times with PBS before addition of DMF10+NEAA and incubation for 44 h. Luciferase activity present in the tissue culture fluid was measured using the *Renilla* luciferase substrate and a luminometer. The IC50 titre was calculated as the dilution of immune serum required to inhibit 50% of viral replication (A) while the IC80 titre is the dilution of serum required to inhibit 80% of viral replication (B).

FIG. 34 provides a graphical representation of the reactivity of WT $E2_{661}$-his immune serum to unfractionated H77c WT and Δ123 $E2_{661}$-his antigens in an enzyme immunoassay. Microtitre plates were coated GNA lectin (0.5 μg/ml) followed by 2 μg/ml of the unfractionated H77c WT (A) or Δ123 (B) $E2_{661}$-his antigen. Unoccupied sites were blocked with BSA before addition of serial dilutions of immune serum. Bound immunoglobulins were detected with anti-guinea pig immunogloubulins coupled to horse-radish peroxidase and visualised with TMB substrate.

Figure 35:
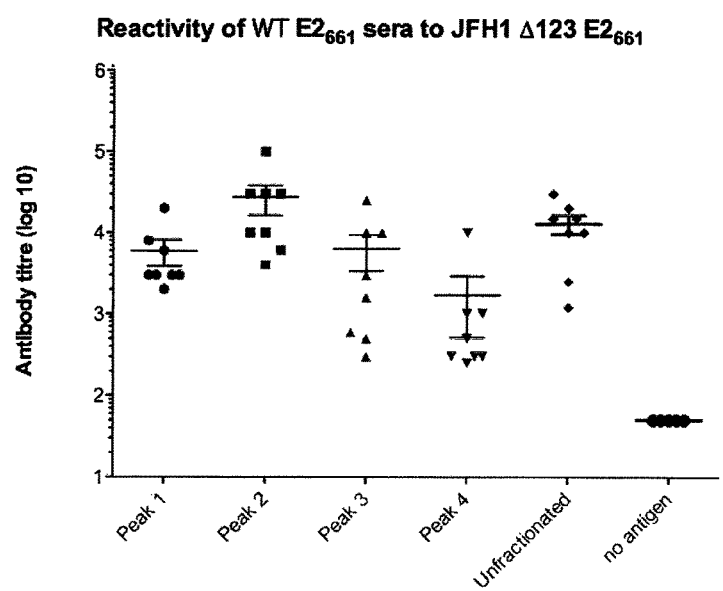

FIG. 35 provides a graphical representation of the reactivity immune serum obtained from guinea pigs vaccinated with one of H77c WT peak 1-4 $E2_{661}$-his proteins or the unfractionated $E2_{661}$-his mixture to heterologous JFH1 WT and Δ123 $E2_{661}$-his antigens in an enzyme immunoassay. Microtitre plates were coated GNA lectin (0.5 μg/ml) followed by 2 μg/ml of the unfractionated JFH1 WT (A) or Δ123 (B) $E2_{661}$-his antigen. Unoccupied sites were blocked with BSA before addition of serial dilutions of immune serum. Bound immunoglobulins were detected with anti-guinea pig immunogloubulins coupled to horse-radish peroxidase and visualised with TMB substrate.

FIG. 36 provides a graphical representation of the ability of wild-type $E2_{661}$-his guinea pig serum to prevent infection of liver cell cultures with homologous HCV. Immune sera elicited by guinea pigs vaccinated with one of WT $E2_{661}$-his peaks 1-4 proteins or unfractionated mixture were examined for their ability to neutralize pseudotyped retroviral particles containing the homologous H77c E1E2 glycoproteins (H77c HCVpp). Heat inactivated immune serum was serially diluted in DMF10 and incubated with an equal volume of H77c HCVpp for 1 h at 37° C. before addition to Huh 7.5 cells seeded the day prior at $3 \times 10^4$ cells/well. After 4 h virus-serum mixtures were removed and replaced with medium. After 3 days, luciferase activity in cell lysates was measured in a luminometer. The IC50 titre was calculated as the dilution of immune serum required to inhibit 50% of viral infection (A) while the IC80 titre is the dilution of serum required to inhibit 80% of viral infection (B).

FIG. 37 provides a graphical representation of the ability of WT $E2_{661}$-his immune serum to prevent infection of liver cell cultures with a heterologous strain of HCV. Immune sera elicited by guinea pigs vaccinated with one of WT $E2_{661}$-his peaks 1-4 proteins or unfractionated mixture were examined for their ability to neutralize J6/JFH1 chimeric cell culture (HCVcc) genotype 2a virus. Heat inactivated immune serum was serially diluted in DMF10+NEAA and mixed with an equal volume of 3.16 $TCID_{50}$/ml HCVcc for 20 min at 37° C. Serum/virus mixtures were applied to Huh 7.5 cells seeded the day prior at $8 \times 10^3$ cells/well and incubated for 5 h at 37° C. Serum/virus mixtures were removed and washed 4 times with PBS before addition of DMF10+NEAA and incubation for 40 h. Luciferase activity present in the tissue culture fluid was measured using the *Renilla* luciferase substrate and a luminometer. The IC50 titre was calculated as the dilution of immune serum required to inhibit 50% of viral replication (A) while the IC80 titre is the dilution of serum required to inhibit 80% of viral replication (B).

FIG. 38 provides a graphical representation of the reactivity of WT $E2_{661}$-his immune serum to heterologous Con1 (genotype 1b) wild-type and Δ123 $E2_{661}$-his antigens in an enzyme immunoassay. Microtitre plates were coated GNA lectin (0.5 μg/ml) followed by 2 μg/ml of the unfractionated Con1 WT (A) or Δ123 (B) $E2_{661}$-his mixture. Unoccupied sites were blocked with BSA before addition of serial dilutions of immune serum. Bound immunoglobulins were detected with anti-guinea pig immunogloubulins coupled to horse-radish peroxidase and visualised with TMB substrate.

FIG. 39 provides a graphical representation of the reactivity of Δ123 $E2_{661}$-his immune serum to heterologous Con1 (genotype 1b) WT and Δ123 $E2_{661}$-his antigens in an enzyme immunoassay. Microtitre plates were coated GNA lectin (0.5 μg/ml) followed by 2 μg/ml of the unfractionated Con1 WT (A) or Δ123 (B) $E2_{661}$-his mixture. Unoccupied sites were blocked with BSA before addition of serial dilutions of immune serum. Bound immunoglobulins were detected with anti-guinea pig immunogloubulins coupled to horse-radish peroxidase and visualised with TMB substrate.

FIG. 40 provides a graphical representation of the reactivity of Δ123 $E2_{661}$-his immune serum to heterologous JFH1 (genotype 2a) WT and Δ123 $E2_{661}$-his antigens in an enzyme immunoassay. Microtitre plates were coated GNA lectin (0.5 μg/ml) followed by 2 μg/ml of the unfractionated JFH1 WT (A) or Δ123 (B) $E2_{661}$-his mixture. Unoccupied sites were blocked with BSA before addition of serial dilutions of immune serum. Bound immunoglobulins were detected with anti-guinea pig immunogloubulins coupled to horse-radish peroxidase and visualised with TMB substrate.

Table 1 lists guinea pigs vaccine recipient groups (1 to 7) and the antigen type, antigen amount, adjuvant and number of subjects in each group receiving same as described in Example 3.

DETAILED DISCUSSION OF EMBODIMENTS

The subject invention is not limited to particular screening procedures for agents, specific formulations of agents and various medical methodologies, as such may vary.

Unless defined otherwise, all technical and scientific terms used herein have the same meanings as commonly understood by one of ordinary skill in the art to which this invention belongs. Any materials and methods similar or equivalent to those described herein can be used to practice or test the present invention. Practitioners are particularly directed to Sambrook et al., 1989 (supra), Coligan et al. *Current Protocols In Protein Science*, John Wiley & Sons, Inc., 1995-1997, in particular Chapters 1, 5 and 6, and Ausubel et al., *Current Protocols in Molecular Biology*, Supplement 47, John Wiley & Sons, New York, 1999; Colowick and Kaplan, eds., *Methods In Enzymology*, Academic Press, Inc.; Weir and Blackwell, eds., *Handbook of Experimental Immunology, Vols. I-IV*, Blackwell Scientific Publications, 1986; Joklik ed., *Virology, 3rd Edition,* 1988; Fields and Knipe, eds, *Fundamental Virology, 2nd Edition,* 1991; Fields et al., eds, *Virology, 3rd Edition*, Lippincott-Raven, Philadelphia, Pa., 1996, for definitions and terms of the art and other methods known to the person skilled in the art.

The present invention provides a composition comprising hepatitis C virus (HCV) Envelope 2 (E2) glycoprotein, wherein the HCV E2 glycoprotein is substantially depleted of HCV E2 monomers. As used herein the phrases "substantially depleted of E2 monomers" or "substantially monomer depleted HCV E2" refers to a composition comprising less than 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% or less than 1% E2 monomers (by weight).

The term "HCV E2 glycoprotein", "E2 glycoprotein", "E2 dimers", "E2 trimers" or "E2", "E2 monomer, "HCV E2" and the like includes an E2 glycoprotein from any genotype or isolate of HCV. The term further includes non-naturally occurring variants including portions of the full length E2 glycoprotein including those that, for example, mediate receptor binding, or mediate neutralizing antibody binding by one or more antibodies that recognize conformational and/or other epitopes, or those portions that mediate E1E2 dimer formation.

In some embodiments, the proportion of HCV E2 that is in monomeric form is less than 15%, 14%, 13%, 12%, 11%, 10%, 9%, 8%, 7%, 6%, 5%, 4%, 3%, 2%, 1%, 0.5% or 0.1% by weight.

The substantially monomer depleted HCV E2 glycoprotein may be a glycoprotein produced by recombinant or synthetic means.

In a particular embodiment, the compositions are substantially free of monomeric HCV E2 having less than 1% or less than 0.1% monomeric HCV E2.

In a further aspect, the substantially monomer depleted HCV E2 composition is enriched for trimeric and higher order forms of HCV E2 and includes preparations of the composition having more than 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% (by weight) trimeric and higher order form HCV E2 glycoproteins.

As used herein, the phrase "higher order forms" of HCV E2 glycoprotein refers to forms of the E2 protein having four or more E2 protein subunits. Such forms are known as Tetramer (4), pentamer (5), hexamer (6), heptamer (7), octamer (8), nonamer (9), decamer (10), undecamer (11), dodecamer (12), tridecamer (13), tetradecamer (14), pentadecamer (15), hexadecamer (16), heptadecamer (17), octadecamer (18), nonadecamer (19), eicosamer (20), 21-mer, 22-mer, 23-mer etc.

In a related aspect, the substantially monomer depleted HCV E2 composition is enriched for trimeric HCV E2 and includes preparations of the composition having more than 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% (by weight) trimeric HCV E2 glycoprotein.

In another aspect, the substantially monomer depleted HCV E2 composition is enriched for dimeric HCV E2 and includes preparations of the composition having more than 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% (by weight) dimeric HCV E2 glycoprotein.

In another aspect composition comprises substantially HCV E2 trimers. In a further aspect, the composition comprises substantially HCV E2 trimers and higher order forms. In yet a further aspect the composition comprises substantially higher order forms of HCV E2.

A composition that comprises substantially trimeric HCV E2 includes preparations of the composition having more than 80%, 81%, 82%, 83%, 84%, 85%, 86%, 87%, 88%, 89%, 90%, 91%, 92%, 93%, 94%, 95%, 96%, 97%, 98%, or 99% (by weight) E2 trimers.

A composition that comprises substantially trimeric and higher order forms of HCV E2 includes preparations of the composition having more than 80%, 81%, 82%, 83%, 84%, 85%, 86%, 87%, 88%, 89%, 90%, 91%, 92%, 93%, 94%, 95%, 96%, 97%, 98%, or 99% (by weight) E2 trimers and higher order forms.

A composition that comprises substantially higher order forms of HCV E2 includes preparations of the composition having more than 80%, 81%, 82%, 83%, 84%, 85%, 86%, 87%, 88%, 89%, 90%, 91%, 92%, 93%, 94%, 95%, 96%, 97%, 98%, or 99% (by weight) higher order forms of E2.

Methods for determining the percentages by weight or proportions of each of the E2 monomer, dimer and trimer and higher order forms in a preparation are described or known to those of skill in the art.

In one embodiment, the E2 glycoprotein is substantially HCV E2 trimers or higher order forms.

A composition that comprises trimeric and higher order forms of HCV E2 includes preparations of the composition having more than about 80%, 81%, 82%, 83%, 84%, 85%, 86%, 87%, 88%, 89%, 90%, 91%, 92%, 93%, 94%, 95%, 96%, 97%, 98%, or 99% (by weight) E2 trimers and higher order forms.

In some embodiments, the E2 glycoprotein is substantially HCV E2 trimers.

A composition that comprises substantially trimeric HCV E2 includes preparations of the composition having more than about 80%, 81%, 82%, 83%, 84%, 85%, 86%, 87%, 88%, 89%, 90%, 91%, 92%, 93%, 94%, 95%, 96%, 97%, 98%, or 99% (by weight) E2 trimers.

In some embodiments, the E2 glycoprotein is substantially HCV E2 dimers.

A composition that comprises substantially dimeric HCV E2 includes preparations of the composition having more than about 80%, 81%, 82%, 83%, 84%, 85%, 86%, 87%, 88%, 89%, 90%, 91%, 92%, 93%, 94%, 95%, 96%, 97%, 98%, or 99% (by weight) E2 dimers.

In some embodiments, the E2 glycoprotein is substantially HCV E2 dimers and E2 trimers. A composition that comprises HCV E2 in substantially dimeric and trimeric forms includes a preparation having more than 70%, 75%, 80% 85%, 90%, 95%, 97%, or 99% (by weight) E2 dimers and trimers, and/or a preparation having less than 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% or less than 1% E2 monomers (by weight).

In some embodiments, the compositions of this invention may be obtained by depleting monomers from mixtures of HCV E2 glycoproteins or by enriching for dimeric and/or trimeric E2 and/or higher order forms. In some embodiments, monomers are depleted and/or dimers and/or trimers and/or higher order forms are enriched.

In another embodiment, the substantially monomer depleted HCV E2 composition further comprises a pharmaceutically or physiologically acceptable carrier or diluent.

In a further embodiment, the substantially monomer depleted composition further comprises an adjuvant. Subject responses to immunogens can be enhanced if administered as a mixture with one or more adjuvants. Immune adjuvants typically function in one or more of the following ways: (1) immunomodulation (2) enhanced presentation (3) CTL production (4) targeting; and/or (5) depot generation. Illustrative adjuvants include: particulate or non-particulate adjuvants, complete Freund's adjuvant (CFA), aluminum salts, emulsions, ISCOMS, LPS derivatives such as MPL and derivatives thereof such as 3D, mycobacterial derived proteins such as muramyl di- or tri-peptides, particular saponins from *Quillaja saponaria*, such as QS21 and ISCOPREP™ saponin, ISCOMATRIX™ adjuvant, and peptides, such as thymosin alpha 1. An extensive description of adjuvants can be found in Cox and Coulter, "Advances in Adjuvant Technology and Application", in *Animal Parasite Control Utilizing Biotechnology*, Chapter 4, Ed. Young, W. K., CRC Press 1992, and in Cox and Coulter, *Vaccine* 15(3): 248-256, 1997.

Pharmaceutical compositions are conveniently prepared according to conventional pharmaceutical compounding techniques. See, for example, Remington's Pharmaceutical Sciences, 18th Ed., Mack Publishing, Company, Easton, Pa., U.S.A., 1990. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g. intravenous, oral or parenteral.

One illustrative form of HCV E2 glycoprotein is a receptor binding portion of E2 glycoprotein comprising amino acids 384-661 of genotype H771a ($E2_{661}$) or a corresponding portion from another HCV genotype.

In some embodiments, HCV E2 glycoprotein comprises an amino acid sequence or structure substantially similar to a naturally occurring variant of HCV. For example, E2 proteins may be substantially similar to the amino acid sequences of one or more isolates known in the art such as JFH-1, Con1, H77c or ED43 isolates, or they may be substantially similar to one or more of the E2 glycoproteins expressed by one of genotypes 1 to 6, or a fragment thereof.

In other embodiments, the HCV E2 glycoprotein is a variant of a naturally occurring HCV E2 glycoprotein that binds a host cell receptor and/or comprises one or more epitopes recognized by neutralizing or conformational epitopes. One form of variant is a truncated form or fragment of a naturally occurring strain or its inculture variants. Illustrative fragments include the receptor binding domain. Other modified HCV E2 glycoproteins include mutants, analogs or derivatives.

Alternatively or in addition, in some embodiments, the HCV E2 glycoprotein comprises a mutation, such as a deletion mutation, in one or more variable regions. Illustrative mutants are disclosed in International Publication No. WO 2008/022401 incorporated herein in its entirety by reference. As determined herein, E2 glycoprotein comprising or lacking the three variable regions are able to form functional receptor binding dimers and/or trimers and inhibit virus entry into permissive host cells.

In one embodiment, the E2 protein is $E2_{661}\Delta 123$ ($\Delta HVR123$, also referred to herein as $\Delta 123$, D123, $\Delta HVR1+2+3$, D123 $E2_{661}$-his, D123 $E2_{661}$, $\Delta 123$ $E2_{661}$ and $\Delta 123$ $E2_{661}$-his). In some embodiments, the $E2_{661}\Delta 123$ E2 comprises amino acids 384-661 of HCV H77c where the variable regions 1 and 2 and igVR (3) are replaced with short linker motifs ($\Delta HVR123$). Other embodiments of the invention include a HCV E2 protein having any combination of HVR1, HVR2 or igVR deleted or replaced by a short linker. These can be abbreviated as $\Delta 1$; $\Delta 1,2$ ($\Delta 12$); $\Delta 2$; $\Delta 2,3$ ($\Delta 23$); $\Delta 3$; and $\Delta 1,3$ ($\Delta 13$).

The present invention further provides a method for eliciting an immune response in a subject or patient, the method comprising administering to the subject or patient an effective amount of a composition comprising substantially monomer depleted HCV E2. A composition, particularly a vaccine composition for immunizing a subject against infection from hepatitis C virus comprising substantially monomer depleted HCV E2 is also contemplated by the present invention.

The term "vaccine" as used herein refers to a pharmaceutical composition comprising at least one immunologically active component that induces an immunological response in a subject and possibly but not necessarily one or more additional components that enhance the immunological activity of said active component (for example an adjuvant). A vaccine may additionally comprise further components typical to pharmaceutical compositions. The immunologically active component of a vaccine comprises a substantially monomer depleted HCV E2 composition.

The terms "vaccine" and "vaccine composition" are used interchangeably in the present invention.

"Subjects" contemplated in the present invention are humans or animals including laboratory or art accepted test or vehicle animals. "Patients" include human subjects in need of treatment or prophylaxis.

In some embodiments, a composition, particularly a vaccine composition for immunizing a subject against HCV infection is contemplated, comprising substantially dimeric, or substantially trimeric HCV E2 or a mixture of dimeric and trimeric HCV E2 glycoprotein or a mixture of trimeric and higher order forms of HCV E2 or a mixture of dimeric, trimeric and higher order forms of HCV E2 or higher order forms of HCV E2.

In another aspect, the present invention provides a composition comprising HCV E2 glycoprotein in substantially dimeric or trimeric and/or higher order form for use in producing an antibody and/or cellular immune response in a human or non-human animal subject.

Recombinant HCV E2 glycoproteins expressed by eukaryotic cells are generally present as mixtures of monomers, dimers, trimers and higher order forms.

HCV E2 may be expressed in eukaryotic or prokaryotic cells. Eukaryotic cells include mammalian, plant, yeast and insect cells as known in the art. Recombinant proteins are produced by culturing the host cells for a period of time sufficient to allow for expression of the protein in the host cells or, more preferably, secretion of the protein into the culture medium in which the host cells are grown.

"Recombinant host cells", "host cells", "cells", "cell lines", "cell cultures", and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transfected.

Suitable mammalian cell lines include, but are not limited to, BHK, VERO, HT1080, 293, 293T, 293F, RD, COS-7, CHO, Jurkat, HUT, SUPT, C8166, MOLT4/clone8, MT-2, MT-4, H9, PML, CEM, myeloma cells (e.g., SB20 cells) and CEMX174 are available, for example, from the ATCC. Other host cells include without limitation yeast, e.g. *Pichia pastoris*, or insect cells such as Sf9 cells.

Synthetic DNA may be recombinantly expressed by molecular cloning into an expression vector containing a suitable promoter and other appropriate transcription regulatory elements, and transferred into prokaryotic or eukaryotic host cells to produce recombinant protein. Techniques for such manipulations are described by Sambrook et al., *Molecular Cloning: A Laboratory Manual* (2nd ed.). Cold Spring Harbour Laboratory, Cold Spring Harbour, N.Y., 1989; Ausubel et al., Current Protocols in Molecular Biology, Green Pub. Associates and Wiley-Interscience, New York, 1988.

For example, a construct for expression in yeast preferably contains a synthetic gene, with related transcriptional and translational control sequences operatively linked to it, such as a promoter (such as GAL10, GAL7, ADH1, TDH3 or PGK), and termination sequences (such as the *S. cerevisiae* ADH1 terminator). The yeast may be selected from the group consisting of: *Saccharomyces cerevisiae, Hansenula polymorpha, Pichia pastoris, Kluyveromyces fragilis, Kluyveromyces lactis*, and *Schizosaccharomyces pombe*. See also Yeast Genetics: Rose et al., A Laboratory Course Manual, Cold Spring Harbor Laboratory, Cold Spring Harbor, N.Y., 1990. Nucleic acid molecules can be codon optimized for expression in yeast as known in the art (see Sharp and Cowe, *Yeast,* 7: 657-678, 1991). Appropriate vectors and control elements for any given cell type can be selected by one having ordinary skill in the art in view of the teachings of the present specification and information known in the art about expression vectors.

Vectors available for cloning and expression in host cell lines are well known in the art, and include but are not limited to vectors for cloning and expression in mammalian cell lines or yeast (fungal) cells, vectors for cloning and expression in bacterial cell lines, vectors for cloning and expression in phage and vectors for cloning and expression in insect cell lines. The expressed proteins can be recovered using standard protein purification methods.

Translational control elements have been reviewed by M. Kozak (e.g., Kozak, *Mamm Genome,* 7(8): 563-74, 1996; Kozak, *Biochimie.,* 76(9): 815-21, 1994; Kozak, *J Cell Biol,* 108(2): 229-241, 1989; Kozak and Shatkin, *Methods Enzymol,* 60: 360-375, 1979).

Recombinant glycoproteins can be conveniently prepared using standard protocols as described for example in Sambrook, et al., 1989 (supra), in particular Sections 13, 16 and 17; Ausubel et al., Current Protocols in Molecular Biology, John Wiley & Sons Inc, 1994, in particular Chapters 10 and 16; and Coligan et al., 1995-1997 (supra), in particular Chapters 1, 5 and 6. The polypeptides or polynucleotides may be synthesized by chemical synthesis, e.g., using solution synthesis or solid phase synthesis as described, for example, in Chapter 9 of Atherton and Shephard, Peptide Synthesis. In Nicholson ed., Synthetic Vaccines, published by Blackwell Scientific Publications, and in Roberge et al., *Science,* 269(5221): 202-204, 1995.

The present invention also provides a method for immunizing a subject against infection from hepatitis C virus comprising administering to the subject a composition comprising substantially monomer depleted HCV E2.

In a related embodiment, the invention also provides a method for treating hepatitis C infection in a subject, comprising administering to the subject a composition comprising substantially monomer depleted HCV E2.

The present invention further provides a method of eliciting a humoral or cell mediated immune response in a subject or patient, the method comprising administering to the subject or patient an effective amount of a composition comprising substantially monomer depleted HCV E2.

In accordance with these embodiments, the composition is generally administered for a time and under conditions sufficient to elicit an immune response comprising the generation of E2-specific antibodies. The compositions of the present invention may be administered as a single dose or application. Alternatively, the compositions may involve repeat doses or applications, for example the compositions may be administered 2, 3, 4, 5, 6, 7, 8, 9, 10 or more times.

An example of a vaccination regimen contemplated by the present invention is as follows: Following an initial vaccination, subjects typically receive a boost after a 2 to 4 week interval, for example a 3 week interval, optionally followed by repeated boosts. In a specific embodiment of the invention, a single-dose vaccination schedule is provided, whereby one dose of the composition is sufficient to provide protection against hepatitis C, without the need for any boost after the initial vaccination.

In some embodiments, antibodies generated against substantially monomer depleted HCV E2 include those that at least partially neutralize an important part of the HCV life cycle such as host cell invasion or viral budding.

The present invention is further directed to the use of substantially monomer depleted HCV E2 in, or in the manufacture of a medicament for, the treatment or prevention of HCV infection. Humanized and deimmunized antibodies are also encompassed by the present invention. The term "manufacture" includes production or screening.

In another embodiment, the present invention provides a method of eliciting a humoral or cell-mediated immune response in a subject or patient, the method comprising administering to the subject an effective amount of a composition comprising substantially dimeric and/or trimeric and/or higher order form HCV E2 glycoprotein.

In a related embodiment, the present invention provides a method for treating hepatitis C infection in a subject or for immunizing a subject against hepatitis C infection comprising administering to the subject an effective amount of a composition comprising substantially dimeric and/or trimeric and/or higher order form HCV E2 glycoprotein.

In some embodiments, the present invention provides a method of selecting therapeutic antibodies or other therapeutic binding agents comprising selecting antibodies or agents that (i) bind to one or more dimeric or trimeric or higher order form HCV E2 forms, and/or (ii) that do not bind to monomeric HCV E2.

The terms "effective amount" including "therapeutically effective amount" and "prophylactically effective amount" as used herein mean a sufficient amount of a composition of the present invention either in a single dose or as part of a series or slow release system which provides the desired therapeutic, preventative, or physiological effect in some subjects. Undesirable effects, e.g. side effects, may sometimes manifest along with the desired therapeutic effect; hence, a practitioner balances the potential benefits against the potential risks in determining an appropriate "effective amount". The exact amount of composition required will vary from subject to subject, depending on the species, age and general condition of the subject, mode of administration and the like. Thus, it may not be possible to specify an exact 'effective amount'. However, an appropriate 'effective amount' in any individual case may be determined by one of ordinary skill in the art using routine skills or experimentation. One of ordinary skill in the art would be able to determine the required amounts based on such factors as prior administration of the compositions or other agents, the subject's size, the severity of a subject's symptoms or the severity of symptoms in an infected population, viral load, and the particular composition or route of administration selected.

The term "treatment" refers to any measurable or statistically significant amelioration in at least some subjects in one or more symptoms of HCV or in the risk of developing advanced symptoms of HCV or the risk of transmitting HCV.

The terms "prevention" and "prophylaxis" and the like are used interchangeably and include administration of a composition of the present invention to a subject not known to be infected with HCV for the purpose of prevention or attenuating a subsequent infection or reducing the risk of becoming infected or reducing the severity or onset of a condition or signs of a condition associated with HCV infection.

The administration of the vaccine composition is generally for prophylactic purposes. The prophylactic administration of the composition serves to prevent or attenuate any subsequent infection. A "pharmacologically acceptable" composition is one tolerated by a recipient patient. It is contemplated that an effective amount of the vaccine is administered. An "effective amount" is an amount sufficient to achieve a desired biological effect such as to induce enough humoral or cellular immunity. This may be dependent upon the type of vaccine, the age, sex, health, and weight of the recipient. Examples of desired biological effects include, but are not limited to, production of no symptoms, reduction in symptoms, reduction in virus titer in tissues or nasal secretions, complete protection against infection by hepatitis C virus, and partial protection against infection by hepatitis C virus.

In some embodiments, a vaccine or composition of the present invention is physiologically significant if its presence results in a detectable change in the physiology of a recipient patient that enhances or indicates an enhancement in at least one primary or secondary humoral or cellular immune response against at least one strain of an infectious hepatitis C virus. The vaccine composition is administered to protect against viral infection. The "protection" need not be absolute, i.e., the hepatitis C infection need not be totally prevented or eradicated, if there is a statistically significant improvement compared with a control population or set of patients. Protection may be limited to reducing the severity or rapidity of onset of symptoms of the hepatitis C virus infection.

In one embodiment, a vaccine composition of the present invention is provided to a subject either before the onset of infection (so as to prevent or attenuate an anticipated infection) or after the initiation of an infection, and thereby protects against viral infection. In some embodiments, a vaccine composition of the present invention is provided to a subject before or after onset of infection, to reduce viral transmission between subjects.

It will be further appreciated that compositions of the present invention can be administered as the sole active pharmaceutical agent, or used in combination with one or more agents to treat or prevent hepatitis C infections or symptoms associated with HCV infection. Other agents to be administered in combination with a composition or a combination of compositions of the present invention include therapies for disease caused by HCV infection or that suppress HCV viral replication by direct or indirect mechanisms. These agents include, but are not limited to, host immune modulators (for example, interferon-alpha, pegylated interferon-alpha, consensus interferon, interferon-beta, interferon-gamma, CpG oligonucleotides and the like); antiviral compounds that inhibit host cellular functions such as inosine monophosphate dehydrogenase (for example, ribavirin and the like); cytokines that modulate immune function (for example, interleukin 2, interleukin 6, and interleukin 12); a compound that enhances the development of type 1 helper T cell response; interfering RNA; anti-sense RNA; vaccines comprising HCV antigens or antigen adjuvant combinations directed against HCV; agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like; and any agent or combination of agents that inhibit the replication of HCV by targeting other proteins of the viral genome involved in the viral replication and/or interfere with the function of other viral targets, such as inhibitors of NS3/NS4A protease, NS3 helicase, NS5B polymerase, NS4A protein and NS5A protein.

According to yet another embodiment, the pharmaceutical compositions of the present invention may further comprise other inhibitor(s) of targets in the HCV life cycle, including, but not limited to, helicase, polymerase, metalloprotease, NS4A protein, NS5A protein, and internal ribosome entry site (IRES).

Administration is generally for a time and under conditions sufficient to elicit an immune response comprising the generation of E2-specific antibodies or cellular immune response. The immunogenic compositions may be administered in a convenient manner such as by the pulmonary, oral, intravenous (where water soluble), intraperitoneal, intramuscular, subcutaneous, intradermal, intrathecal or suppository routes or implanting (e.g. using slow release, formulations). Administration may be systemic or local, although systemic is more convenient. Other contemplated routes of administration are by patch, cellular transfer, implant, sublingually, intraocularly, topically, orally, rectally, vaginally, nasally or transdermally.

As used herein, an "immune response" refers to the reaction of the body as a whole to the presence of a composition of the present invention which includes making antibodies and developing immunity to the composition. Therefore, an immune response to an antigen also includes the development in a subject of a humoral and/or cellular immune response to the antigen of interest. A "humoral immune response" is mediated by antibodies' produced by plasma cells. A "cellular immune response" is one mediated by T lymphocytes and/or other white blood cells.

As used herein, "antibody titers" can be defined as the highest dilution in post-immune sera that resulted in a value greater than that of pre-immune samples for each subject.

Embodiments of the present invention also provide assays for assessing an immune response to the components isolated from the substantially monomer depleted HCV E2. The assays may comprise in vivo assays, such as assays to measure antibody responses and delayed type hypersensitivity responses. In an embodiment, the assay to measure antibody responses primarily may measure B-cell function as well as B-cell/T-cell interactions. For the antibody response assay, antibody titers in the blood may be compared following an antigenic challenge. These levels can be quantitated according to the type of antibody, as for example, IgG, IgG1, IgG2, IgG3, IgG4, IgM, IgA or IgD. Also, the development of immune systems may be assessed by determining levels of antibodies and lymphocytes in the blood without antigenic stimulation.

The assays may also comprise in vitro assays. The in vitro assays may comprise determining the ability of cells to divide, or to provide help for other cells to divide, or to release lymophokines and other factors, express markers of activation, and lyse target cells. Lymphocytes in mice and man can be compared in in vitro assays. In an embodiment, the lymphocytes from similar sources such as peripheral blood cells, splenocytes, or lymph node cells, are compared. It is possible, however, to compare lymphocytes from different sources as in the non-limiting example of peripheral blood cells in humans and splenocytes in mice. For the in vitro assay, cells may be purified (e.g., B-cells, T-cells, and macrophages) or left in their natural state (e.g., splenocytes or lymph node cells). Purification may be by any method that gives the desired results. The cells can be tested in vitro for their ability to proliferate using mitogens or specific antigens. The ability of cells to divide in the presence of specific antigens can be determined using a mixed lymphocyte reaction (MLR) assay. Supernatant from the cultured cells can be tested to quantitate the ability of the cells to secrete specific lymphokines. The cells can be removed from culture and tested for their ability to express activation antigens. This can be done by any method that is suitable as in the non-limiting example of using antibodies or ligands which bind to the activation antigen as well as probes that bind the RNA coding for the activation antigen.

Also, in an embodiment, phenotypic cell assays can be performed to determine the frequency of certain cell types. Peripheral blood cell counts may be performed to determine the number of lymphocytes or macrophages in the blood. Antibodies can be used to screen peripheral blood lymphocytes to determine the percent of cells expressing a certain antigen as in the non-limiting example of determining CD4 cell counts and CD4/CD8 ratios.

In accordance with these embodiments, the composition is generally administered for a time and under conditions sufficient to elicit an immune response comprising the generation of E2-specific antibodies or cellular immune response. The compositions of the present invention may be administered as a single dose or application. Alternatively, the compositions may involve repeat doses or applications, for example the compositions may be administered 2, 3, 4, 5, 6, 7, 8, 9, 10 or more times.

In a further embodiment, the present invention provides a method for producing an antibody against the substantially monomer depleted HCV E2 composition, comprising injecting into a subject an immunologically effective amount of the substantially monomer depleted HCV E2 composition, and isolating and purifying the antibody produced. In another embodiment, the present invention provides purified antibodies raised against substantially monomer depleted HCV E2.

In another embodiment, the present invention provides antibodies raised against substantially monomer depleted forms of HCV E2. In some embodiments, antibodies are specific for epitopes present in trimeric or dimeric or higher order forms, or trimeric and dimeric forms of HCV E2 glycoprotein or trimeric and higher order forms of HCV E2 glycoprotein and are capable of distinguishing between monomeric, dimeric, trimeric and higher order forms of HCV E2 or between monomeric and dimeric/trimeric forms of HCV E2.

Antibodies may be polyclonal or monoclonal. Further, antibodies may be selected for diagnostic, prognostic, therapeutic, prophylactic, and screening purposes typically using criteria known to those of skill in the relevant art.

The terms "antibody" and "antibodies" include polyclonal and monoclonal antibodies and all the various forms derived from monoclonal antibodies, including but not limited to full-length antibodies (e.g. having an intact Fc region), antigen-binding fragments, including for example, Fv, Fab, Fab' and F(ab')$_2$ fragments; and antibody-derived polypeptides produced using recombinant methods such as single chain antibodies. The terms "antibody" and "antibodies" as used herein also refer to human antibodies produced for example in transgenic animals or through phage display, as well as antibodies, human or humanized antibodies, primatized antibodies or deimmunized antibodies. It also includes other forms of antibodies that may be therapeutically acceptable and antigen-binding fragments thereof, for example single domain antibodies derived from cartilagenous marine animals or Camelidae, or from libraries based on such antibodies. The selection of fragmented or modified forms of the antibodies may also involve consideration of any affect the fragments or modified forms have on the half-lives of the antibody or fragment.

In some embodiments, the antibody is provided with a pharmaceutically or pharmacologically acceptable carrier, diluent or excipient.

In other embodiments, the antibody is selected for diagnosis or prognosis. In some embodiments, kits comprising anti-trimer or anti-dimer or anti-higher order forms of HCV E2 glycoprotein antibodies are provided.

A "pharmaceutically acceptable carrier and/or a diluent" is a pharmaceutical vehicle comprised of a material that is not otherwise undesirable i.e., it is unlikely to cause a substantial adverse reaction by itself or with the active composition. Carriers may include all solvents, dispersion media, coatings, antibacterial and antifungal agents, agents for adjusting tonicity, increasing or decreasing absorption or clearance rates, buffers for maintaining pH, chelating agents, membrane or barrier crossing agents. A pharmaceutically acceptable salt is a salt that is not otherwise undesirable. The agent or composition comprising the agent may be administered in the form of pharmaceutically acceptable non-toxic salts, such as acid addition salts or metal complexes.

For oral administration, the compositions can be formulated into solid or liquid preparations such as capsules, pills, tablets, lozenges, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. Tablets may contain a binder such as tragacanth, corn starch or gelatin; a disintegrating agent, such as alginic acid; and a lubricant, such as magnesium stearate. If desired, tablets may be sugar-coated or enteric-coated by standard techniques. The active composition can be encapsulated to make it stable to passage through the gastrointestinal tract. See for example, International Patent Publication No. WO 96/11698.

For parenteral administration, the composition may be dissolved in a carrier and administered as a solution or a suspension. For transmucosal or transdermal (including patch) delivery, appropriate penetrants known in the art are used for delivering the composition. For inhalation, delivery uses any convenient system such as dry powder aerosol, liquid delivery systems, air jet nebulizers, propellant systems. For example, the formulation can be administered in the form of an aerosol or mist. The compositions may also be delivered in a sustained delivery or sustained release format. For example, biodegradable microspheres or capsules or other polymer configurations capable of sustained delivery can be included in the formulation. Formulations can be modified to alter pharmacokinetics and biodistribution. For a general discussion of pharmacokinetics, see, e.g., Remington's Pharmaceutical Sciences, 1990 (supra). In some embodiments the formulations may be incorporated in lipid monolayers or bilayers such as liposomes or micelles. Targeting therapies known in the art may be used to deliver the agents more specifically to certain types of cells or tissues.

The actual amount of active agent administered and the rate and time-course of administration will depend on the nature and severity of the disease. Prescription of treatment, e.g. decisions on dosage, timing, etc. is within the responsibility of general practitioners or specialists and typically takes into account the condition of the individual patient, the site of delivery, the method of administration and other factors known to practitioners. Examples of techniques and protocols can be found in Remington's Pharmaceutical Sciences, 1990 (supra).

Sustained-release preparations that may be prepared are particularly convenient for inducing immune responses. Examples of sustained-release preparations include semipermeable matrices of solid hydrophobic polymers containing the polypeptide, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers, and poly-D-(−)-3-hydroxybutyric acid. While polymers such as ethylene-vinyl acetate and lactic acid-glycolic acid enable release of molecules for over 100 days, certain hydrogels release proteins for shorter time periods. Liposomes may be used which are of the small (about 200-800 Angstroms) unilamellar type in which the lipid content is greater than about 30% cholesterol, the selected proportion being adjusted for the optimal therapy.

Stabilization of proteins may be achieved by modifying sulfhydryl residues, lyophilizing from acidic solutions, controlling moisture content, using appropriate additives, and developing specific polymer matrix compositions. The in vivo half life of proteins may be extended using techniques known in the art, including, for example, by the attachment of other elements such as polyethyleneglycol (PEG) groups.

Prime-boost immunization strategies as disclosed in the art are contemplated. See for example International Publication No. WO/2003/047617. Thus, compositions may be in the form of a vaccine, priming or boosting agent.

In another aspect, screening methods are provided employing substantially monomer depleted HCV E2. Screening methods involving substantially monomer depleted HCV E2 are directed at identifying binding molecules. Binding molecules, such as antibodies or antigen binding fragments, ligands, peptides, organic or inorganic molecules, are generally isolated and screened using art recognized protocols.

The present invention also provides for use of substantially monomer depleted HCV E2 in, or in the manufacture of a diagnostic agent for, the diagnosis or monitoring of HCV infection or monitoring of an anti-HCV treatment protocol.

The present invention provides methods for producing a purified antibody to a substantially monomer depleted HCV E2 composition comprising administering substantially monomer depleted HCV E2 glycoproteins or a nucleic acid encoding same to a subject and selecting antibodies therefrom that are able to bind to substantially monomer depleted HCV E2 and inter alia block receptor binding. Antibodies or antigen binding fragments are tested, in some embodiments, for their ability to neutralize virus activity such as their ability to reduce virus infectivity, viral budding or viral load.

The present invention contemplates a method of screening, the method comprising contacting a putative interacting compound with substantially monomer depleted HCV E2 glycoprotein; and determining binding characteristics of an interaction between the putative interacting compound and the E2 composition or its ability to bind to an HCV receptor such as CD81, or other host moiety bound by HCV.

The present invention contemplates a method comprising contacting a sample from a subject with a substantially monomer depleted HCV E2 glycoprotein; and determining an interaction between sample components and the HCV E2 glycoprotein. In some embodiments, arrays of different dimeric and/or trimeric or monomer depleted E2 glycoproteins from different HCV genotypes may be employed. In some embodiments, the sample is a sample comprising antibodies, such as a blood sample.

In some embodiments, the sample is from an infected subject. Control samples include samples from uninfected individuals. A sample may be from any part of the subject. Convenient samples include blood, serum, plasma, urine, sputum and the like. Suitable assays are known to those of skill in the art and include ELISA, RIA and EIA-like assays and competitive assays. The subject assays are particularly useful for serosurveillance.

In another aspect, the present invention provides a kit or a solid or semi-solid substrate comprising substantially monomer depleted HCV E2 glycoprotein. The kits or substrates of the present invention are contemplated for use in diagnostic, prognostic, therapeutic or prophylactic applications as well as for use in designing and/or screening HCV E2 binding molecules or HCV receptor binding molecules. The kits and substrates are also useful in monitoring the efficacy of a treatment protocol against HCV infection. In some embodiments, the kits or substrates further comprise in another part, substantially monomeric HCV E2.

A composition comprising substantially monomeric HCV E2 includes a preparation having more than 80%, 85%, 90%, 95%, 97%, or 99% (by weight) monomeric E2.

In some embodiments, kits comprising substantially monomer depleted HCV E2 glycoprotein are conveniently used for (or are for use in) diagnosis or prognosis of viral infection, or pathogen monitoring or serosurveillance kits, and optionally include packaging, instructions and various other components such as buffers, substrates, antibodies or ligands, control antibodies or ligands, and detection reagents.

In some embodiments, anti-trimer and anti-dimer and anti-higher order forms of HCV E2-specific antibodies are employed.

The term "isolated" and "purified" means material that is substantially or essentially free from components, that normally accompany it in its native state. For example, an "isolated nucleic acid molecule" refers to a nucleic acid or polynucleotide, isolated from the sequences which flank it in a naturally-occurring state, e.g., a DNA fragment which has been removed from the sequences that are normally adjacent to the fragment. In particular, an isolated HCV E2 includes in vitro isolation and/or purification of a protein from its natural cellular environment, and from association with other components of the cell. Without limitation, an isolated nucleic acid, polynucleotide, peptide, or polypeptide can refer to a native sequence that is isolated by purification or to a sequence that is produced by recombinant or synthetic means. In some embodiments, purified substantially monomer depleted HCV E2 is at least 95 to 99% pure.

Reference to variants includes parts, derivatives, and chemical analogs. Chemical analogs contemplated include modification of side chains, incorporation of unnatural amino acids and/or their derivatives during synthesis and the use of linkers or cross-linkers or other methods to inter alia impose conformational constraints.

The present invention is further described by the following non-limiting Examples. Materials and methods used in the Examples are provided below.

Protein Purification and Size-Exclusion Chromatography: Mammalian-Expressed E2 Proteins.

Two forms of E2 glycoproteins from three different isolates were produced, a wild-type $E2_{661}$-his construct (WT-his, WT $E2_{661}$-his) and modified version of $E2_{661}$-his lacking the three variable regions (HVR123-his) were expressed in mammalian expression systems using 293F cells. WT-his is described in WO 2008/022401. Alternatively, insect systems or yeast expression systems may also be used to produce E2 glycoproteins. Except where noted otherwise, reference to WT and modified version $E2_{661}$-his lacking the three variable regions refers to E2 sequence from the H77c (genotype 1a) strain of HCV.

Tissue-culture supernatants were purified using Ni-Sepharose 6 Fast-Flow resin (GE Healthcare) equilibrated with Ni-MAC buffer A and bound proteins eluted with Ni-MAC buffer B as per the manufacturers instructions. Protein-containing fractions were detected by Bradford assay (Bio-Rad) and buffer-exchanged into phosphate buffered saline (1×PBS; 10 mM $NaPO_4$, 150 mM NaCl, pH 7.3) using a HiPrep 26/10 Desalting column (GE Healthcare) and AKTA Explorer fast-liquid protein chromatography system (FPLC, GE Healthcare).

To isolate different forms of $E2_{661/5}$-his (JFH1 strain—in the JFH1 strain, there are insertions that contribute an extra 4 amino acid residues hence the end of E2 ectodomain is actually at residue 665), preparative size-exclusion chromatography was performed using the AKTA Explorer FPLC system and a TSKG3000swXL column (21.5 mm×60 cm, TOSOH Biosciences, 200 mL column volume (CV)) equilibrated in 1×PBS. The maximum injection volume was 2 mL and, prior to loading, purified proteins were concentrated to approximately 10 mg/mL using 10,000 Dalton (Da) molecular-weight cut-off (MWCO) filtration units (Amicon) according to the manufacturers instructions. Due to precipitation of proteins out of solution at this concentration, the buffer was titrated from pH 7.3 to 6.8 to avoid the predicted isoelectric point (pI) of these proteins (ProtParam). Samples were run at an average flow-rate of 2 mL/min and 2 mL fractions collected between 60-160 mLs. Fractions were pooled from multiple runs to obtain 0.1-1 mg/mL.

Analytical size-exclusion chromatography was performed using a Waters high-performance liquid chromatography system (HPLC, Alliance) and a smaller TSKG3000swxl column (TOSOH, 7.8 mm×30 cm, 15 mL CV) with a maximum loading volume of 0.2 mL. For maximum resolution, experiments were performed at a flow-rate of 0.25 mL/min for 60 mins in 1×PBS. Stability analysis was performed using this method at room temperature for the peak monomer and dimer fractions over 72 hrs with runs programmed every 24 h including a reference sample at 0 mins. Purified bovine serum albumin and Ovalbumin. at 0.5 mg/mL (GE Healthcare) were used as size-standard controls.

Proteins were quantified by absorbance at 280 nm using a NanoDrop (Thermo Scientific). Concentrations were adjusted using theoretical extinction coefficients ($\epsilon$) as determined from the amino-acid sequence in ProtParam (Expasy).

To isolate four distinct fractions of WT and Δ123 $E2_{661}$-his proteins, Ni Sepharose High Performance chromatography was performed. Proteins were loaded onto 5 ml HisTrap HP columns (GE Healthcare) in binding buffer containing 20 mM Sodium Phosphate, 0.5M NaCl, 10 mM Imidazole (low UV) pH7.4. A pre-elution wash step was carried out using 20 mM Sodium Phosphate, 0.5M NaCl, 25 mM Imidazole (low UV) pH7.4 and elution performed with 20 mM Sodium Phosphate, 0.5M NaCl, 500 mM Imidazole (low UV) pH7.4.

Size exclusion chromatography followed on Superdex 200 pg 26/60 columns (GE Healthcare). Selected fractions were pooled and 0.22 μm filtered.

An unfractionated mixture preparation for each protein was prepared using the same method for Ni Sepharose chromatography as above but not subjected to size exclusion. Following elution from Ni Sepharose samples were immediately desalted on HiPrep 26/10 desalting column (GE Healthcare).

Bacterial-Expressed Proteins.

The expression and purification of a chimera composed of maltose-binding protein (MBP) linked to the CD81 large extracellular loop (LEL) between residues 113 to 201 (MBP-LEL[113-201]) has been previously described (Drummer et al., *Biochem Biophys Res Commun* 328: 251-257, 2005; Drummer et al., *J Virol* 76: 11143-7, 2002). This dimeric form of the CD81-LEL has been used to extensively characterize E2-CD81 interactions and has been shown to be an excellent mimic of native CD81 and can interact with the first extracellular loop (EC1) of Claudin-1 (Harris et al., *J Biol Chem* 285: 21092-102, 2010). In addition, it reflects the homodimers observed in crystal structures of hCD81-LEL as well as the homotypic interactions between cell-associated full-length CD81.

CD81 MBP-LEL[113-201] WT and F186S transformed BL21 DE3 cells (Invitrogen) were grown in terrific broth (TB) supplemented with salts and ampicillin.

Protein expression was induced with 0.1 mM Isopropyl β-D-I-thiogalactopyranoside (IPTG) for 4 hrs at room temperature and cells harvested, washed and stored at −80° C. Soluble proteins were isolated by sonication in S-buffer, clarified at 20,000×g, and filtered through a 0.45 um filter. Protein was affinity-purified using amylose resin (New England Biolabs) according to the manufacturers instructions. Protein-positive fractions eluted in 10 mM maltose were determined by Bradford assay (BioRad). The dimeric and monomeric proteins were isolated by size-exclusion chromatography performed using an AKTA FPLC and Superdex 200 pg 16/20 column (GE Healthcare) equilibrated in S-buffer. Analytical size-exclusion chromatography using a HR Superdex 200 column (GE Healthcare) and AKTA FPLC confirmed the isolation of a single dimeric peak. Proteins were concentrated using 30,000 Da MWCO filtration units (Amicon) and quantified as above.

Polyacrylamide Gel Electrophoresis (PAGE).

Purified $E2_{661}$-his proteins were analyzed by pre-cast 4-12% Nu-PAGE (Novex) using prestained Precision-Plus size-standard markers (Bio-Rad). Proteins were subject to non-reducing or reducing conditions as required and visualized by staining with Coomassie Brilliant Blue solution (0.1% w/v Coomassie brilliant blue R-250 (Bio-Rad), 5% v/v glacial acetic acid, 50% v/v methanol). Gels were de-stained with 10% (v/v) methanol and 10% (v/v) acetic acid and the migration of Coomassie stained proteins analyzed by Odyssey LI-COR fluorescent scanner and quantification software.

The four distinct fractions and unfractionated mixtures of WT and Δ123 $E2_{661}$-his proteins were analysed using of 3 μg of each HCV-His variant added to 10 μl of 4× reducing/non-reducing sample buffer (Invitrogen). The samples were heated for 3 minutes at 70° C. and loaded onto 4-12% Bis-Tris Nu-PAGE SDS-PAGE gel. For reducing gels, 500 ul NuPAGE Antioxidant (Invitrogen, NP0005) was added to centre component of the gel tank before applying 200V.

Western Blot Analysis

The four distinct fractions and unfractionated mixtures of WT and Δ123 $E2_{661}$-his proteins were analysed using 0.5 μg of each HCV-His variant added to 4× reducing sample buffer (Invitrogen). Reducing SDS-PAGE was performed as described above. The proteins were then transferred to PVDF membranes via wet transfer (1 hr). The membranes were blocked overnight with 2% skim milk in PBS. Primary antibody was added at a dilution of 1:1000 (Penta•His & E2) in 0.05% TBS 1% skim milk. Three 10 min washes in 0.05% TBS were performed. A Secondary antibody of sheep anti-mouse IgG HRP (Millipore) was added at a dilution of 1:2000 in 0.05% TBS 1% skim milk. Three 10 min washes in 0.05% TBS were performed. ECL Plus Western Blotting Detection Reagent (GE, Product code RPN2132) was applied to the membranes according to manufacturer's instructions and bands visualized at 520 nm.

Mass Spectrometry Analysis.

Mass spectrometry analysis was performed using matrix-assisted laser desorption/ionization (MALDI) time-of-flight (TOF) mass spectrometry (MS): MALDI-TOF-MS. The monomeric and dimeric $E2_{661}$-his proteins—WT and ΔHVR1+2+3—were purified using a ZipTip (Millipore) according to the manufacturers instructions prior to MALDI-TOF-MS analysis.

Biosensor Analysis and Evaluation.

All experiments were performed using a Biacore 2000 unit (GE Healthcare). Protein ligands were buffer-exchanged into 10 mM sodium acetate, pH 4.2 prior to immobilization to a CM5 chip (GE Healthcare) via amine-coupling methods to obtain approximately 800 response units (RU). Immobilizations were performed in 1×HBS-N buffer (0.01 Hepes, 0.15M NaCl, 3 mM EDTA)). For all experiments, a negative-control ligand was immobilized in the preceding flow-cell or, alternatively, a negative-control analyte injection was used to allow subtraction for non-specific binding. Kinetic experiments were performed at a flow-rate of 10 uL/min in HBS-EP buffer (0.01 Hepes, 0.15M NaCl, 3 mM EDTA, 0.05% Tween 20). Protein analytes were injected into the system at 4-5 serial two-fold dilutions in FIBS-EP with a starting concentration of 0.1 mg/mL. Injections were performed for 250 sec to obtain an association rate and allowed to dissociate for 600 sec. An independent loading control at the mid-point concentration was included to ensure concentration accuracy. Regeneration between each cycle was performed at a flow-rate of 100 uL/min and involved two 15 uL pulses of 100 mM phosphoric acid.

The raw biosensor data was subject to global fitting according to three theoretical binding models based on equilibrium thermodynamics using BIAevaluation software (GE Healthcare). Notably, no bulk refractive index effects (RI) were observed in any of the raw data after background subtraction and RI was set to a constant zero value during fitting. Within the different reaction schemes, components A and B represent the ligand and the analyte, respectively.

The "1:1 Langmuir binding" model.

$A+B \leftrightarrow AB$, where "$ka$" is forward and "$kd$" is reverse.

$KD=kd/ka$

The association rate ($ka=1/Ms$) between analyte and ligand represents the forward reaction and is a function of the molar analyte concentration (M) and time in seconds (s). The dissociation rate ($kd=1/s$) represents the reverse reaction as a function of time, but is independent of concentration. The equilibrium dissociation constant or KD in molar units (M) can be calculated by dividing the dissociation rate (kd) by the association rate (ka).

The "two-state binding (conformational change)" model.

$A+B \leftrightarrow AB$, where '$ka1$' is forward and is '$kd1$' reverse.

$AB \leftrightarrow AB^*$, where '$ka2$' is forward and '$kd2$' is reverse.

$KD=(kd1/ka1)\times(kd2/ka2)$

This model generates two kinetic equations where the primary association rate ($ka1=1/Ms$) and dissociation rate ($kd1=1/s$) describe a 1:1 binding interaction as above. The secondary association rate ($ka2=1/s$) and dissociation rate ($kd2=1/s$) represent the kinetics of a conformational change occurring upon interaction between analyte and ligand. This interaction is described as a function of time (s), but is independent of the analyte concentration. The overall KD value is obtained by multiplying the KD values generated by the primary and secondary equations.

The "bivalent analyte" model:

$A+B \leftrightarrow AB$, where $ka1(\times 2)$ is forward and is $kd1$ is reverse.

$AB+B \leftrightarrow AB2$, where $ka2$ is forward and $kd2(\times 2)$ is reverse.

$KD=n/a$

This model generates two kinetic equations where the primary association rate ($ka1=1/Ms\times 2$) and dissociation rate ($kd1=1/s$) represent a 1:1 binding interaction as above, however the association rate (ka) is multiplied by two-fold to reflect the two available ligand-binding sites. The second association rate ($ka2=1/RUs$) is calculated as a function of response units (RU) and time in seconds (s). The second dissociation rate ($kd2=1/Ms\times 2$) is multiplied two-fold to reflect the two available ligand-binding sites. Notably, the bivalent binding model cannot generate an affinity constant or KD as the degree of mono- and bi-valent binding differs at different concentrations and therefore the dissociation rate (kd) is no longer independent of concentration.

As the changes in refractive index detected by the sensor chip are proportional to the changes in absorbed mass on the chip as measured in response units (RU), the theoretical maximum of analyte binding capacity ($R_{max}$) of each ligand was calculated using the equation below:

$R_{max} = $(analyte mass (MW)/ligand mass (MW))$\times R_L \times S$,

Here, $R_L$ is the level of immobilized ligand (CD81-LEL dimer) (RU) and S is the stoichiometric ratio of the interaction and therefore describes the relationship between molecular mass, RU and binding ratios. The theoretical $R_{max}$ is often higher than the experimental $R_{max}$ as the functionality/availability of the immobilized ligand is usually compromised especially when using non-specific immobilization methods such as amine coupling. The experimental $R_{max}$ can be used directly to determine the KD of an interacting system, but is often difficult to determine due to the large amount of analyte required to saturate the chip. Instead, the experimental $R_{max}$ and KD are predicted by global fitting of the association sensorgrams at multiple analyte concentrations as described above: 0.1-10 times the KD concentration is optimal for kinetic analysis.

Direct Binding Enzyme Immunoassays.

96-well Maxisorb enzyme linked immunosorbant plates (Nalge Nunc) were coated with 0.5 μg/ml *Galanthus nivalis* lectin (Sigma) diluted in PBS overnight 16 h at 4° C. The lectin was then removed and unoccupied sites blocked with BSA$_{10}$PBS (10 mg/mL BSA (Sigma) in PBS) for 1-2 h at room temperature. 2 µg/ml of recombinant E2 protein diluted in PBS containing 0.05% Tween 20 (PBST) was then added and incubated 1 h at room temperature. The plates were then washed four times in PBST. Serial dilutions of guinea pig serum in BSA$_5$PBST (5 mg/mL BSA in PBST) were then applied to E2 bound to *Galanthus nivalis* lectin-coated plates and incubated for 2 h at room temperature. Bound antibodies were detected using a horseradish peroxidise conjugate rabbit anti-guinea pig immunoglobulin (DAKO) (1:1000 dilution in BSA$_5$PBST) and developed with a tetra-methylbenzidine substrate (Sigma) according to the manufacturer's instructions. The resulting absorbance values (optical density) were read at 450 nm-620 nm (background) on the Fluostar (BMG technologies).

CD81 Inhibition Assays.

Briefly, 96-well Maxisorb enzyme linked immunosorbant plates (Nalge Nunc) were coated with 5 µg/mL of dimeric CD81 MBP-LEL$^{113-201}$ in PBS and incubated for 16 h at 4° C. The MBP-LEL$^{113-201}$ was removed prior to blocking with BSA$_{10}$RBS (10 mg/mL BSA (Sigma) in PBS) for 2 h at 37° C. to reduce non-specific binding. The plates were then washed four times in PBST (0.05% Tween-20 (Sigma) in PBS). Serial dilutions of immune sera in BSA$_5$PBST (5 mg/mL BSA in PBST) were mixed with 50 ng of either H77c or JFH1 WT E2$_{661}$-his proteins before addition to MBP-LEL$^{113-201}$ coated immunoassay plates. Bound E2$_{661}$-his was detected using rabbit anti-his antibody (Rockland Immunochemicals). After further washing in PBST, the residual E2 complexes bound to MBP-LEL$^{113-201}$ were detected using a horseradish peroxidise conjugate anti-rabbit immunoglobulin (DAKO) (1:1000 dilution in BSA$_5$PBS/Tween) and developed with a tetra-methylbenzidine substrate (Sigma) according to the manufacturer's instructions. The resulting absorbance values (optical density) were read at 450 nm-620 nm (background) on the Fluostar (BMG technologies). The 80% inhibition titre was calculated for each serum sample.

HCVpp Neutralization Assay

HEK 293T cells were cotransfected with 1 µg each of pNL43.LUC.R-E-plus either H77c pE1E2 vector (Drummer et al., *FEBS Lett* 546: 385-90, 2003) or pcDNA4HisMax vector encoding a non functional E1E2 (empty). At 72 hrs post-transfection, culture supernatants containing HCVpp were collected and filtered (0.45 µm). Serial dilutions of guinea pig sera was incubated for 1 h at 37° C. with H77c HCVpp viruses and then added in quadruplicate to Huh7.5 cell seeded the day prior at 3×10$^4$ cells/well in monolayers in 48-well tissue culture plates (Nunc, Nalge). Following a 4 h incubation (37° C., 5% CO2) the cells were washed with PBS and the medium replaced. After an additional 3-day incubation (37° C. in 5% CO2), the cells were lysed and luciferase activity assayed in a Fluostar fitted with luminescence optics (BMG labtechnologies).

HCV Cell Culture-Derived Virus (HCVcc) Entry, Inhibition of Entry and Neutralization Assays.

HCV RNA was in vitro transcribed from plasmid DNA encoding the infectious J6/JFH1 chimeric genotype 2a genome containing a Gaussia luciferase gene as previously described. The same plasmid containing a GND mutation conferring loss of infectivity was included as a negative control. The DNA plasmids were linearized by digestion with XbaI and transcribed using a T7 Megascript kit. The DNA template was then removed by incubation with DNaseI and the amplified RNA precipitated using the phenol-chloroform method. RNA was quantified and imaged by 1% agarose-formaldehyde gel. RNA was transfected into Huh7.5 cell monolayers using DMRIE-C (Invitrogen) reagent according to the manufacturers instructions and HCVcc-containing supernatants harvested after 72 hours. The supernatants were clarified and stored at −80° C.

HCVcc infectious titers were determined by a limiting dilution assay (TCID$_{50}$) (Lindenbach et al., *Science* 309 (5734): 623-626, 2005). Briefly, virus stocks were serially diluted and applied to cells plated at 3×10$^3$/well in 96-well dishes. 72 h post-infection, the cells were washed with 1×PBS and fixed in ice-cold methanol prior to detection of infected cells with anti-FLAG antibody. Bound antibodies were detected using polyclonal goat anti-mouse conjugated with horseradish peroxidase diluted 1:3 in PBST and incubated for 1 hr at room temperature. Cells were then washed twice with PBS and once with PBST. Infected cells were visualized by addition of 3,3'-Diaminobenzidine (DAB) substrate and incubated for 5 min at room temperature. Cells were then washed twice with PBS and 50 µl of PBS buffer was added to the cells to avoid drying. Cells were visualized under the microscope and positive wells were calculated.

The TCID$_{50}$ was calculated using the method of Reed-Muench (Reed and Muench, *A simple method of estimating fifty percent endpoints*, The American Journal of Hygiene 27: 493-497, 1938). The Reed-Muench method calculates the exact dilution that gives 50% infection by this equation:

$$\text{Proportionate distance } (PD) = \frac{(\% \text{ positive above } 50) - 50\%}{(\% \text{ positive above } 50) - (\% \text{ positive below } 50)}$$

$$\text{Log TCID}_{50} = (\log \text{ dilution above } 50\%) - (PD \times \log \text{ dilution factor})$$

For HCVcc neutralization assays, 100 ul serial dilutions of guinea pig serum prepared in DMEM containing 10% fetal calf serum and non essential amino acids (DMFNEAA) was added to 100 ul of HCVcc virus and incubated for 1 hour at room temperature then added to Huh 7.5 cells seeded the day prior at 8×10$^3$ cells/well in 96 well tissue culture plates. Four hours later, the antibody/virus mixture was removed from cells, washed three times in PBS and replaced with 500 uL DMFNEAA. Forty four hours post-infection, luciferase activity in the tissue culture supernatant was quantified using a *Renilla* luciferase kit (Promega) and a Fluostar (BMG laboratories) fitted with luminescence optics.

Example 1

Isolation and Characterization of E2$_{661}$-his WT and E2 Core Domain Glycoproteins Large-scale preparations of E2$_{661}$-his proteins, both WT and ΔHVR1+2+3, derived from H77c, Con1 and JFH-1 isolates were expressed in 293F cells and the secreted protein purified using nickel-affinity chromatography via the C-terminal polyhistidine tag. cDNAs were prepared encoding Con1 E2 (HCV Con1 polyprotein residues 384-661; GenBank Accession No. AJ 238799) and JFH1 E2 (HCV JFH-1 polyprotein residues 384-665; GenBank Accession No. AB 047639.

To isolate the monomeric species of WT and E2 core domain proteins, preparative-grade high-resolution size-exclusion chromatography was performed (FIG. 1). Fifty-fractions across the expression profile E2$_{661/5}$-his were collected from multiple runs and the corresponding fractions pooled. Approximately 20 central fractions spanning the $E2_{661/5}$-his monomer, dimer and higher-order molecular mass 'shoulder' were isolated containing between 0.1 and 1 mg/mL of protein for further characterization.

As shown in FIGS. 2-4, analytical size-exclusion chromatography for WT, ΔHVR1+2+3 of each of the three isolates confirmed the isolation of the peak fractions representing the monomer and dimer peaks, but also a third independent peak within the 'shoulder' likely to represent a trimeric species.

Nickel affinity purified forms of H77c $E2_{661}$-his containing single (ΔHVR1, ΔHVR2 ΔigVR), double (ΔHVR1+2. ΔHVR2+3, ΔHVR1+3) or a triple deletion (ΔHVR1+2+3) deletion of the variable regions of E2 were analysed on an analytical gel filtration column and compared to intact H77c WT (WT) $E2_{661}$-his. The results show that all forms of $E2_{661}$-his contain evidence for monomer, dimer, trimer and high molecular weight forms of $E2_{661}$-his.

Stability analysis using analytical size-exclusion chromatography demonstrated that there was no detectable degradation of the monomeric or dimeric species over 72 hours at room temperature or spontaneous association into higher-order forms (data not shown). The Con1 and JFH1 $E2_{661/5}$-his proteins were similarly purified and analytical gel filtration of individual peaks corresponding to putative monomer, dimer and trimer were derived.

Each fraction was subjected to SDS-PAGE analysis under non-reducing and reducing conditions as shown in FIG. 6-8 for H77c, Con1 and JFH-1WT (A) and ΔHVR1+2+3 (B) $E2_{661}$-his proteins. The high-order trimer and dimeric proteins were predominantly disulfide-linked as they only migrated with the monomer after treatment with a reducing agent. Reducing SDS-PAGE also revealed that these forms were quite heterogeneous as additional species were detected migrating between approximately 100-150 kDa, 55 kDa and 45 kDa across H77c-derived WT fractions 13-23 (FIG. 6A lower panel). In the ΔHVR1+2+3 fractions, additional species migrating at 100 kDa, 45 kDa and 40 kDa were observed across fractions 15-18. The smaller proteinaceous species may indicate that a proportion of $E2_{661}$-his molecules within the higher order molecular mass fractions form aberrant disulfides with truncated $E2_{661}$-his and/or $E2_{661}$-his differentially modified by N-linked glycosylation. It is also possible that aberrant disulfides could be formed with other secreted proteins that are co-purified with $E2_{661}$-his under native-conditions. The higher molecular mass species are likely to represent dimeric $E2_{661}$-his forms that remain oxidized, but could potentially also represent other larger secreted proteins that have engaged in aberrant disulfides with the $E2_{661}$-his molecule during biosynthesis.

A similar profile of migration was observed in proteins collected in individual fractions of Con1 and JFH1 H77c WT (A) and ΔHVR1+2+3 (B) $E2_{661}$-his proteins (FIGS. 7 and 8).

The average molecular masses of the three independent peaks of H77c WT and ΔHVR1+2+3 $E2_{661}$-his proteins were quantified under non-reducing and reducing conditions.

Example 2

Kinetic Analysis of $E2_{661}$-his Proteins Binding to Recombinant CD81

After successfully isolating highly pure and stable monomeric samples of both WT and ΔHVR1+2+3 $E2_{6611.5}$-his proteins derived from H77c, Con1 and JFH1 isolates, a comparative kinetic analysis of binding to MBP-LEL113-201 was performed. Dimeric MBP-LEL113-201 WT was immobilized to a sensor chip via amine coupling and the MBP-LEL113-201 F186S mutant immobilized to the preceding (or reference) flow cell to allow subtraction for non-specific binding. The changes in refractive index detected by the sensor chip are proportional to the changes in absorbed mass on the chip and, therefore, the increase/decrease in response units (RU) represents association/dissociation of analytes interacting with the immobilized ligand.

To investigate this further, a kinetic analysis using biosensor techniques was performed between the different fractions representing monomer, dimer and trimer samples of WT and ΔHVR1+2+3 derived from H77c, Con and JFH1 isolates. MBP-LEL113-201 (including the F186S control) was immobilized to the chip and the $E2_{661}$-his proteins injected at a number of different concentrations to enable global fitting by BIAevaluation software as shown in FIG. 9 for H77c. The "best-fit" model was determined by the lowest Chit value and smallest residuals observed for each fit.

The Rmax of the WT dimer is lower than would be predicted suggesting that approximately half this preparation may be non-functional.

Figure 10:
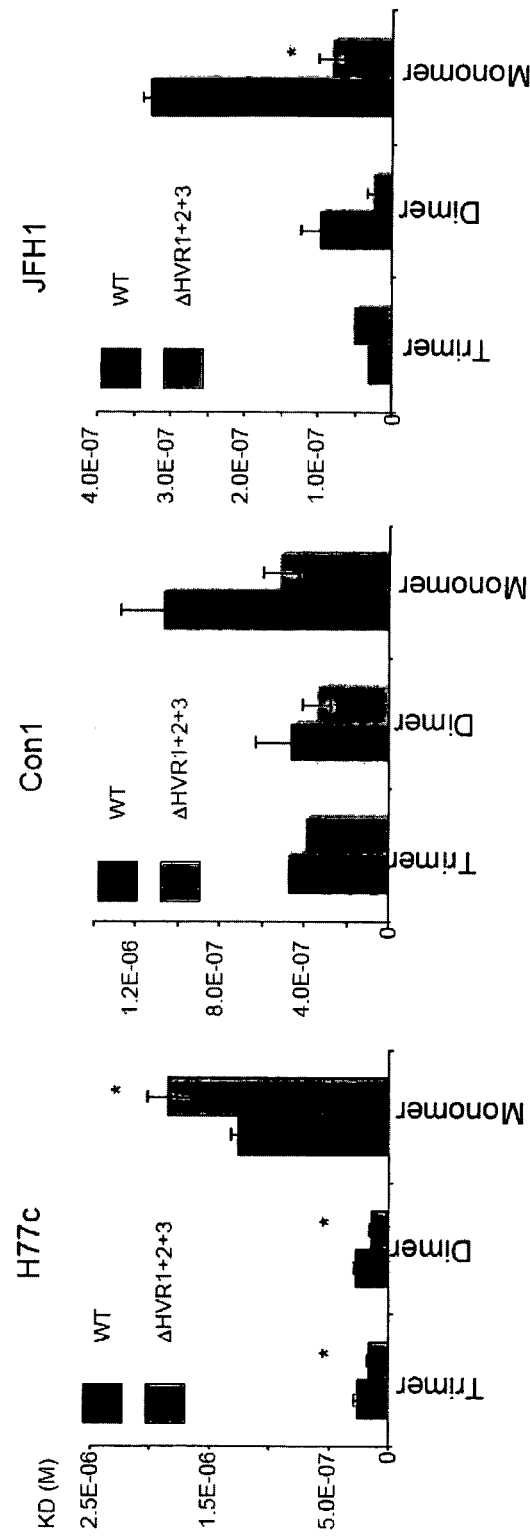
Figure 11:
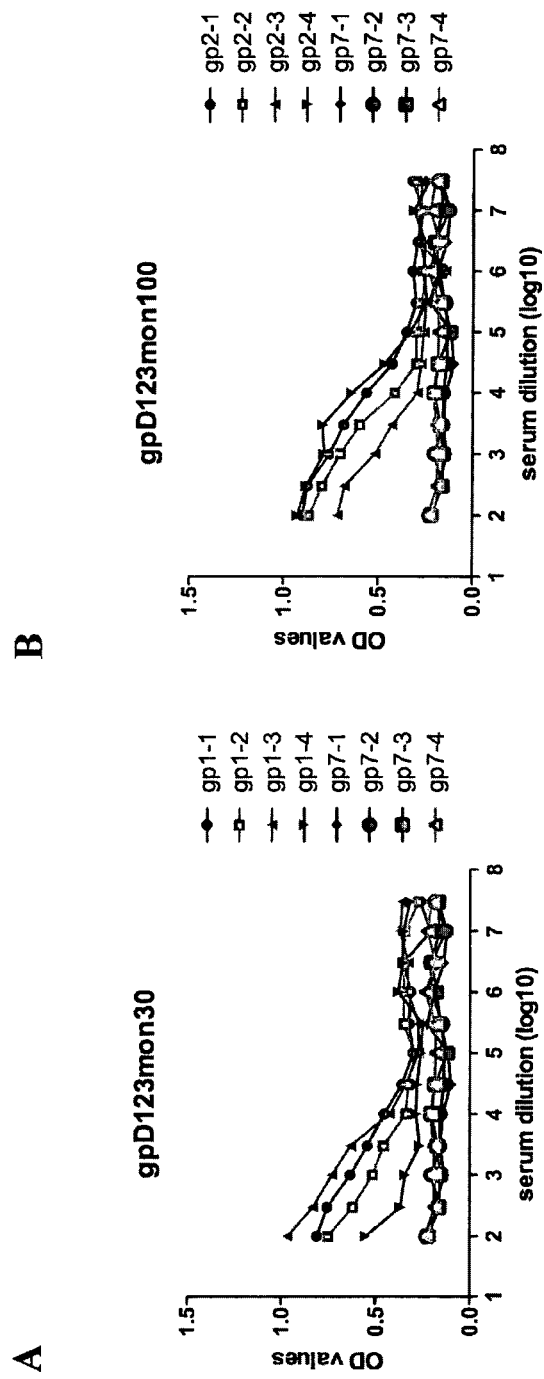
Figure 11:
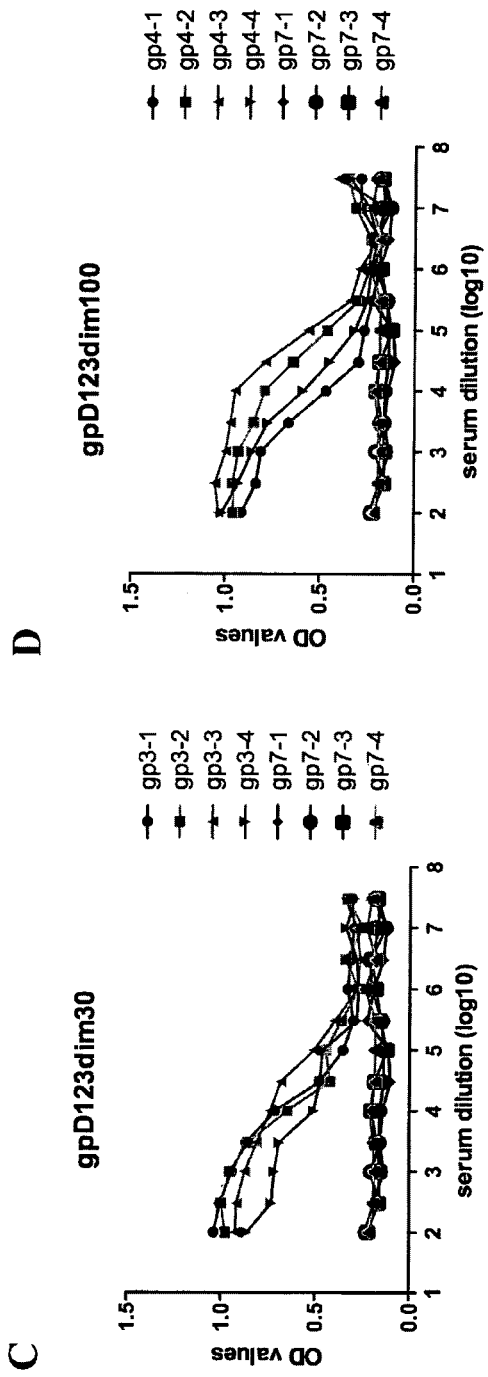
Figure 11:
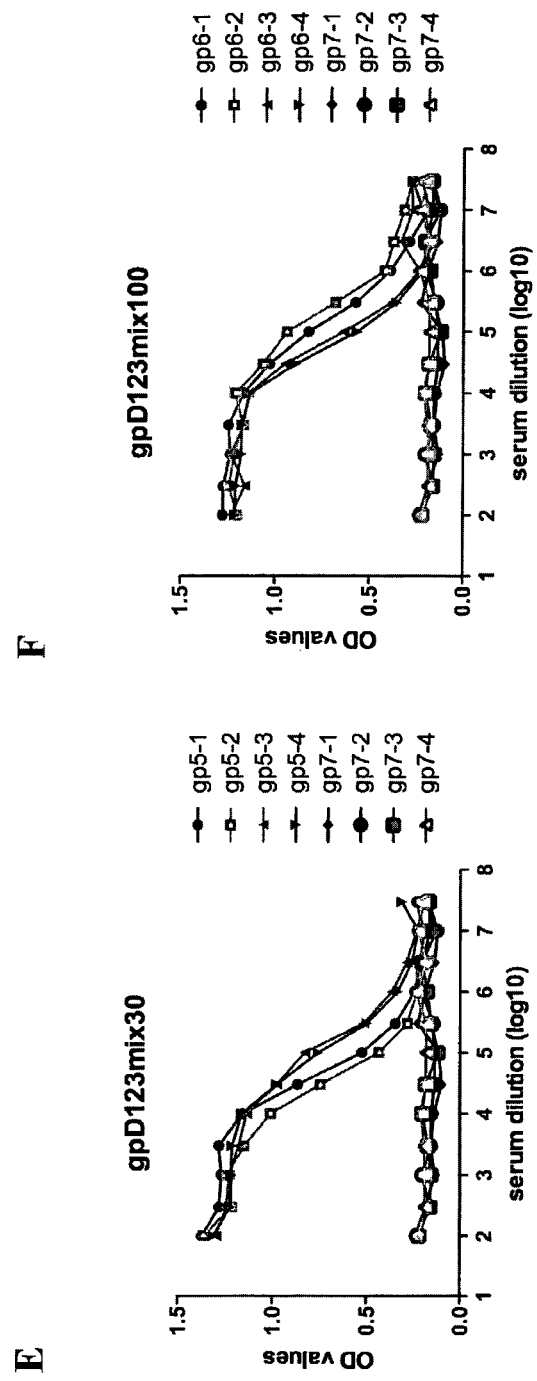
Figure 12:
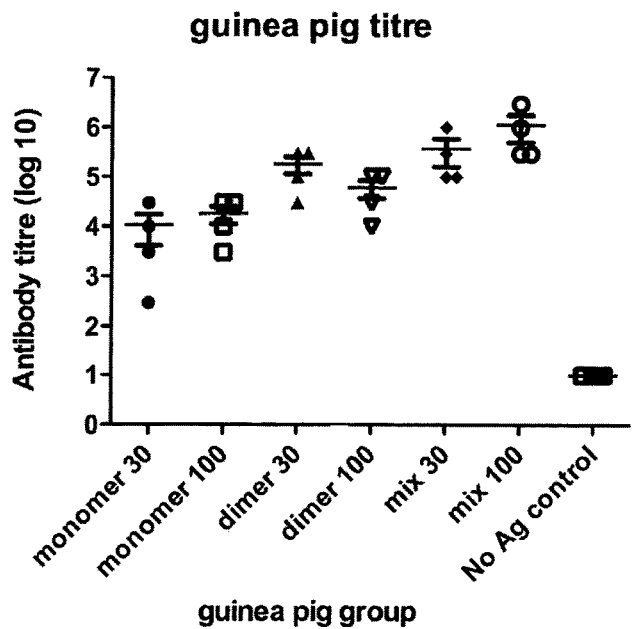
Figure 13:
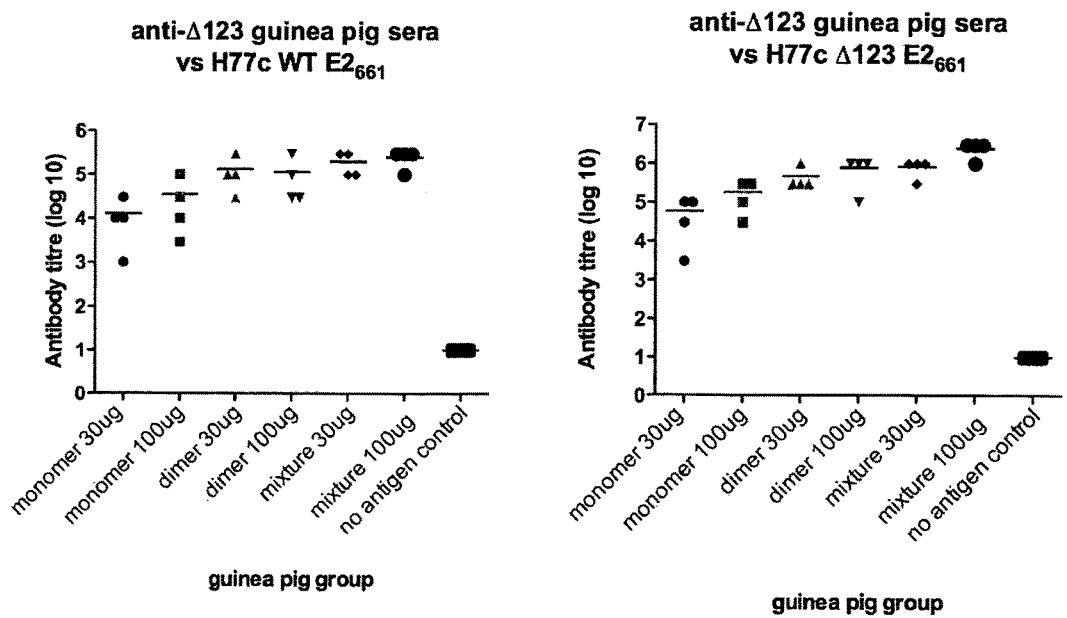
Figure 15:
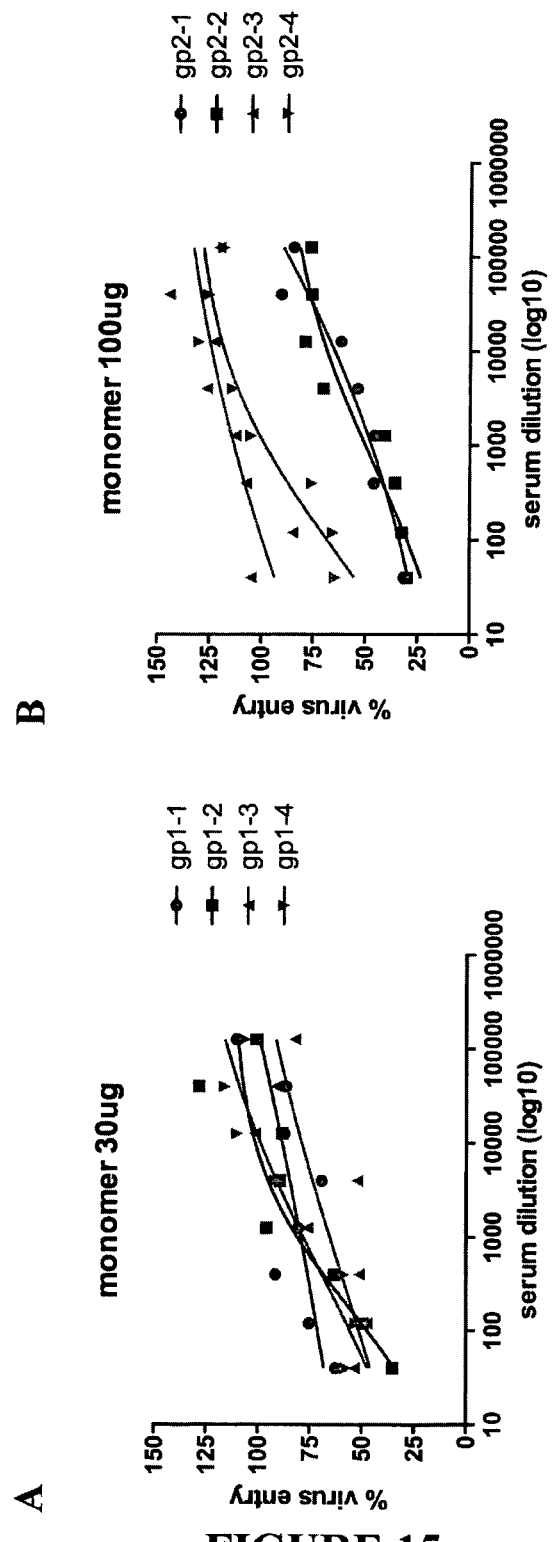
Figure 15:
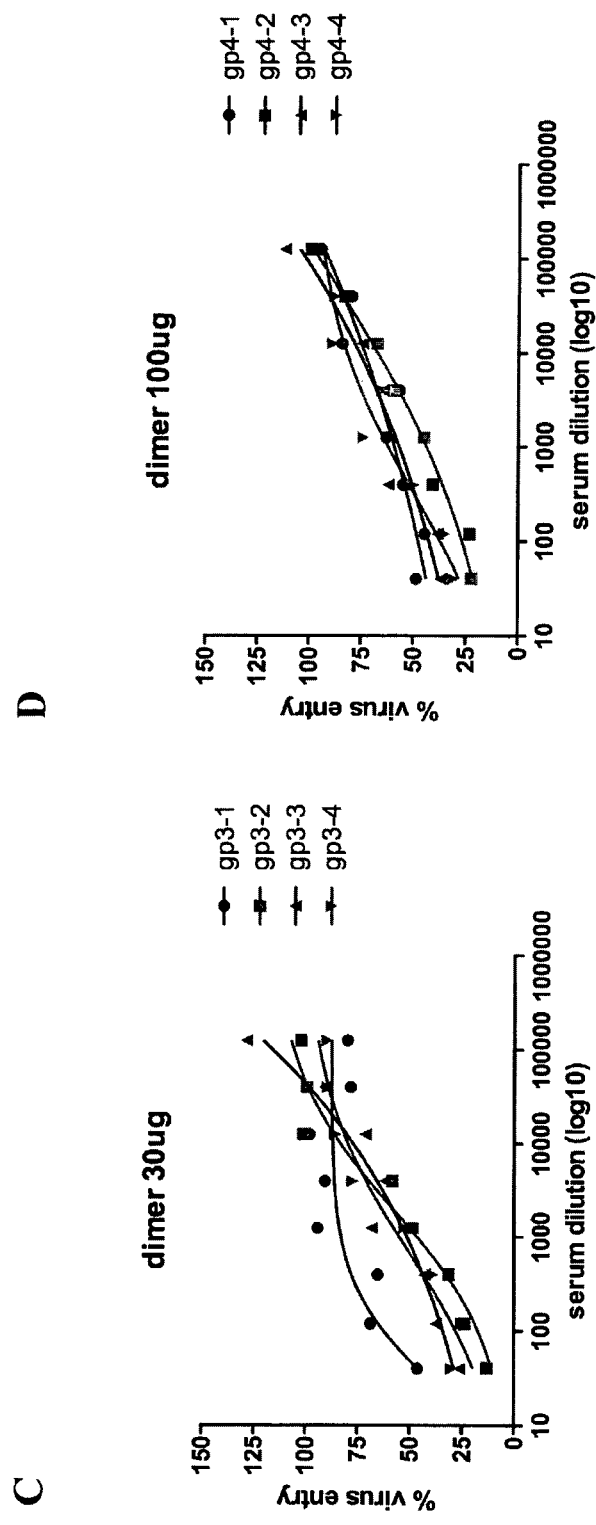
Figure 15:
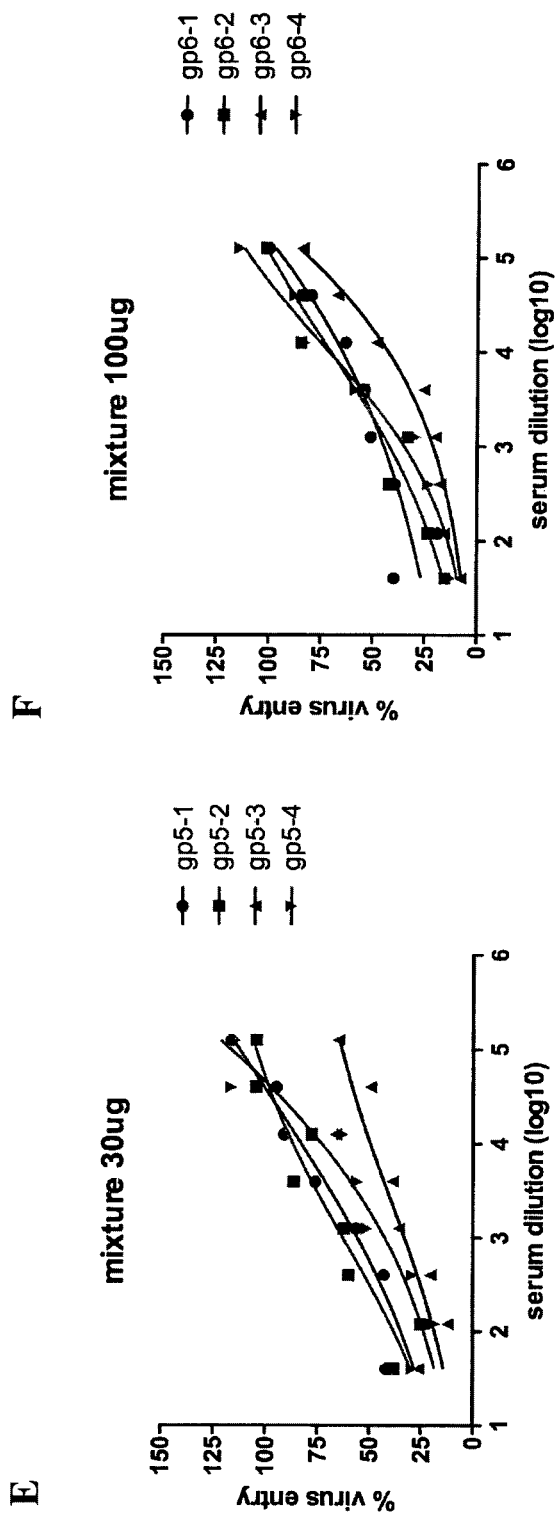
Figure 15:
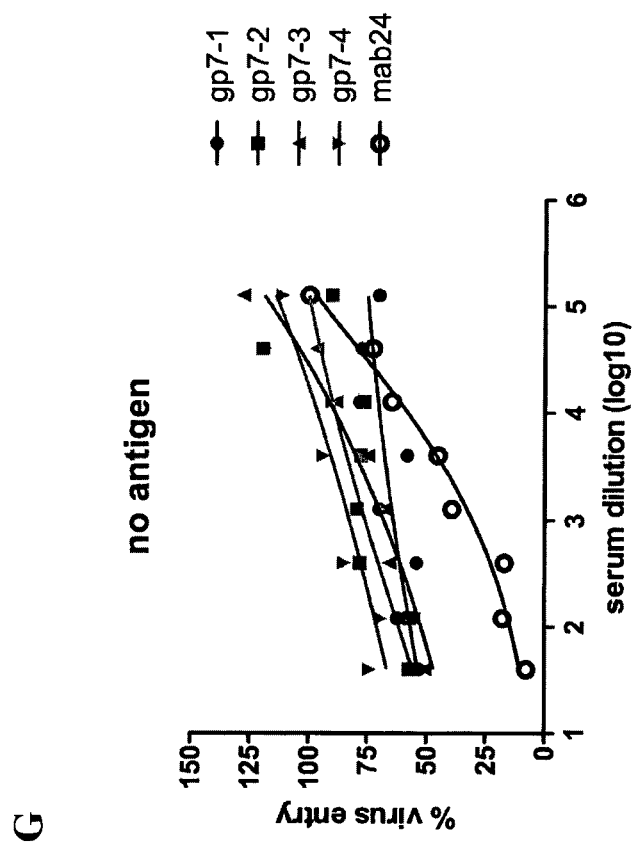
Figure 16:
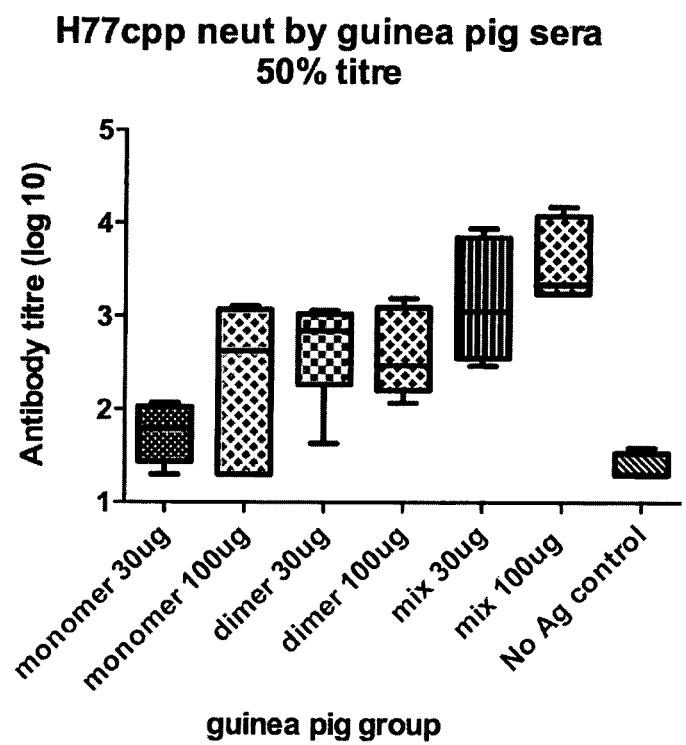
Figure 17:
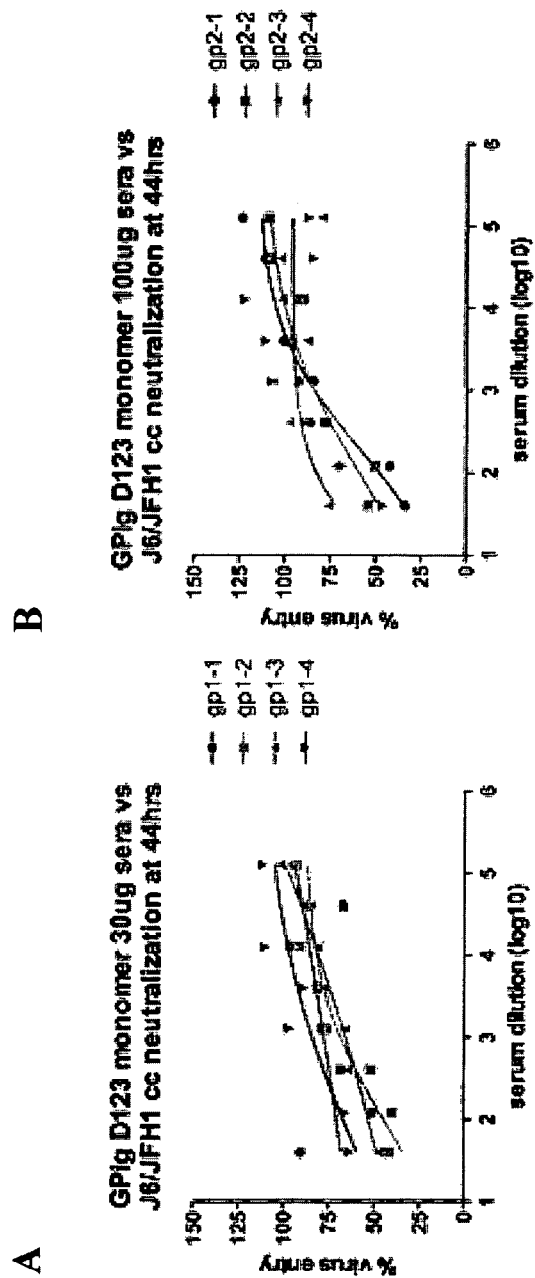
Figure 17:
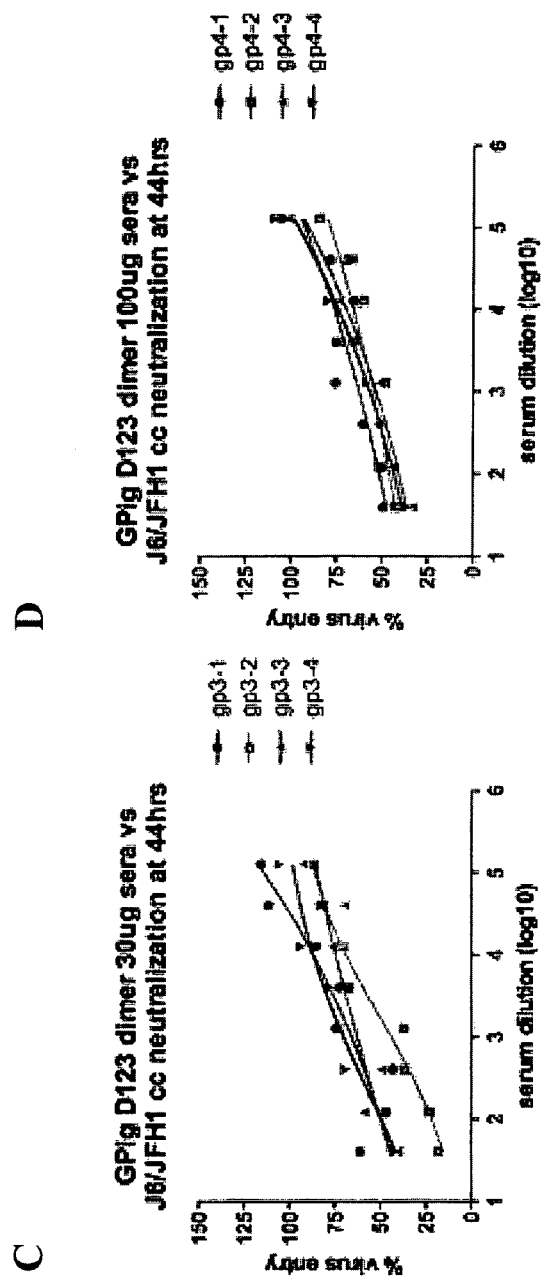
Figure 17:
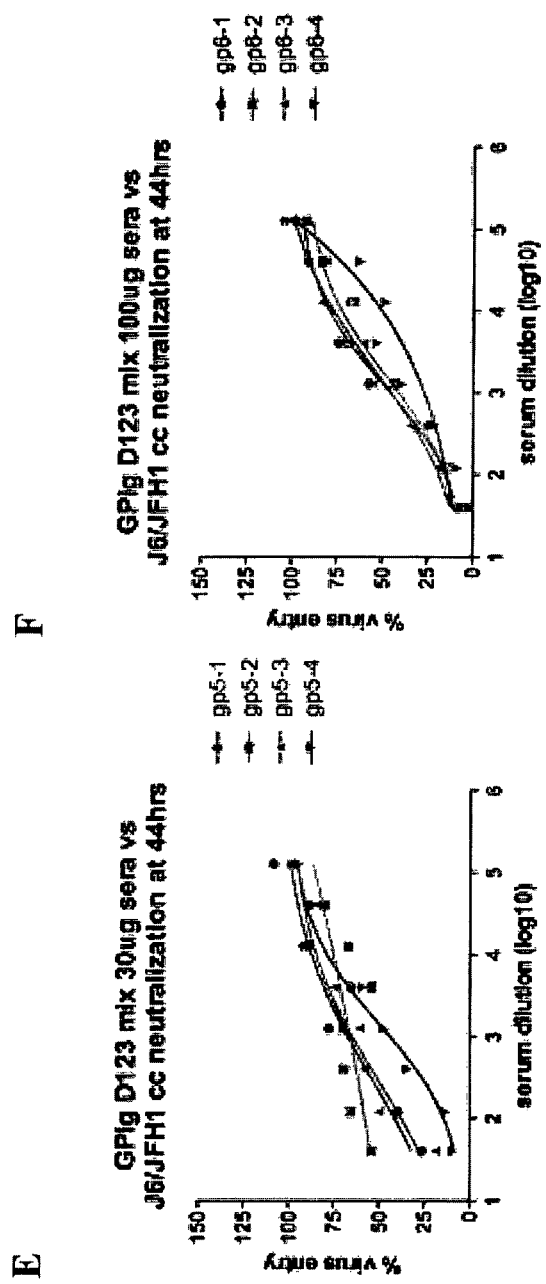
Figure 17:
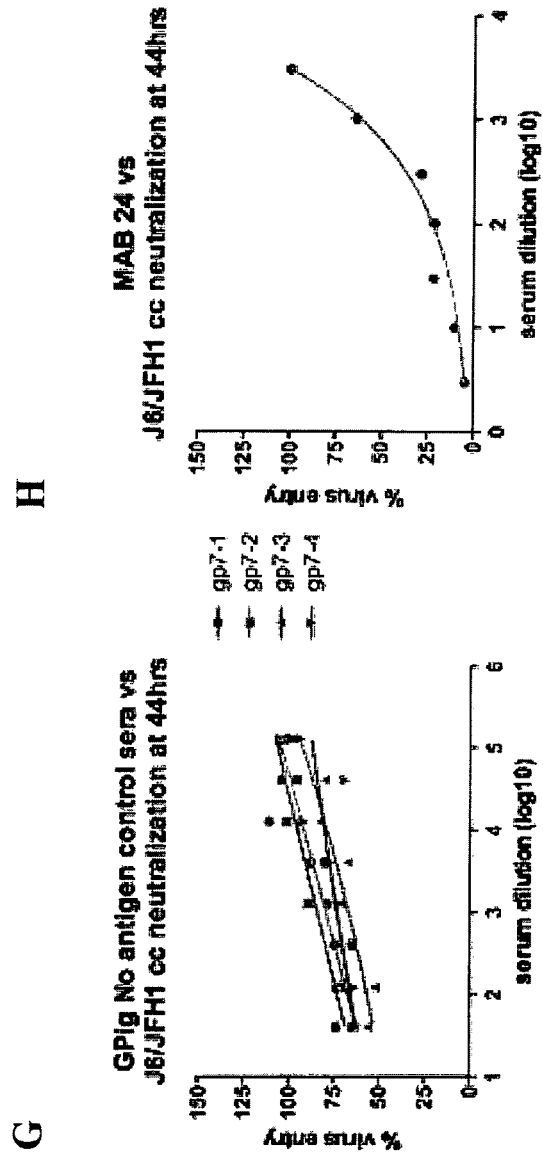
Figure 18:
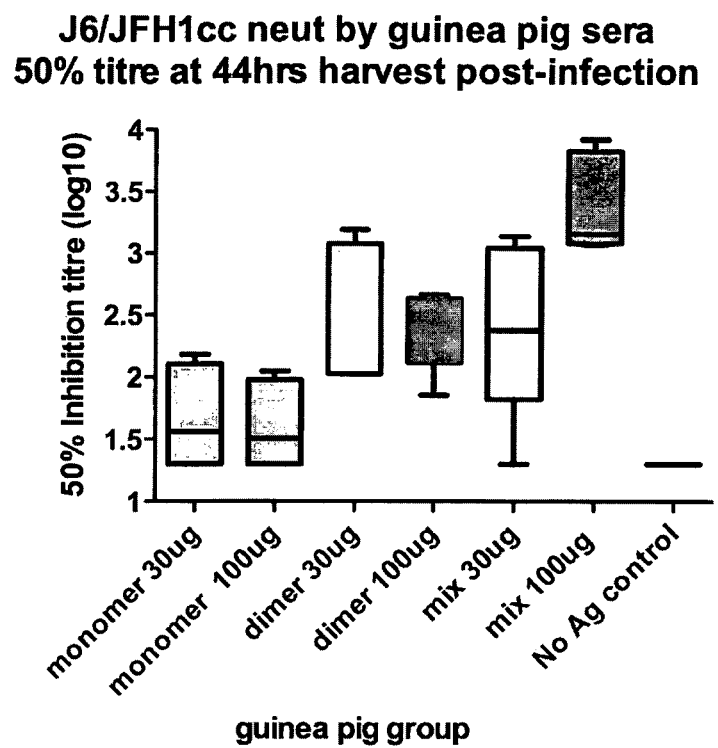
Figure 19:
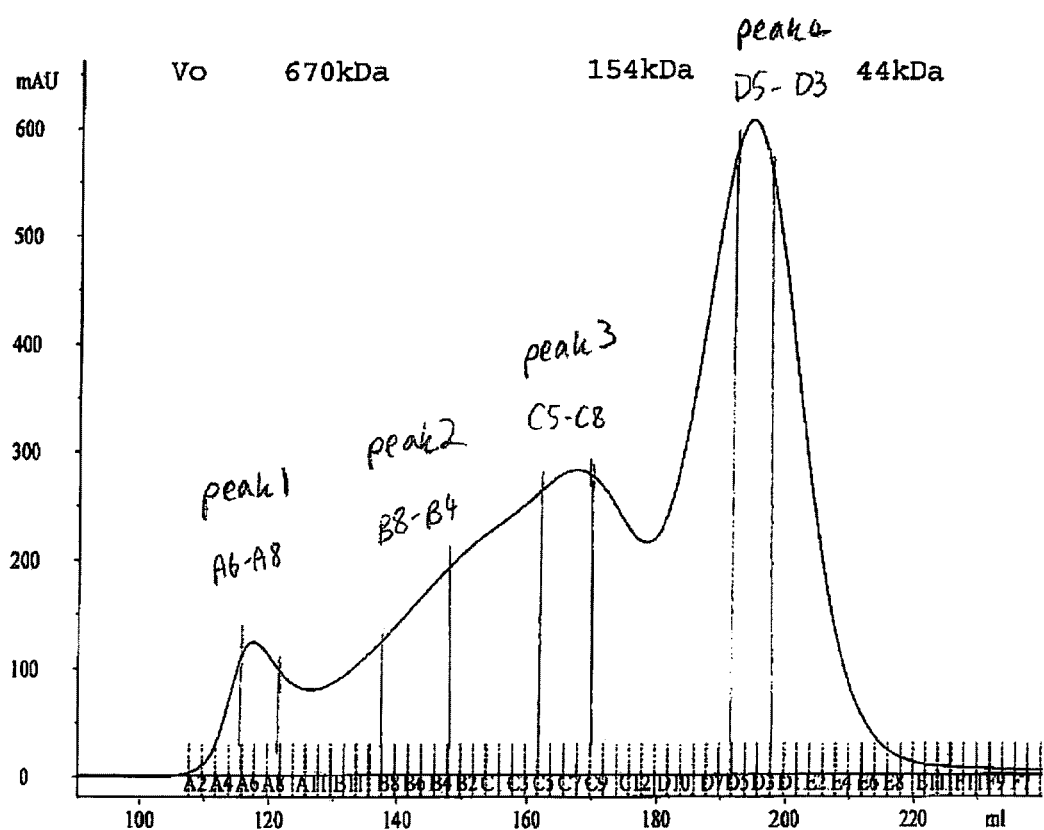
Figure 20:
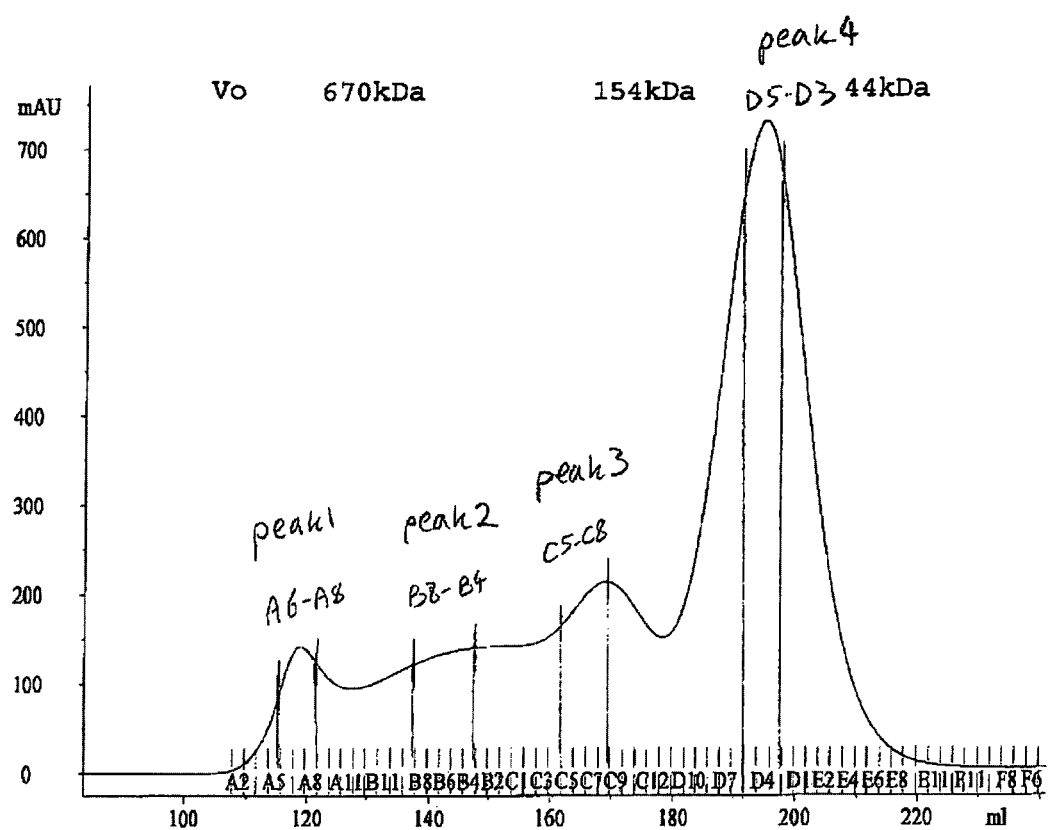

Both dimeric WT and HVR1+2+3 H77c $E2_{661}$-his proteins displayed a preference for the "bivalent analyte" model. The "1:1 Langmiur binding" model also displayed a good fit to biosensor curves generated by each protein and could be used to estimate a KD value. In FIG. 10, all KD values for the monomer, dimer and trimer $E2_{661}$-his proteins are shown confirming that the higher-order molecular mass forms were binding to MBP-LEL113-201.

Best-fit data using 2-state binding (conformational change) for monomeric proteins and 1:1 binding for dimeric/trimeric proteins showed that in H77c, the dimer/trimer proteins have approximately 10-fold higher affinity (lower KD values) for CD81 most likely due to bivalent interactions (FIG. 10). Con1 and JFH-1 display a similar trend (FIG. 10). The dimeric H77c ΔHVR1+2+3 $E2_{661}$-his protein has a higher affinity to CD81 than its WT counterpart (~2-fold).

Example 3

Guinea Pig Vaccination of Monomeric, Dimeric & Mixed Proteins of Δ123 $E2_{661}$-his Deletion of all three variable regions from a recombinant form of the HCV glycoprotein E2 receptor binding domain ($E2_{661}$) was demonstrated to elicit higher mean titres of cross-neutralizing antibody than intact $E2_{661}$-his proteins in mice.

In order to determine the response to A 123 $E2_{661}$-his-his proteins in a larger, out-bred animal model, a dose response experiment was performed in guinea pigs immunized with H77c Δ123 $E2_{661}$-his recombinant antigen. The functional significance of the different forms of $E2_{661}$-his observed in gel filtration chromatography was examined by separating monomeric and dimeric forms of $E2_{661}$-his for vaccination.

To determine if the different forms of the antigens influence the immunogenicity of the vaccine formulation, groups each of four guinea pigs were vaccinated three times with either 30 μg or 100 μg antigen in ISCOMATRIX™ adjuvant at three weekly intervals (Table 1). Guinea Pigs were then bled and sera stored at −80° C. The antigens were purified by nickel agarose affinity chromatography to yield a mixture of monomer, dimer and high molecular weight forms of E2 (mixed). Various forms were separated by gel filtration on a TSK3000sw column. The molecular mass of monomer and dimer forms was confirmed by mass spectrometry and sedimentation equilibrium.

Example 4

Homologous Mean Antibody Titres Showing Monomeric Δ123 E2$_{661}$-his is Weakly Immunogenic Compared to Mixed and Dimeric Forms Guinea Pig sera were tested in an enzyme immunoassay for the ability to bind the homologous immunizing H77c Δ123 E2$_{661}$-his antigen. The results show that guinea pigs vaccinated with Δ123 E2$_{661}$-his made antibody capable of recognizing homologous immunizing antigens. Strong dose and antigen specific effects were observed between the vaccine groups. In all cases, 100 μg of protein was more immunogenic than 30 μg. Furthermore, guinea pigs vaccinated with the mixed form of Δ123 $E2_{661}$-his elicited significantly higher mean titres of antibody compared to guinea pigs vaccinated with dimeric or monomeric antigen, with the lowest antibody mean titres observed in the monomer groups (FIG. 11). Mean antibody titres in the 100 μg mixed group were approximately 0.5 log higher then the 30 μg mixed group, 1 log higher than the dimer group and 2 logs higher than the monomer group (FIG. 12).

Example 5

Immune Serum Binds to WT and Δ123 Forms of $E2_{661}$-his Mixtures

The reactivity of the immune sera towards the WT and Δ123 $E2_{661}$-his mixtures was examined in a direct binding enzyme immunoassay. The data show that all animals elicited significant mean titres of antibody capable of reacting towards WT and Δ123 antigens. However, the mean titres of antibody reactive towards Δ123 were 5-10 fold higher compared to the WT $E2_{661}$-his protein (FIG. 13). The titre of antibody elicited was related to dose, with 100 μg the more effective dose. In addition, the form of the immunogen influenced the titre of antibody as the animals receiving the mixture and dimeric forms of $E2_{661}$-his elicited higher mean titres of antibody compared to animals vaccinated with monomeric protein.

Example 6

Immune Serum Inhibits the Binding of E2 to the Cell Surface Receptor CD81

The ability of the immune sera to inhibit the binding of HCV glycoprotein E2 to CD81 is believed to be a major indicator of the ability of immune serum to inhibit the ability of HCV to enter target cells. The ability of the immune sera to block the interaction between WT $E2_{661}$-his protein and recombinant form of the large extracellular loop of CD81 (MBP-$LEL^{113-201}$) was examined in a solid phase enzyme immunoassay.

Serial dilutions of immune sera were mixed with 100 ng of either H77c or JFH1 WT $E2_{661}$-his proteins before addition to MBP-LEL113-201 coated immunoassay plates. Bound $E2_{661}$-his was detected using anti-his antibody. The 80% inhibition titre was calculated for each serum sample and is plotted as a dot-plot in FIG. 14. The data shows that animals vaccinated with mixtures of Δ123 proteins elicited the highest mean titres; E2-CD81 inhibition antibodies were able to inhibit both homologous H77c and heterologous JFH1 $E2_{661}$-his from binding CD81. Lower mean titres of E2-CD81 inhibition antibodies were elicited in animals vaccinated with dimeric forms of $E2_{661}$-his protein with at least one animal in each group failing to elicit antibodies capable of reaching 80% inhibition. Monomeric $E2_{661}$-his vaccinated animals elicited the lowest mean titres of E2-CD81 inhibition antibodies. This demonstrates that the dimeric form of both the WT and A 123 $E2_{661}$-his is superior to monomeric $E2_{661}$-his in the induction of E2-CD81 inhibition antibodies. However, the form of $E2_{661}$-his present within the mixture of $E2_{661}$-his proteins is superior to dimeric $E2_{661}$-his alone.

Example 7

Homologous Neutralization of H77c HCVpp

The ability of immune sera to mediate homologous neutralization was determined using retroviral pseudotyped particles containing the H77c E1E2 glycoproteins. Serial dilutions of heat inactivated immune sera were admixed with HCVpp and added to Huh7.5 cells for 4 h. After washing, cells were incubated for a further 3 days and luciferase activity quantitated in the cell lysate. The results show that the ability to mediate neutralization of HCVpp was also dose and antigen dependent (FIG. 15). The guinea pigs that received 100 μg of mixed antigen elicited NAb mean titres approximately 10 times higher than those observed for 100 μg monomer, 30 μg dimer or 100 μg dimer (FIG. 16). The guinea pigs that received 30 μg monomer showed limited ability to neutralize HCVpp and the curves are similar to the control no antigen group (FIG. 15).

Example 8

Immune Sera Mediate Cross Neutralization of Cell Culture Derived J6-JFH1

Serial dilutions of immune sera were mixed with J6-JFH1 cell culture derived HCV and added to Huh7.5 cells. The luciferase activity in supernatant fluid was quantitated 44 h after infection and the results are shown in FIG. 17. The guinea pigs that received 100 μg mixed antigen showed a strong ability to mediate cross neutralization achieving 90% inhibition of entry at a 1/40 serum dilution (FIG. 17). The mean 50% neutralization titre observed for the 100 μg mixed group was almost 2 logs higher than the μg and 100 μg monomer groups and 1 log higher than the dimer groups and 30 μg mixed group (see FIG. 18).

Example 9

Separation of Proteins into Four Distinct Fractions

The H77c sequences of WT $E2_{661}$-his and Δ123 $E2_{661}$-his proteins were expressed in 293F cells. Tissue culture supernatants containing the secreted expressed proteins were subjected to nickel-affinity purification on a HisTrap column followed by gel filtration on a superdex 200 pg 26/60 column. Four distinct oligomeric peaks (peaks 1, 2, 3, 4) of WT $E2_{661}$-his (FIG. 19) and Δ123 $E2_{661}$-his (FIG. 20) were observed and for each peak fractions were collected and pooled. In addition, "unfractionated" preparations of WT $E2_{661}$-his and $\Delta 123$ $E2_{661}$-his proteins were partially purified on HisTrap column, but not subjected to gel filtration.

Figure 21:
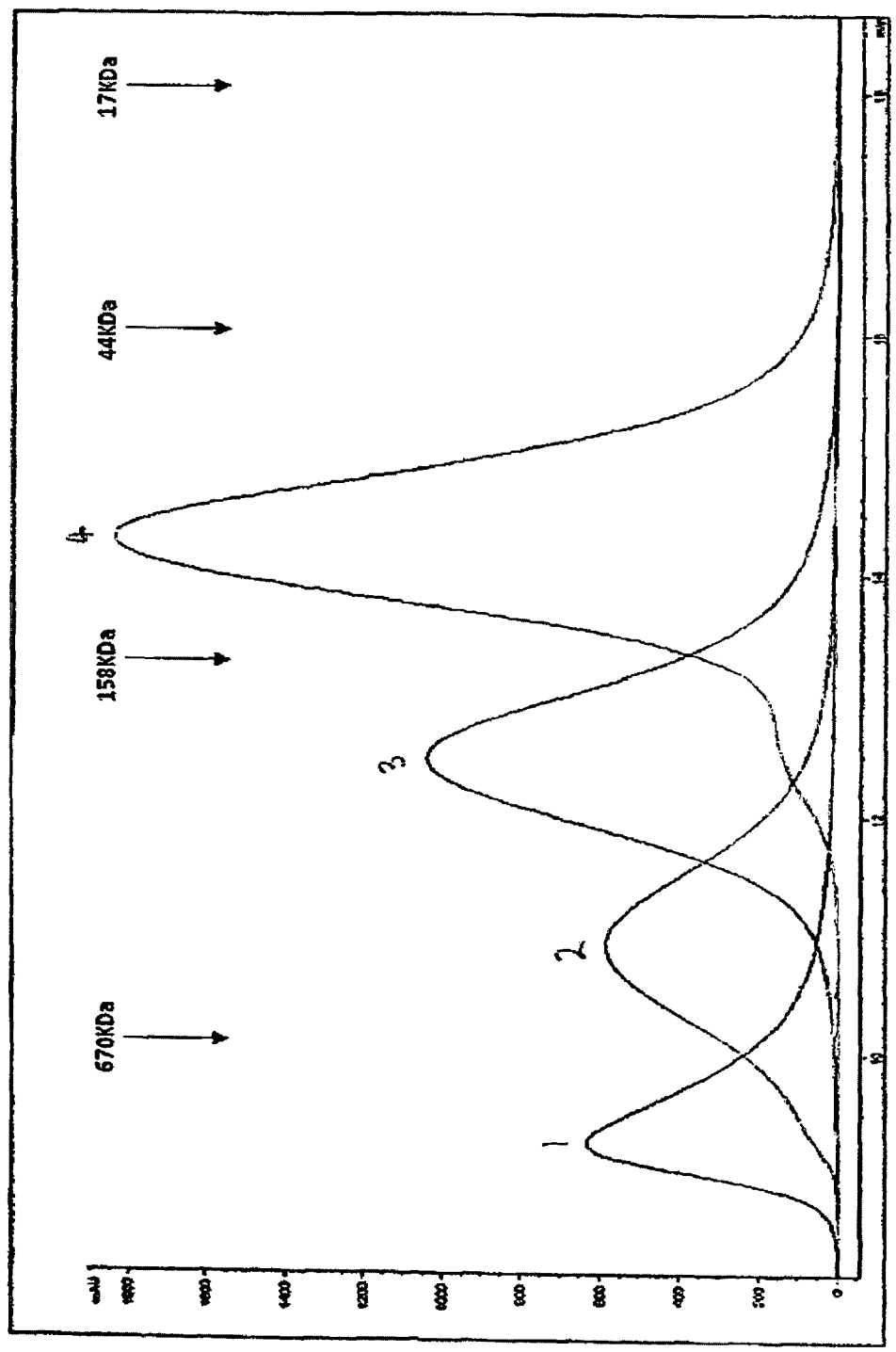
Figure 22:
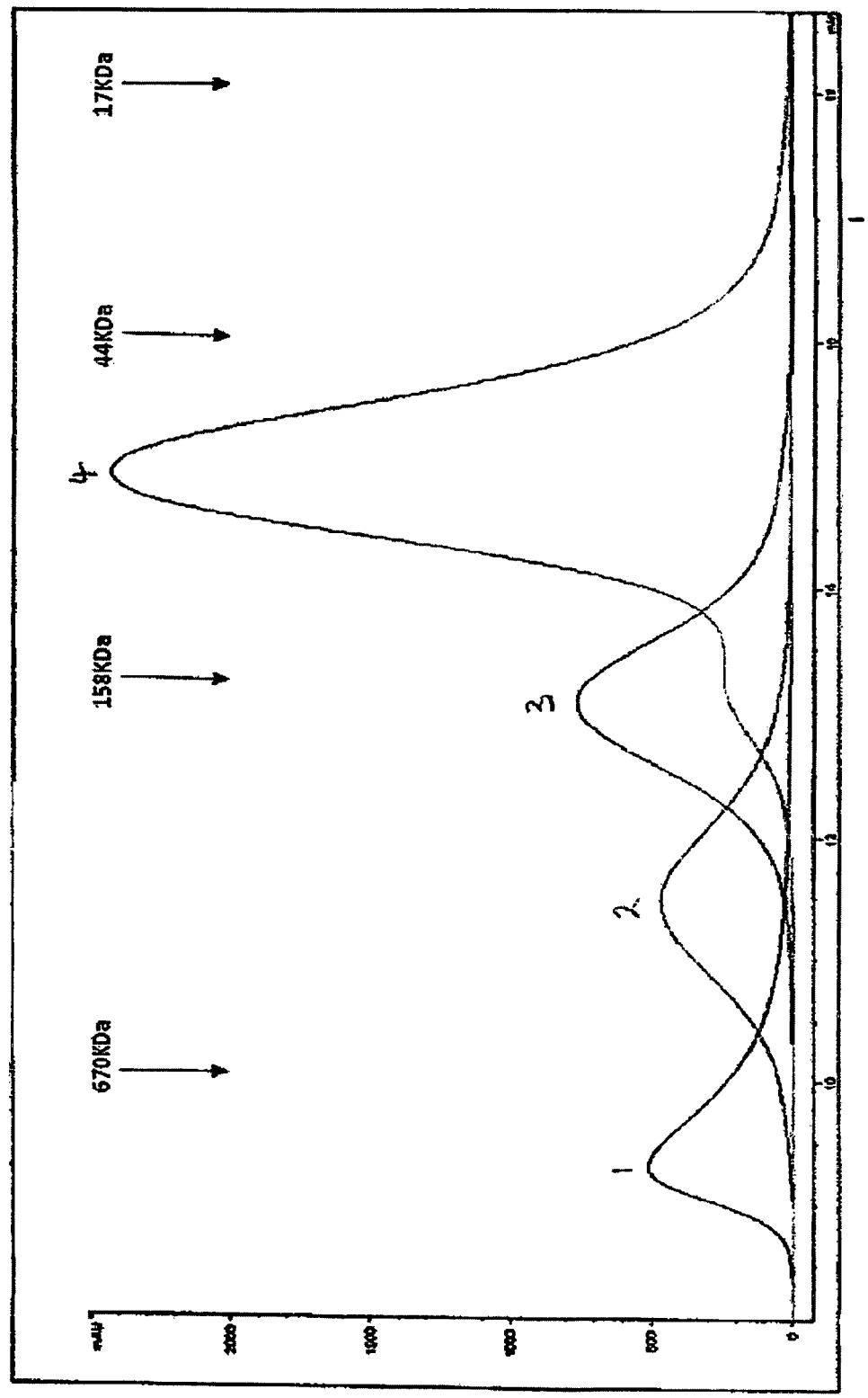

The pooled fractions corresponding to each of peaks 1-4 were examined on an analytical gel filtration column for WT $E2_{661}$-his (FIG. 21) and $\Delta 123$ $E2_{661}$-his (FIG. 22). Individual runs for peaks 1-4 were overlaid into a single FIGURE to show their relative elution times. The elution times of molecular weight standards are indicated above the chromatogram.

Figure 23:
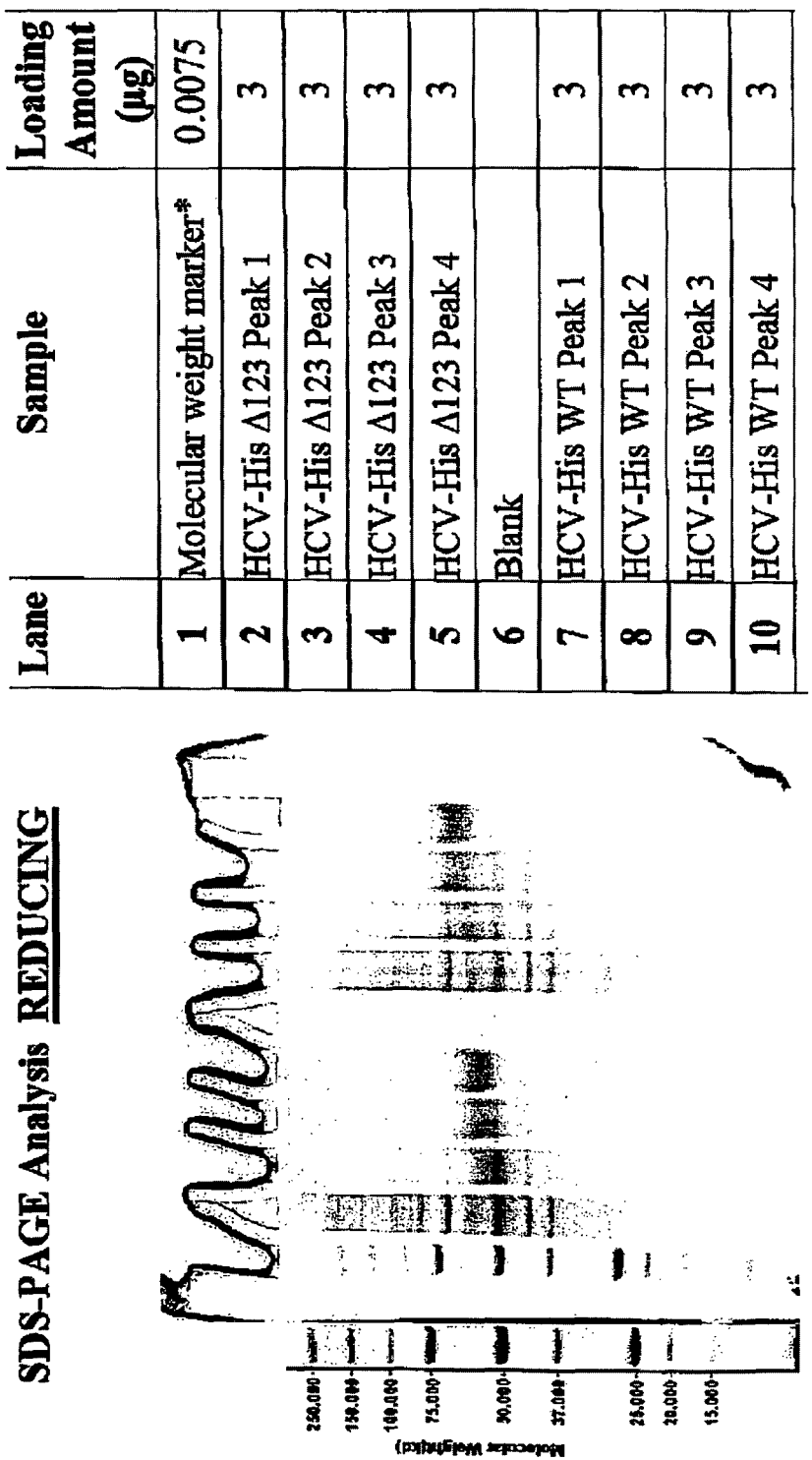
Figure 24:
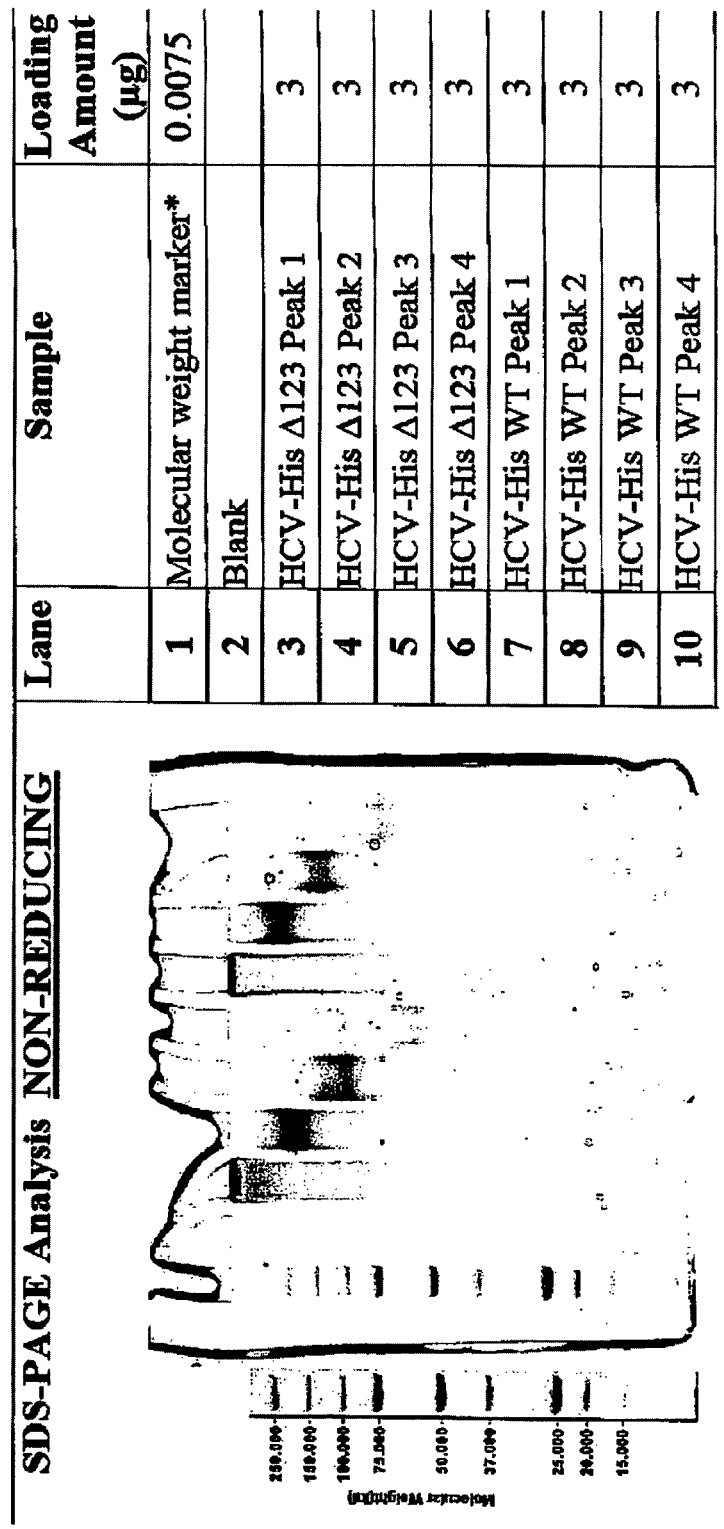

The gel filtration purified forms of WT $E2_{661}$-his and $\Delta 123$ $E2_{661}$-his proteins were analysed by SDS-PAGE under reducing (FIG. 23) and non-reducing conditions (FIG. 24). Under reducing conditions, peak 4 WT $E2_{661}$-his and $\Delta 123$ $E2_{661}$-his migrated as a broad band of approximately 55-65 kDa and 50-60 kDa, respectively (FIG. 23). Under non reducing conditions the majority of peak 4 WT $E2_{661}$-his and $\Delta 123$ $E2_{661}$-his migrated as a broad band of approximately 55-65 kDa and 50-60 kDa, respectively, consistent with a monomeric form of protein containing 1 unit of WT $E2_{661}$-his and $\Delta 123$ $E2_{661}$-his (FIG. 24). A small amount of an ~100 kDa protein was present consistent with the molecular mass expected for dimeric protein (2 units). The broad bands observed are consistent with heterogeneous N-linked glycosylation at 11 and 9 sites for WT $E2_{661}$-his and $\Delta 123$ $E2_{661}$-his, respectively. The monomeric forms of $E2_{661}$-his were largely devoid of other (non-$E2_{661}$-his) contaminating proteins and estimated to be >95% pure.

Under reducing conditions WT $E2_{661}$-his and $\Delta 123$ $E2_{661}$-his peak 3 migrated at ~55-65 kDa and 50-60 kDa, respectively. The average migration of peal 3 proteins in reducing SDS-PAGE was somewhat faster, suggesting these proteins are smaller in molecular mass than the corresponding monomeric forms observed in peak 4. This may be indicative of lower levels of protein glycosylation (FIG. 23). A higher molecular weight form of WT $E2_{661}$-his and $\Delta 123$ $E2_{661}$-his proteins was also apparent, migrating at approximately 100 kDa and corresponding in molecular weight to dimeric $E2_{661}$-his. Under non-reducing conditions, the majority of peak 3 proteins migrated at the expected molecular mass of ~100 kDa consistent with a dimeric form of $E2_{661}$-his (2 units) with a small amount of monomeric $E2_{661}$-his protein present (FIG. 24).

Under reducing conditions, WT $E2_{661}$-his and $\Delta 123$ $E2_{661}$-his peak 2 migrated at ~55-65 and 50-60 kDa, respectively. The average migration of peak 2 proteins in reducing SDS-PAGE was somewhat faster, suggesting these proteins are smaller in molecular mass than the corresponding monomeric forms observed in peak 4. This may be indicative of lower levels of protein glycosylation in peak 2 proteins (FIG. 23). Under non-reducing conditions, the majority of WT $E2_{661}$-his and $\Delta 123$ $E2_{661}$-his peak 2 proteins migrated at ~170 kDa and 160 kDa, respectively, consistent with the presence of at least 3 units of $E2_{661}$-his. A small amount of contaminating 100 kDa dimeric $E2_{661}$-his was present in both WT $E2_{661}$-his and $\Delta 123$ $E2_{661}$-his (FIG. 24).

The migration of the WT $E2_{661}$-his and $\Delta 123$ $E2_{661}$-his peak 1 in reducing SDS-PAGE revealed a heterogeneous range of protein species ranging from 20 kDa to 250 kDa (FIG. 23). Under non reducing conditions, the majority of peak 1 protein remained at the interface between the stacking and resolving gel suggesting the molecular mass of the non reduced form of this species is >300 kDa and contains 4 or more units of $E2_{661}$-his (FIG. 24). However, a considerable amount of contaminating protein was observed as a smear ranging from 20-250 kDa.

To analyse which of the protein species corresponded to $E2_{661}$-his protein in each of peaks 1-4, 0.5 µg of each protein was loaded onto 4-12% Nu-PAGE gels and run under reducing conditions before transfer to PVDF membrane. Blots were probed with either Penta-His antibody specific to the C-terminal 6×His epitope tag (FIG. 25) or to an epitope present within E2 residues 411-428 (FIG. 26). Results show that the penta-His antibody detected the $E2_{661}$-his protein species in each of fraction 1-4 migrating at approximately 50-60 kDa. Lower reactivity was present towards peak 1 protein. Dimeric forms of peak 2 and 3 were also present (FIG. 25).

The anti-E2 antibody detected $E2_{661}$-his protein in each of peaks 1-4 (FIG. 26). The majority of protein in peak 4 was 50-60 kDa species with a small amount of ~100 kDa species detected. Peak 3 contained 50-60 kDa species and 100 kDa forms of $E2_{661}$-his protein. Peak 2 contained 50-60 kDa species, and a broad smear of proteins ranging from 100-200 kDa. Peak 1 contained 50-60 kDa species of $E2_{661}$-his as well as higher molecular weight forms ranging from 100 to >200 kDa.

Example 10

Guinea Pig Vaccination with WT $E2_{661}$-his and $\Delta 123$ $E2_{661}$-his Proteins Guinea Pigs were vaccinated with 100 µg $\Delta 123$ $E2_{661}$-his of either unfractionated, or peak 1, 2, 3 or 4 protein mixed with 75 ISCO™ units (IU) ISCOMATRIX™ adjuvant three times at three weekly intervals. Final bleeds were performed two weeks after the final vaccination. Alternatively, guinea pigs received 100 µg unfractionated, or peak 1, 2, 3 or 4 WT $E2_{661}$-his protein mixed with 75 IU ISCOMATRIX™ adjuvant three times at two weekly intervals with the final bleed one week after the last immunization.

Example 11

Antibody Responses in Guinea Pigs to Homologous Fractions of WT $E2_{661}$-his and $\Delta 123$ $E2_{661}$-his Proteins The immune serum derived from animals vaccinated with one of WT $E2_{661}$-his peaks 1-4 and the unfractionated material were examined for their ability to bind to homologous antigen in a solid-phase enzyme immune assay. Microtitre plates were coated with GNA lectin and homologous immunizing antigen followed by blocking of unoccupied sites with BSA and addition of serial dilutions of immune serum. Bound immunoglobulins were detected with anti-guinea pig immungloubulins coupled to horse-radish peroxidase and visualised with TMB substrate.

The results (FIG. 27) show that animals vaccinated with peak 1 and peak 2 proteins elicited the highest mean titres of antibody reactive to homologous antigen. Animals vaccinated with peak 3 and 4 proteins elicited the lowest mean titres of antibody and were lower than the mean titres of antibody elicited in the unfractionated immune group.

The immune sera obtained from guinea pigs vaccinated with $\Delta 123$ $E2_{661}$-his proteins peaks 1-4 or the unfractionated mixture were compared for their reactivity to homologous immunizing antigen in a solid phase enzyme immunoassay. Microtitre plates were coated with GNA lectin and homologous immunizing antigen followed by blocking of unoccupied sites with BSA and addition of serial dilutions of immune serum. Bound immunoglobulins were detected with anti-guinea pig immunoglobulins coupled to horse-radish peroxidase and visualised with TMB substrate.

Figure 28:
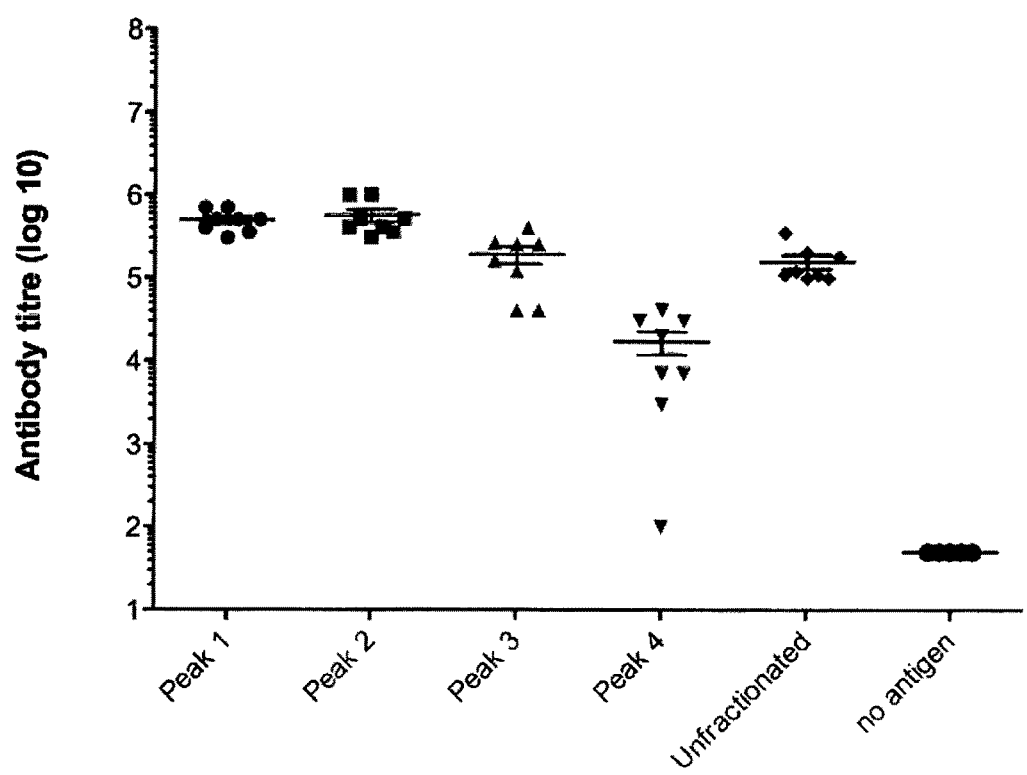

The results (FIG. 28) reveal that the highest titre of antibody was elicited in guinea pigs that received peak 1 and peak 2 Δ123 E2$_{661}$-his proteins. Mean antibody titres between peak 1 and peak 2 immunogen groups were similar. The lowest mean titres of antibody were elicited by peak 4 protein with mean antibody titres at least 20 times lower than those obtained using peak 1 or 2, 10 times lower than peak 3 and 8 times lower than the unfractionated mixture. Mean antibody titres obtained using the unfractionated mixture were similar to those obtained using peak 3 as the immunogen. This result shows that the majority of the immunogenicity present in the unfractionated mixture can be attributed to the form of E2$_{661}$-his protein present in peak 1 and peak 2 that is comprised of trimeric and/or higher order forms of Δ123 E2$_{661}$-his.

Example 12

Antibody Reactivity to Unfractionated WT and Δ123 E2$_{661}$-his Proteins

The immune sera from guinea pigs vaccinated with one of Δ123 E2$_{661}$-his peaks 1-4 or the unfractionated mixture were examined for their ability to bind to unfractionated preparations of homologous H77c derived WT and Δ123 E2$_{661}$-his in a solid phase immunoassay. Use of WT unfractionated protein as an antigen in immunoassay allows a comparison of the total levels of antibody induced to a standardized antigen. Use of the Δ123 form of E2$_{661}$-his as a coating antigen in enzyme immunoassay allows an examination of the total immune response to the most conserved regions of E2. Microtitre plates were coated with GNA lectin followed WT or Δ123 E2$_{661}$-his proteins. Unoccupied sites were blocked with BSA before addition of serial dilutions of immune serum. Bound immunoglobulins were detected with anti-guinea pig immunoglobulins coupled to horse-radish peroxidase and visualised with TMB substrate.

Figure 29:
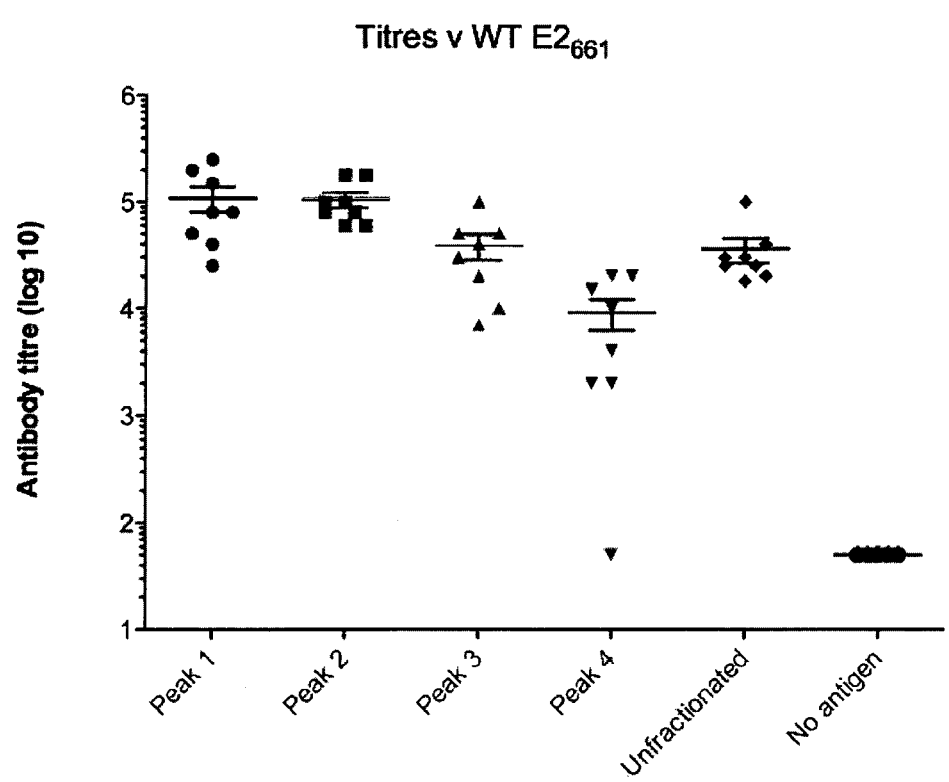
Figure 29:
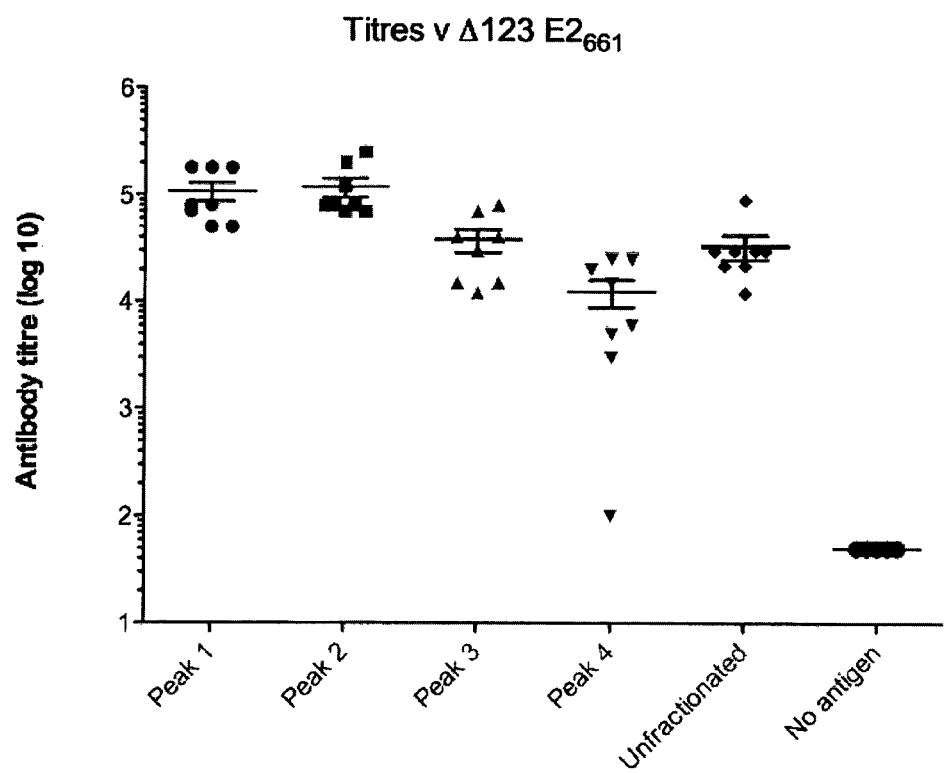

The results (FIG. 29) show that animals vaccinated with peak 1 and 2 proteins elicited the highest mean titres of antibody reactive towards homologous WT (A) and Δ123 E2$_{661}$-his (B) proteins. Animals vaccinated with peak 3 protein or the unfractionated immune serum elicited similar antibody mean titres reactive towards unfractionated WT (A) or Δ123 E2$_{661}$-his (B). Animals vaccinated with peak 4 protein elicited the lowest mean titres of antibody. The immune serum obtained from animals vaccinated with Δ123 E2$_{661}$-his showed similar reactivity towards unfractionated WT and Δ123 E2$_{661}$-his proteins. The ability of the immune serum from each immune group to bind similarly to the homologous immunizing antigen (FIG. 28) and the unfractionated mixture of E2$_{661}$-his proteins (FIG. 29) confirms that the antibodies are specific to E2$_{661}$-his proteins.

Example 13

Ability of Serum from Vaccinated Guinea Pigs to Inhibit the Interaction Between E2 and a Recombinant Form of the Primary HCV Cellular Receptor CD81

The immune sera from guinea pigs vaccinated with one of WT E2$_{661}$-his peaks 1-4 or the unfractionated mixture were examined for the ability to block the binding between homologous H77c E2$_{661}$-his and a recombinant form of the primary cellular receptor for HCV CD81. In this assay, the total amount of antibody present in the immune serum that can bind epitopes present on the E2$_{661}$ antigen and thereby prevent its interaction with recombinant CD81 is measured. Using the homologous E2$_{661}$-his protein determines the total E2-CD81 blocking antibodies elicited, whilst the use of a heterologous sequence of E2$_{661}$-his antigen measures the degree of cross-reactivity of the antibody response towards dissimilar E2 antigens and the ability of this cross reactive antibody to prevent interaction between E2 and CD81. Serial dilutions of immune serum were added to unfractionated H77c E2$_{661}$-his before addition to MBP-LEL$^{113-201}$ coated enzyme immunoassay plates. Bound E2$_{661}$-his was detected with anti-his antibody, anti-rabbit horse radish peroxidase coupled immunoglobulins and TMB substrate.

The results (FIG. 30 A) show that the animals vaccinated with WT E2$_{661}$-his peak 2 protein elicited the highest mean titres of homologous E2-CD81 inhibition antibodies (mean titre 344). Animals vaccinated with peak 1 and the unfractionated protein elicited the lowest mean titres of E2-CD81 inhibition antibodies (mean titre 18 and 18, respectively). Immunization with the fractionated peak 2-4 proteins elicited higher mean titres of E2-CD81 inhibition antibodies than the unfractionated WT E2$_{661}$-his antigen.

The ability of WT E2$_{661}$-his antibodies to inhibit the binding of a heterologous form of unfractionated WT E2$_{661}$-his to bind CD81 (FIG. 30 B) was then examined. The JFH1 E2 protein differs from H77c at 31% of amino acids across the entire E2 region. The ability of the immune serum to prevent the interaction of a heterologous E2 protein with CD81 can be seen as a measure of the breadth of the antibody response towards diverse E2 sequences. Peak 2 WT E2$_{661}$-his immune serum had the highest mean titres of heterologous E2-CD81 inhibition antibody (mean 77). Three animals vaccinated with peak 3 proteins also elicited heterologous E2-CD81 inhibition antibodies. Animals that received peak 1 proteins and the unfractionated material did not elicit antibody capable of blocking heterologous E2 from binding CD81.

The immune serum from guinea pigs vaccinated with one of Δ123 E2$_{661}$-his peaks 1-4 or unfractionated Δ123 E2$_{661}$-his protein was examined for the ability to block the binding between homologous H77c E2$_{661}$-his and a recombinant form of the primary cellular receptor for HCV CD81. Serial dilutions of immune serum were added to unfractionated H77c E2$_{661}$-his before addition to MBP-LEL113-201 coated enzyme immunoassay plates. Bound E2$_{661}$-his was detected with anti-his antibody, anti-rabbit horse radish peroxidase coupled immunoglobulins and TMB substrate.

The results (FIG. 31 A) show that the highest mean titres of homologous E2-CD81 inhibition antibody were elicited in animals vaccinated with Δ123 E2$_{661}$-his peak 2 protein (mean 940). The 50% E2-CD81 inhibition titre elicited in animals vaccinated with peaks 1, 3 or 4 were 2 to 3 fold higher than the unfractionated immune group.

The ability of the Δ123 E2$_{661}$-his antibodies to inhibit the binding of a heterologous form of unfractionated E2$_{661}$-his to bind CD81 was then examined (FIG. 31 B). Animals vaccinated with Δ123 E2$_{661}$-his peak 2 proteins elicited the highest mean titres of antibody capable of inhibiting heterologous E2$_{661}$-his binding to CD81 with a mean titre of 256. The animals that received peak 4 (monomeric E2) proteins elicited the lowest mean titres of heterologous E2-CD81 inhibition antibody (mean titre 26). Animals that received peak 1, 3 or the unfractionated mixture had intermediate mean titres of antibody capable of inhibiting heterologous E2$_{661}$-his binding to CD81 (55, 77 and 45, respectively).

Example 14

Homologous Neutralizing Antibody Responses in Guinea Pigs Vaccinated with Δ123 E2$_{661}$-his Proteins The immune sera from guinea pigs vaccinated with one of Δ123 E2$_{661}$-his peaks 1-4 or the unfractionated mixture were examined for their ability to neutralize pseudotyped retroviral particles containing the homologous H77c E1E2 glycoproteins (H77c HCVpp). This experiment determines the total amount of antibody elicited by animals from each of the immune groups that is able to prevent viral infection in vitro in virion preparations using the same (homologous) HCV glycoproteins as represented in the sequence of the immunizing antigen. Such antibodies are deemed to be functional as they can prevent the virus from entering liver cells in vitro. The specificity of neutralizing antibodies is not restricted to only those antibodies able to inhibit E2 binding to CD81. Heat inactivated immune serum was serially diluted in DMF10 and incubated with an equal volume of H77c HCVpp for 1 h at 37° C. before addition to Huh 7.5 cells seeded the day prior at 3×10$^4$ cells/well. After 3 days, luciferase activity in cell lysates was measured in a luminometer.

Figure 32:
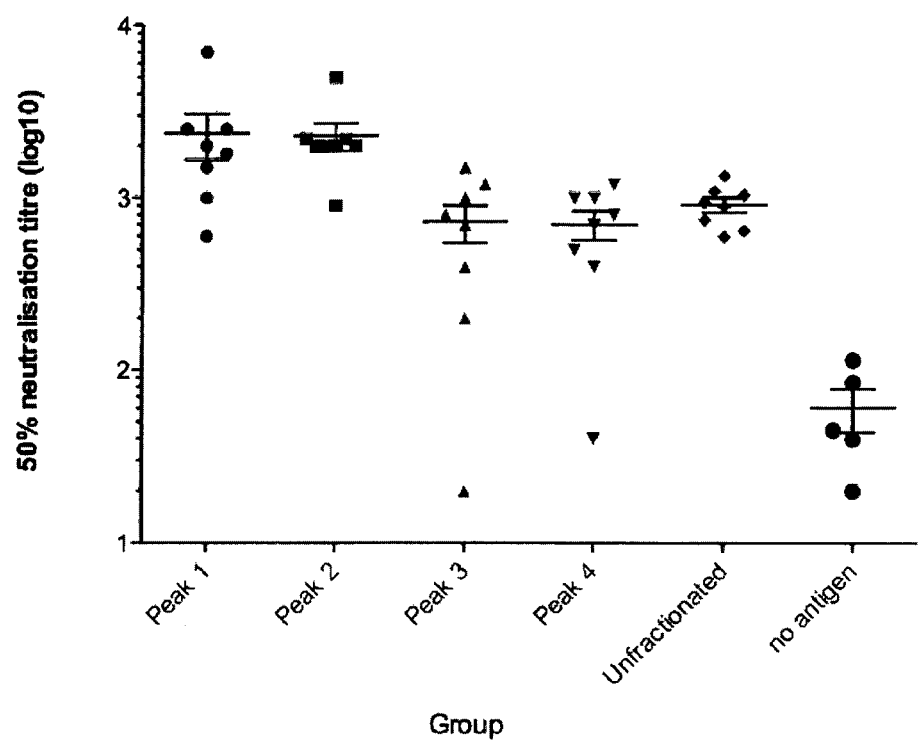
Figure 32:
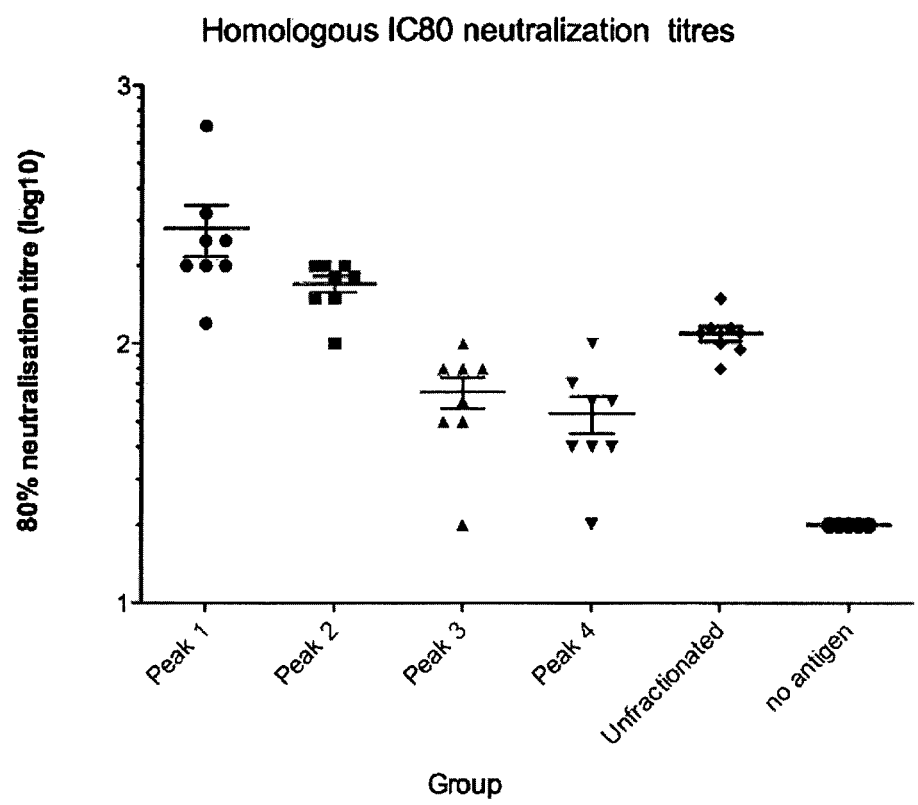

The results (FIG. 32) show that guinea pigs vaccinated with peak 1 or peak 2 proteins elicited the highest mean titres antibody capable of blocking (neutralizing) 50% of homologous viral entry (IC50) (FIG. 32 top). The mean IC50 titres were similar in peak 1 (mean 2363) and peak 2 immune serum groups (mean 2288). Guinea pigs vaccinated with peaks 3 or 4 proteins elicited the lowest 50% homologous neutralizing antibody responses (mean 727 and 705, respectively) and were similar to the unfractionated immune group (mean titre 918).

Measurement of the ability of the antibody to block 80% of homologous viral entry indicate that animals vaccinated with peak 1 or peak 2 proteins elicited higher mean titres than all other groups (FIG. 32 B) with mean IC80 mean titres of 280 and 170. IC80 mean titres induced by the unfractionated mixture (mean 109) were higher than those induced by peak 3 (mean 65) and peak 4 (mean 54) antigens.

Example 15

Heterologous (Cross-) Neutralizing Antibody Responses in Guinea Pigs Vaccinated with Δ123 E2$_{661}$-his Proteins Immune sera from guinea pigs vaccinated with Δ123 E2$_{661}$-his proteins were examined for their ability to cross-neutralize heterologous J6/JFH1 chimeric genotype 2a cell culture (HCVcc) derived virus. This experiment determines the total amount of antibody elicited by animals from each of the immune groups that are able to prevent viral infection in vitro using an HCV strain encoding highly divergent (heterologous) HCV glycoproteins compared to the sequence of the immunizing antigen. Such antibodies are deemed to be functional and cross neutralizing as they can prevent a genetically divergent virus from entering liver cells in vitro. Heat inactivated immune serum was serially diluted and mixed with an equal volume of HCVcc. Serum/virus mixtures were applied to Huh 7.5 cells and incubated at 37° C. before removal and incubation for 44 h in tissue culture media. Luciferase activity present in the tissue culture fluid was measured using the Renilla luciferase substrate and a luminometer.

Figure 33:
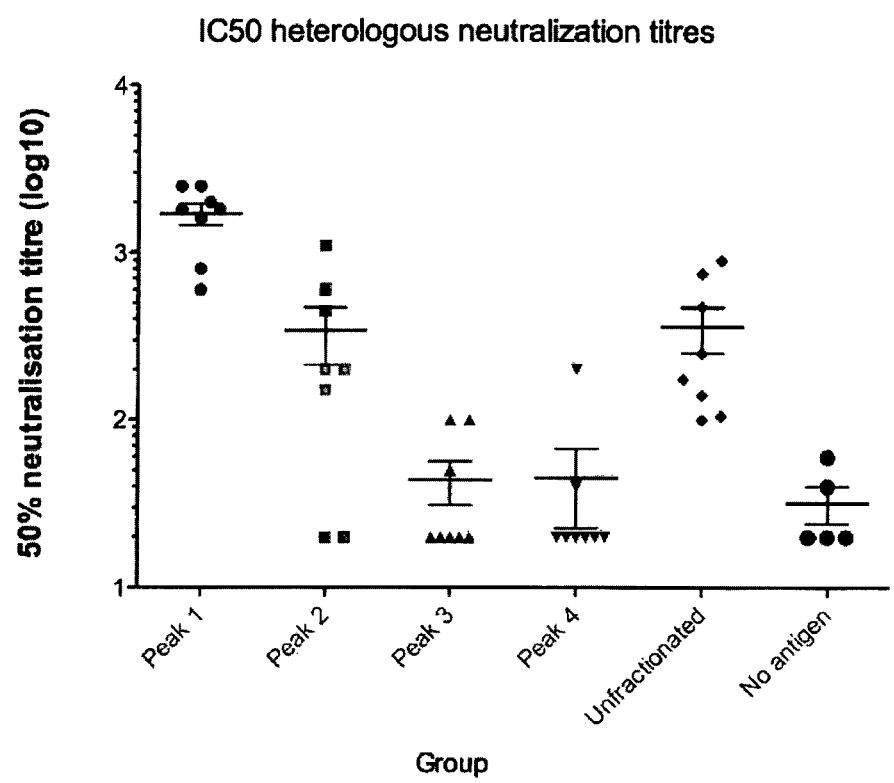
Figure 33:
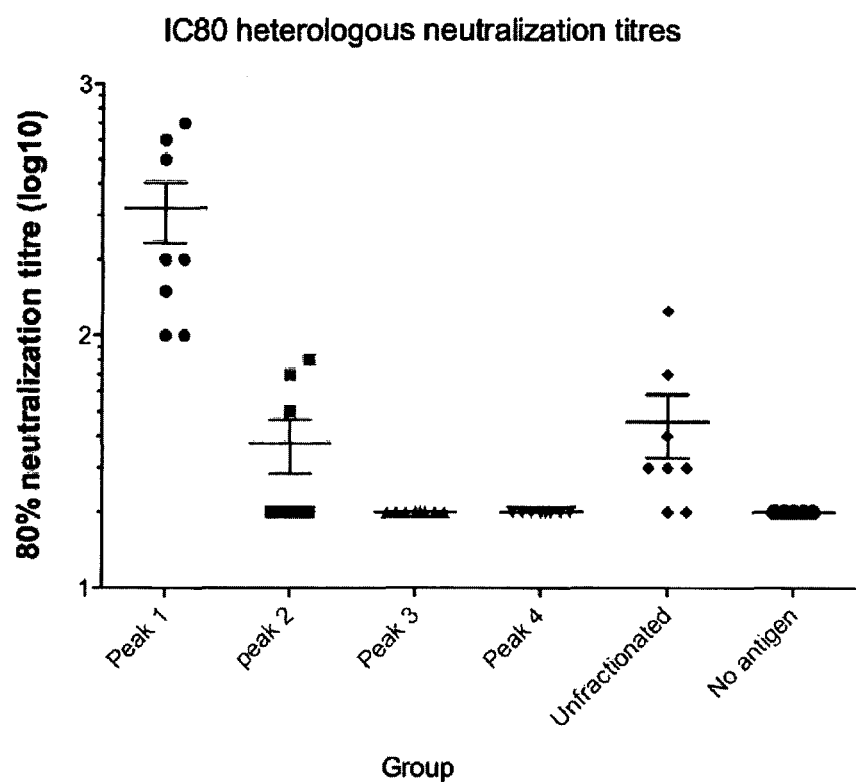

The results show that animals vaccinated with unfractionated Δ123 E2$_{661}$-his protein elicited antibody capable of neutralizing 50% of the infectious virus dose of virus (IC50) with a mean of 360 and a range between 100 to 900 (FIG. 33 A). Two animals vaccinated with ISCOMATRIX™ adjuvant alone had mean 50% neutralization mean titres of 40 and 60 with the other three animals failing to neutralize 50% or more of the infectious virus.

Animals vaccinated with Peak 1 Δ123 E2$_{661}$-his protein elicited the highest mean titres of cross neutralizing antibodies with a mean IC50 of 1700 (FIG. 33 A). Animals vaccinated with Peak 2 Δ123 E2$_{661}$-his and the unfractionated immune group elicited similar mean titres of cross neutralizing antibodies of 340 and 362, respectively. Animals vaccinated with peak 3 or 4 proteins failed to elicit significant mean titres of cross-neutralizing antibodies.

All animals vaccinated with Peak 1 protein were able to neutralize 80% of the infectious dose of virus with a mean titre of 320 and a range of 100-700. The mean IC80 mean titres of animals vaccinated with peak 2 protein (mean 38) was similar to the unfractionated mixture (mean 46) (FIG. 33 B). None of the animals in peak 3 or 4 immune groups were able to neutralize 80% of the infectious dose of heterologous virus.

Example 16

Reactivity of WT E2$_{661}$-his Immune Serum to H77c WT and Δ123 Antigens

The ability of immune serum obtained from guinea pigs vaccinated with one of H77c WT E2$_{661}$-his protein peaks 1-4 or the unfractionated mixture to bind the unfractionated H77c WT E2$_{661}$-his antigen and Δ123 E2$_{661}$-his antigen were compared in an enzyme immunoassay. Use of WT unfractionated protein as an antigen in immunoassay allows a comparison of the total levels of antibody induced to a standardized antigen. Use of the Δ123 form of E2$_{661}$ as a coating antigen in enzyme immunoassay allows an examination of the total immune response to the most conserved regions of E2. Microtitre plates were coated GNA lectin and unfractionated H77c antigen followed by blocking of unoccupied sites with BSA and addition of serial dilutions of immune serum. Bound immunoglobulins were detected with anti-guinea pig immunoglobulins coupled to horse-radish peroxidase and visualised with TMB substrate.

Figure 34:
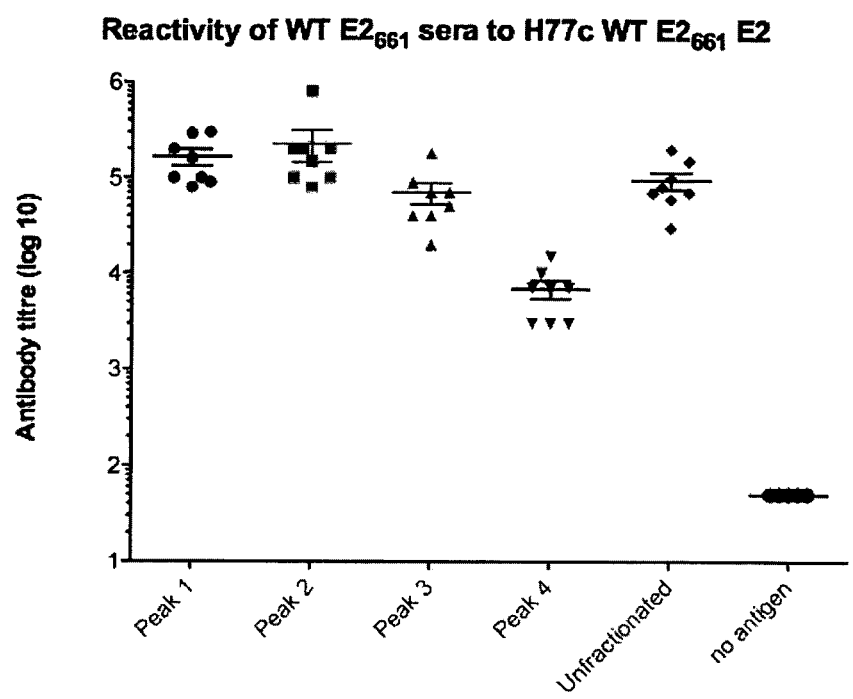
Figure 34:
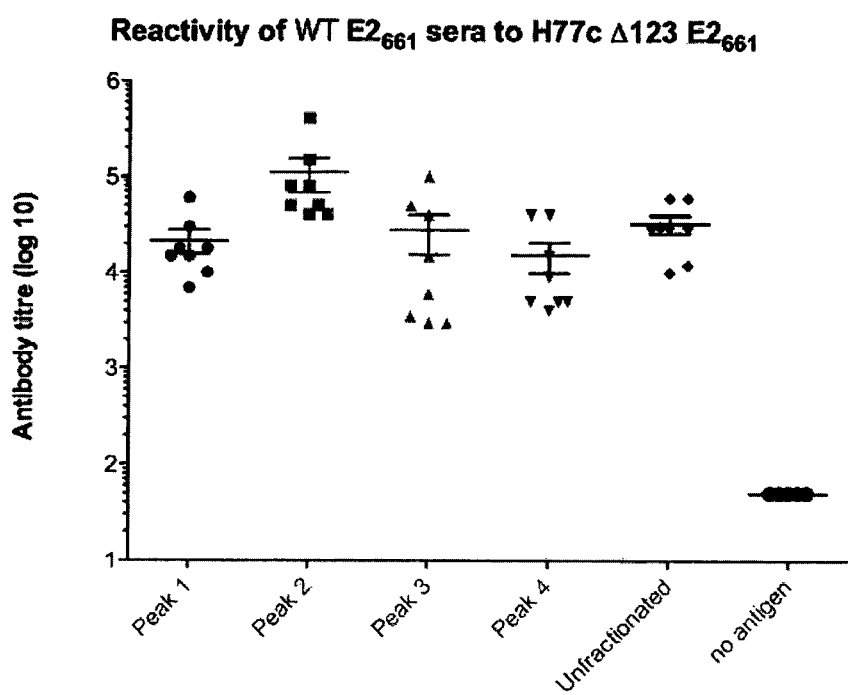

The results show that animals vaccinated with peak 1 and 2 WT H77c E2$_{661}$-his proteins elicited the highest mean titres of antibodies reactive to unfractionated H77c E2$_{661}$-his antigens and were significantly higher than animals that were immunized with unfractionated WT E2$_{661}$-his (FIG. 34 A). Animals vaccinated with peak 4 proteins elicited the lowest mean titres of antibodies reactive to unfractionated WT H77c E2$_{661}$-his. Animals vaccinated with peak 3 protein and the unfractionated immune group elicited similar mean titres of antibody, however, the mean antibody titres were lower than those in peak 1 and 2 immune sera but higher than the peak 4 immune group. The ability of the immune serum from each immune group to bind similarly to the homologous immunizing antigen (FIG. 27) and the unfractionated mixture of E2$_{661}$-his proteins (FIG. 34) confirms that the antibodies are specific to E2$_{661}$-his proteins.

Comparison of the ability of the immune serum from WT E2$_{661}$-his vaccinated animals to bind unfractionated H77c Δ123 antigen revealed lower overall antibody reactive to the core domain of E2 lacking all three variable regions. Peak 2 immune serum generated the highest mean titres of antibody reactive to the core domain of E2. All other groups elicited similar mean titres of antibody reactive to the core domain of E2 (FIG. 34 B).

Example 17

Cross Reactivity of WT $E2_{661}$-his Immune Serum to JFH1 WT and Δ123 Antigens

The ability of immune serum obtained from guinea pigs vaccinated with one of H77c WT $E2_{661}$-his protein peaks 1-4 or unfractionated mixture to cross-react with the unfractionated mixtures of JFH1 WT $E2_{661}$-his antigen and Δ123 $E2_{661}$-his antigen were compared in an enzyme immunoassay. Use of WT unfractionated protein derived from a divergent strain of HCV as an antigen in immunoassay allows a comparison of the total levels of cross-reactive antibody induced to a standardized antigen. Use of the Δ123 form of heterologous $E2_{661}$-his as a coating antigen in enzyme immunoassay allows an examination of the total cross-reactive immune response to the most conserved regions of that divergent strain of E2. The genotype 2a JFH1 E2 sequence is one of the most divergent sequences from that of the genotype 1a H77c E2 sequence; H77c E2 and JFH1 E2 differ by 31% in the intact form of $E2_{661}$ and differ by 20% in the core domain of E2 lacking the three variable regions. Microtitre plates were coated with GNA lectin and unfractionated antigen followed by blocking of unoccupied sites with BSA and addition of serial dilutions of immune serum. Bound immunoglobulins were detected with anti-guinea pig immunoglobulin's coupled to horse-radish peroxidase and visualised with TMB substrate.

The results show that the mean antibody titre in animals vaccinated with peak 2 WT H77c $E2_{661}$-his protein was 4-fold higher towards unfractionated WT JFH1 $E2_{661}$-his antigens compared to the mean titres of the other immune groups (FIG. 35 A). Animals vaccinated with peak 4 monomeric protein elicited the lowest mean titres of cross-reactive antibody and were 5 fold lower than the unfractionated immune group. Animals vaccinated with peak 1 and 3 proteins elicited similar mean titres of cross-reactive antibody to each other and to the unfractionated immune group.

Examination of the ability of the immune serum to cross-react with the JFH1 E2 core domain (Δ123) revealed that peak 2 immune serum elicited 4 fold higher mean titres of antibody compared to peak 1, 3 and 4 immune groups (FIG. 35 B). Monomeric peak 4 protein elicited the lowest mean titres of antibody cross reactive to the Δ123 core domain of JFH1 compared to all other immune groups being at least 3 fold lower. (FIG. 35 B).

Example 18

Neutralization of Homologous Virus by WT Immune Serum Groups

Immune sera elicited by guinea pigs vaccinated with one of WT $E2_{661}$-his protein peaks 1-4 or unfractionated mixture were examined for their ability to neutralize pseudotyped retroviral particles containing the homologous H77c E1E2 glycoproteins (H77c HCVpp). This experiment determines the total amount of antibody elicited by animals from each of the immune groups that is able to prevent viral infection in vitro in virion preparations expressing the same (homologous) HCV glycoproteins as represented in the sequence of the immunizing antigen. Such antibodies are deemed to be functional as they can prevent the virus from entering liver cells in vitro. Heat inactivated immune serum was serially diluted in DMF10 and incubated with an equal volume of H77c HCVpp for 1 h at 37° C. before addition to Huh 7.5 cells seeded the day prior at $3 \times 10^4$ cells/well. After 3 days, luciferase activity in cell lysates was measured in a luminometer.

The results show that immune serum from animals that received peak 1, 2, 3 and the unfractionated mixture had mean titres of antibody capable of neutralizing 50% of the infectious dose of virus that were well above those of the no antigen immune group. (FIG. 36 A). Animals that received monomeric peak 4 protein had similar mean neutralizing antibody titres to the no antigen immune group. Similar mean titres of antibody capable of mediating 50% neutralization of homologous virus were elicited by peak 1 and 2 immune groups (mean 2150 and 1600, respectively) and these were higher than the peak 3 (mean 1175) and unfractionated immune groups (mean 1013).

Within each of the peak 2 and unfractionated immune group, three animals appeared to elicit significantly lower mean titres of neutralizing antibody and are outliers. These sera displayed aberrant characteristics and repeat assays may reveal the presence of higher mean titres of neutralizing antibody. Removal of the outliers from the analysis reveals that peak 2 induced mean 50% neutralization titres of 2460 while the unfractionated immune groups mean IC50 titre was 1500.

Only animals in peak 1, 2, 3 and the unfractionated immune group elicited antibody capable of inhibiting 80% of the infectious dose of homologous virus (FIG. 36 B). Peak 1 immune serum elicited higher mean 80% neutralization titres compared to all other immune groups with a mean titre of 225. Mean IC80 titres in peak 2 immune group including outliers was 116 while excluding the three outliers elevated the mean titre to 174. The unfractionated and peak 3 immune groups elicited similar IC80 mean titres of 86. Exclusion of the three outliers from the unfractionated immune group elevated the mean IC80 titre to 126. The data show that peak 1, 2 and 3 are the preferred immunogens for eliciting neutralizing antibody using WT E2 as the immunogen.

Example 19

Cross Neutralization of Genotype 2a Cell Culture Derived HCV

Immune sera elicited by guinea pigs vaccinated with one of WT $E2_{661}$-his protein peaks 1-4 or unfractionated mixture were examined for their ability to neutralize heterologous J6/JFH1 chimeric genotype 2a cell culture (cc) derived HCV. This experiment determines the total amount of antibody elicited by animals from each of the immune groups that is able to prevent viral infection in vitro using an HCV strain encoding highly divergent (heterologous) HCV glycoproteins compared to the sequence of the immunizing antigen. Such antibodies are deemed to be functional and cross neutralizing as they can prevent a genetically divergent virus from entering liver cells in vitro. Heat inactivated immune serum was serially diluted in DMF10+NEAA and mixed with an equal volume of 3.16 $TCID_{50}$/ml HCVcc for 20 min at 37° C. Serum/virus mixtures were applied to Huh 7.5 cells seeded the day prior at $8 \times 10^3$ cells/well and incubated for 5 h at 37° C. Serum/virus mixtures were removed and washed 4 times with PBS before addition of DMF10+NEAA and incubation for 44 h. Luciferase activity present in the tissue culture fluid was measured using the *Renilla* luciferase substrate and a luminometer.

Animals vaccinated with peak 1 and 2 WT proteins elicited higher IC50 mean titres of cross-neutralizing antibody compared to other immune groups with mean titres of 155 and 368, respectively (FIG. 37 A). The lowest mean titres of antibody capable of mediating 50% neutralization of a heterologous strain of HCV were elicited by peak 3 and 4 (mean 34 and 39, respectively) and the unfractionated proteins elicited a mean IC50 titre of 48 (FIG. 37 A).

Only a small number of animals vaccinated with peak 1, 2 and the unfractionated proteins elicited antibody capable of neutralizing 80% of the infectious dose (FIG. 37 B). Five animals in immune group peak 1, two in peak 2, and three in the unfractionated group possessed IC80 mean titres (FIG. 37 B) and the mean titres were similar (38, 27 and 30, respectively). The mean titres of the responding animals in peak1, 2 and the unfractionated immune groups were 48, 50 and 47, respectively. These results show that peak 1 and 2 are the preferred immunogens for eliciting cross-neutralizing antibodies using WT $E2_{661}$ as an immunogen.

Example 20

Cross-Reactivity of Wild Type Immune Serum to Con1 WT and Δ123 $E2_{661}$ Antigens The ability of immune serum obtained from guinea pigs vaccinated with one of H77c WT $E2_{661}$-his protein peaks 1-4 or unfractionated mixture to cross-react with the unfractionated mixtures of genotype 1b Con1 WT $E2_{661}$-his antigen and Δ123 $E2_{661}$-his antigen were compared in an enzyme immunoassay. Use of WT unfractionated protein derived from a divergent strain of HCV as an antigen in immunoassay allows a comparison of the total levels of cross-reactive antibody induced to a standardized antigen. Use of the Δ123 form of heterologous $E2_{661}$ as a coating antigen in enzyme immunoassay allows an examination of the total cross-reactive immune response to the most conserved regions of that divergent strain of E2. The genotype 1b Con1 E2 sequence is less divergent from that of the genotype 1a H77c E2 sequence compared to JFH1; H77c E2 and Con1 E2 differ by 20% in the intact form of $E2_{661}$ and differ by 15% in the core domain of E2 lacking the three variable regions. Microtitre plates were coated with GNA lectin and unfractionated antigen followed by blocking of unoccupied sites with BSA and addition of serial dilutions of immune serum. Bound immunoglobulins were detected with anti-guinea pig immunoglobulin's coupled to horse-radish peroxidase and visualised with TMB substrate.

The results show that the highest mean titres of cross-reactive antibody were elicited in animals that received peak 2 protein and were at least 2-fold higher than the other immune groups. (FIG. 38 A). The lowest mean titres of cross-reactive antibody were elicited by peak 4 protein and were 8 fold lower than peak 2 and 3 fold lower then the unfractionated immune group.

Examination of the ability of the immune serum to cross-react with the Con1 E2 core domain (Δ123) revealed that peak 2 immune serum elicited higher mean titres of antibody compared to peak 1, 3 and 4 immune groups (FIG. 38 B). The mean titre elicited by peak 2 (233750) was 26 fold higher than that of peak 4 immune group (9000). The monomeric peak 4 protein elicited the lowest mean titres of antibody cross reactive to the Δ123 core domain of Con1 compared to all other immune groups. (FIG. 38 B).

Example 21

Cross-Reactivity of Δ123 $E2_{661}$-his Immune Serum to Con1 Wild Type and Δ123 $E2_{661}$-his Antigens The ability of immune serum obtained from guinea pigs vaccinated with one of H77c Δ123 $E2_{661}$-his protein peaks 1-4 or unfractionated mixture to cross-react with the unfractionated mixtures of genotype 1b Con1 WT $E2_{661}$-his antigen and Δ123 $E2_{661}$-his antigen were compared in an enzyme immunoassay. Microtitre plates were coated with GNA lectin and unfractionated antigen followed by blocking of unoccupied sites with BSA and addition of serial dilutions of immune serum. Bound immunoglobulins were detected with anti-guinea pig immunoglobulin's coupled to horse-radish peroxidase and visualised with TMB substrate.

The results show that animals vaccinated with peak 1 (mean 220000) and 2 (mean 300000) proteins elicited the highest mean titres of antibody cross-reactive with the WT Con1 $E2_{61}$ antigen and were at least 2 fold higher than mean titres of the other immune groups (FIG. 39 A). The lowest mean titres of cross-reactive antibody were elicited by peak 4 protein (mean 20000) compared to the other groups.

Examination of the ability of the immune serum to cross react with the Con1 E2 core domain (Δ123) revealed that peak 1 and 2 immune serum had higher mean titres of antibody cross reactive to the core domain of Con1 $E2_{661}$-his compared to the other immune groups with mean titres of 217500 and 2887500, respectively (FIG. 39 B). The lowest mean titres of cross-reactive antibody directed to the core domain were elicited by peak 4 protein (mean 39600) compared to the other groups.

Example 22

Cross Reactivity of Δ123 $E2_{661}$-his Immune Serum to JFH1 WT and Δ123 $E2_{661}$-his Antigens The ability of immune serum obtained from guinea pigs vaccinated with one of H77c Δ123 $E2_{661}$-his protein peaks 1-4 or fractionated mixture to cross-react with the unfractionated mixtures of JFH1 WT $E2_{661}$ antigen and Δ123 $E2_{661}$ antigen were compared in an enzyme immunoassay. H77c E2 and JFH1 E2 differ by 31% in the intact form of $E2_{661}$ and differ by 20% in the core domain of E2 lacking the three variable regions. Microtitre plates were coated with GNA lectin and unfractionated antigen followed by blocking of unoccupied sites with BSA and addition of serial dilutions of immune serum. Bound immunoglobulins were detected with anti-guinea pig immunoglobulin's coupled to horse-radish peroxidase and visualised with TMB substrate.

The results show that Δ123 $E2_{661}$-his peak 1 and 2 antigens elicited significantly higher mean titres of antibody reactive to WT JFH1 E2 sequence, approximately two fold higher than the mean titres induced by unfractionated Δ123 $E2_{661}$-his (FIG. 40, A). The mean antibody titre elicited by peak 1 and 2 Δ123 $E2_{661}$-his was 50625 and 53500, respectively. Peak 3 (mean 23188) elicited similar mean titres of cross-reactive antibody compared to the unfractionated Δ123 $E2_{661}$-his. Peak 4 elicited low mean titres of cross-reactive antibody with a mean titre of 4225, 5 fold lower then the unfractionated immune group and 10 fold lower than peak 1 and 2.

Examination of the ability of Δ123 E2$_{661}$-his antibodies to recognise conserved epitopes present on a heterologous core domain of E2 revealed that peak 1 and 2 immune groups had the highest mean titres of antibodies (mean 36625 and 41250, respectively) (FIG. 40, B). The peak 3 (mean 13363) and 4 (mean 8088) immune groups had lower mean titres of cross reactive antibody than the unfractionated immune group (mean 22500) and approximately 3-4 fold lower than peak 1 and 2 immune groups.

Many modifications will be apparent to those skilled in the art without departing from the scope of the present invention.

TABLE 1

Vaccine groups of guinea pigs

| group | antigen | amount (μg) | adjuvant | No of pigs |
|---|---|---|---|---|
| 1 | Monomer | 30 | ISCOMATRIX™ | 4 |
| 2 | Monomer | 100 | ISCOMATRIX™ | 4 |
| 3 | Dimer | 30 | ISCOMATRIX™ | 4 |
| 4 | Dimer | 100 | ISCOMATRIX™ | 4 |
| 5 | Mixed | 30 | ISCOMATRIX™ | 4 |
| 6 | Mixed | 100 | ISCOMATRIX™ | 4 |
| 7 | no antigen | — | ISCOMATRIX™ | 4 |

BIBLIOGRAPHY

Angus and Patel, *Future Microbiol* 6: 279-94, 2011
Atherton and Shephard, *Peptide Synthesis*. In Nicholson ed., *Synthetic Vaccines*, published by Blackwell Scientific Publications, Chapter 9
Ausubel et al., *Current Protocols in Molecular Biology*, Green Pub. Associates and Wiley-Interscience, New York, 1988
Ausubel et al., Current Protocols in Molecular Biology, John Wiley & Sons Inc, Chapters 10 and 16, 1994
Ausubel et al., *Current Protocols in Molecular Biology*, Supplement 47, John Wiley & Sons, New York, 1999
Bartosch et al., *J Biol Chem* 278: 41624-30, 2003
Blish et al., *PLoS Med* 5, 9e, 2008
Coligan et al., *Current Protocols In Protein Science*, John Wiley & Sons. Inc., Chapters 1, 5 and 6, 1995-1997
Colowick and Kaplan, eds., *Methods In Enzymology*, Academic Press, Inc.
Cox and Coulter, "Advances in Adjuvant Technology and Application", in *Animal Parasite Control Utilizing Biotechnology*, Chapter 4, Ed. Young, W. K., CRC Press 1992
Cox and Coulter, *Vaccine* 15(3): 248-256, 1997
Dorner, et al., *Nature* 474: 208-11, 2011
Drummer et al., *Biochem Biophys Res Commun* 328: 251-257, 2005
Drummer et al., *FEBS Lett* 546: 385-90, 2003
Drummer et al., *J Virol* 76: 11143-7, 2002
Fields et al., eds, *Virology, 3rd Edition*, Lippincott-Raven, Philadelphia
Harris et al., *J Biol Chem* 285: 21092-102, 2010
Joklik ed., *Virology, 3rd Edition,* 1988; Fields and Knipe, eds, *Fundamental Virology,* 2nd Edition, 1991
Kaufmann et al., *Proc Natl Acad Sci USA* 107: 18950-5, 2010
Koutsoudakis et al., *J Virol* 81: 588-98, 2007
Kozak and Shatkin, *Methods Enzymol,* 60: 360-375, 1979
Kozak, *Biochimie.,* 76(9): 815-21, 1994
Kozak, *J Cell Biol,* 108(2): 229-241, 1989
Kozak, *Mamm Genome,* 7(8): 563-74, 1996
Law et al., *Nat Med* 14: 25-7, 2008
Lindenbach et al., *Science* 309(5734): 623-626, 2005
Lusso et al., *J Virol* 79: 6957-68, 2005
Mancini et al., *PLoS One* 4, e8254, 2009
McCaffrey et al. *J Virol* 81: 9584-90, 2007
McKeating et al. *Virol* 78: 8496-505, 2004
Pestka et al., *Proc Natl Acad Sci USA* 104: 6025-30, 2007
Pileri et al. *Science* 282: 938-41, 1998
Reed and Muench, *A simple method of estimating fifty percent endpoints*, The American Journal of Hygiene 27: 493-497, 1938
Remington's Pharmaceutical Sciences, 18th Ed., Mack Publishing, Company, Easton, Pa., U.S.A., 1990
Roberge et al. *Science,* 269(5221): 202-204, 1995
Rose et al., *A Laboratory Course Manual*, Cold Spring Harbor Laboratory, Cold Spring Harbor, N.Y., 1990
Sambrook et al., *Molecular Cloning: A Laboratory Manual* (2nd ed.). Cold Spring Harbour Laboratory, Cold Spring Harbour, N.Y., Sections 13, 16 and 17, 1989
Sharp and Cowe, *Yeast,* 7: 657-678, 1991
Stamataki et al., *Clin Liver Dis* 12: 693-712, 2008
Stiasny et al., *J Virol* 80: 9557-68, 2006
Sultana et al., *J Immunol* 183: 650-60, 2009
Vanwolleghem et al., *Hepatology* 47: 1846-55, 2008
Weir and Blackwell, eds., *Handbook of Experimental Immunology, Vols. I-IV*, Blackwell Scientific Publications, 1986
Youn et al., *Hepatology* 42: 1429-36, 2005
Zhang, et al., *J Virol* 78: 1448-55, 2004

The invention claimed is:

1. A pharmaceutical composition, comprising hepatitis C virus (HCV) Envelope 2 (E2) glycoprotein and a pharmaceutically or physiologically acceptable carrier and/or diluent, wherein the HCV E2 is more than 80%, by weight, trimeric and higher order forms of HCV E2 glycoprotein, or higher order forms of HCV E2 glycoprotein, whereby the composition, upon administration, elicits an immune response.

2. The pharmaceutical composition of claim 1, comprising hepatitis C virus (HCV) Envelope 2 (E2) glycoprotein, wherein the HCV E2 is more than 80%, by weight, trimeric HCV E2 glycoprotein.

3. The pharmaceutical composition of claim 1, comprising hepatitis C virus (HCV) Envelope 2 (E2) glycoprotein, wherein the HCV E2 is more than 80%, by weight, higher order forms of HCV E2 glycoprotein.

4. The pharmaceutical composition of claim 1, comprising hepatitis C virus (HCV) Envelope 2 (E2) glycoprotein, wherein the HCV E2 is more than 80%, by weight, trimeric and higher order forms of HCV E2 glycoprotein.

5. The pharmaceutical composition of claim 1, further comprising an adjuvant.

6. The pharmaceutical composition of claim 5, wherein the adjuvant is a saponin-based adjuvant that comprises cholesterol and sterol.

7. A method for eliciting an immune response in a subject or patient, the method comprising administering to the subject or patient an effective amount of the composition of claim 1 for a time and under conditions sufficient to elicit an immune response.

8. A method for immunizing a subject against infection from HCV, comprising administering to the subject the composition of claim 1.

9. A method for treating or preventing HCV infection in a subject, comprising administering to the subject the composition of claim 1 for a time and under conditions sufficient to treat or prevent HCV infection.

10. The pharmaceutical composition of claim 1, wherein the amount of monomer is less than 10%, by weight.

11. The pharmaceutical composition of claim 1, wherein the amount of monomer is less than 5%, by weight.

12. The pharmaceutical composition of claim 1, wherein the amount of monomer is less than 1%, by weight.

* * * * *

UNITED STATES PATENT AND TRADEMARK OFFICE
CERTIFICATE OF CORRECTION

PATENT NO. : 9,884,109 B2
APPLICATION NO. : 13/989598
DATED : February 6, 2018
INVENTOR(S) : Heidi Drummer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 680 days.

Signed and Sealed this
Fourth Day of September, 2018

Andrei Iancu
*Director of the United States Patent and Trademark Office*